United States Patent [19]
Tsuruta et al.

[11] Patent Number: 5,389,098
[45] Date of Patent: Feb. 14, 1995

[54] SURGICAL DEVICE FOR STAPLING AND/OR FASTENING BODY TISSUES

[75] Inventors: Minoru Tsuruta; Shiro Bito; Shuichi Kimura; Akito Mukaizawa; Seiji Kuramoto; Tsuyoshi Tsukagoshi; Akio Nakata; Akihiro Taguchi; Kazuhiko Oozeki; Hitoshi Mizno; Shuichi Takayama; Yoshinao Oaki; Keisuke Saito; Toshihiko Suzuta, all of Tokyo, Japan

[73] Assignee: Olympus Optical Co., Ltd., Tokyo, Japan

[21] Appl. No.: 62,182

[22] Filed: May 14, 1993

[30] Foreign Application Priority Data

| May 19, 1992 | [JP] | Japan | 4-126246 |
| May 19, 1992 | [JP] | Japan | 4-126248 |
| May 20, 1992 | [JP] | Japan | 4-127602 |
| Jun. 3, 1992 | [JP] | Japan | 4-142930 |
| Jun. 4, 1992 | [JP] | Japan | 4-144302 |
| Jun. 4, 1992 | [JP] | Japan | 4-144625 |
| Mar. 30, 1993 | [JP] | Japan | 5-72553 |

[51] Int. Cl.$^6$ .............................. A61B 17/36
[52] U.S. Cl. ............................ 606/41; 606/32; 606/40; 606/49; 606/142
[58] Field of Search ............... 606/32, 41, 45–47, 606/51, 52, 139, 142, 143; 227/901, 902

[56] References Cited

U.S. PATENT DOCUMENTS

| 4,944,443 | 7/1990 | Oddsen et al. | |
| 5,084,057 | 1/1992 | Green | 606/142 |
| 5,104,394 | 4/1992 | Knoepfler | 606/143 |
| 5,147,356 | 9/1992 | Bhatta | 606/37 |
| 5,207,691 | 5/1993 | Nardella | 606/41 |

*Primary Examiner*—Stephen C. Pellegrino
*Assistant Examiner*—Michael Peffley
*Attorney, Agent, or Firm*—Frishauf, Holtz, Goodman & Woodward

[57] ABSTRACT

A surgical device for stapling and fastening body tissues, comprises an insertion section extending from an operation section for insertion into a body cavity, stapling member connected to a distal end of the insertion section, for treating body tissues with a high-frequency current within a body cavity. The stapling member includes an anvil and a cartridge between which the tissues are sandwiched, and a cutter. Staples are applied to the anvil from the cartridge for stapling the tissues and the cutter cuts the tissue while it applies a high-frequency current thereto.

16 Claims, 35 Drawing Sheets

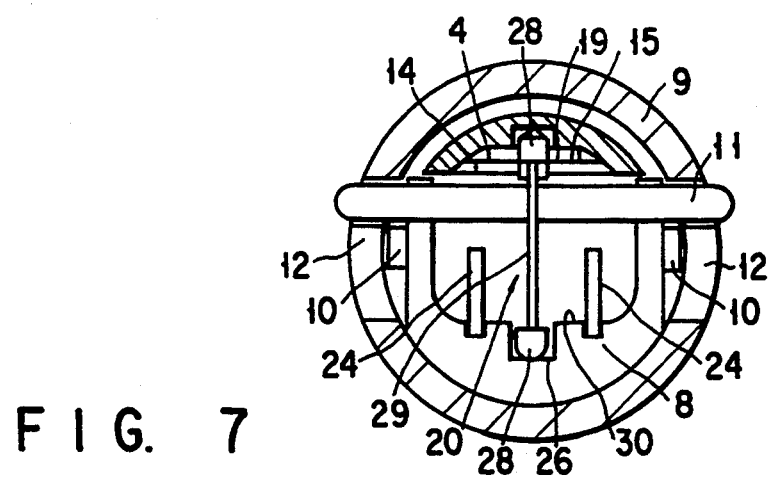
F I G. 7
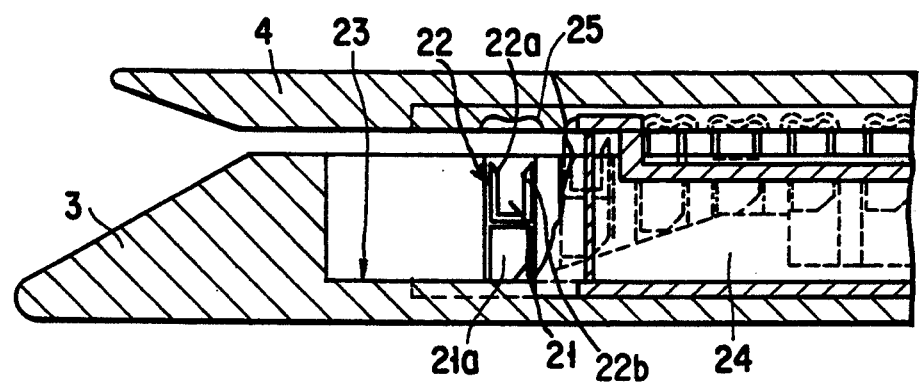
F I G. 8
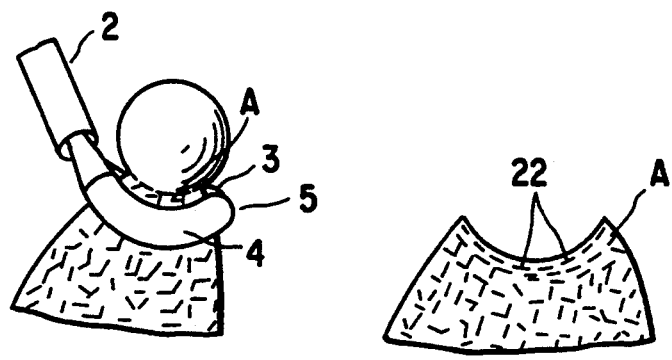
F I G. 9     F I G. 10

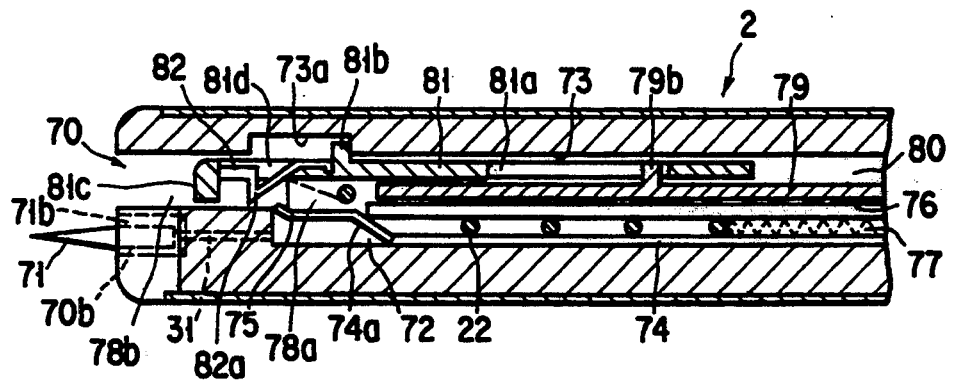
FIG. 30
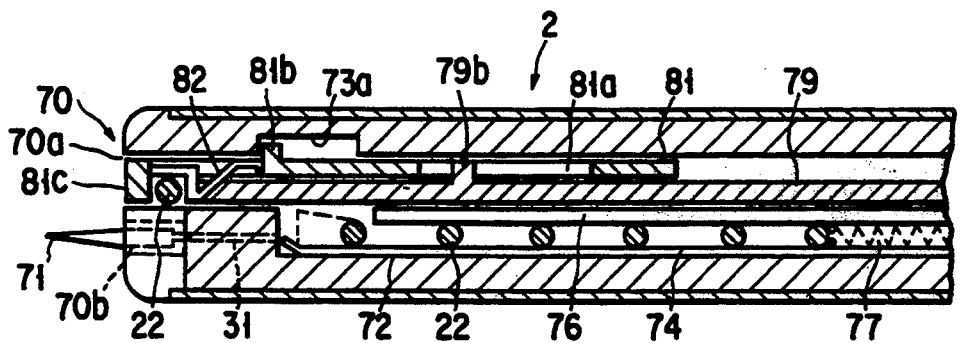
FIG. 31
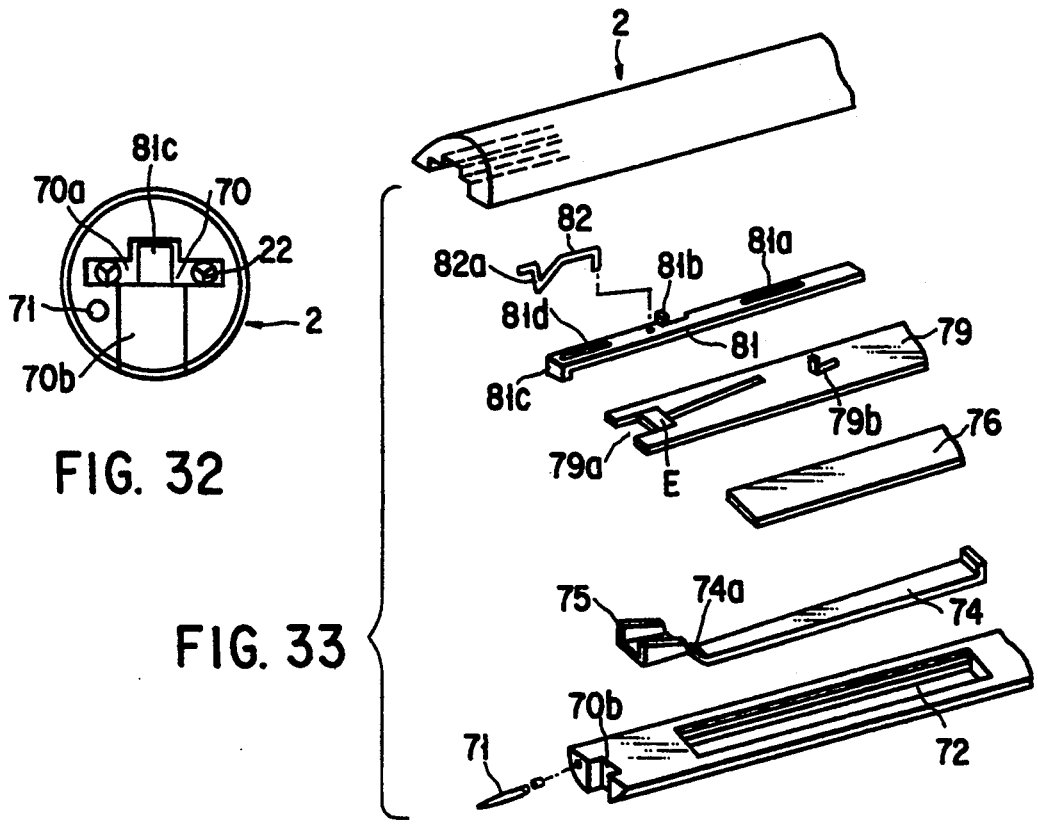
FIG. 32
FIG. 33

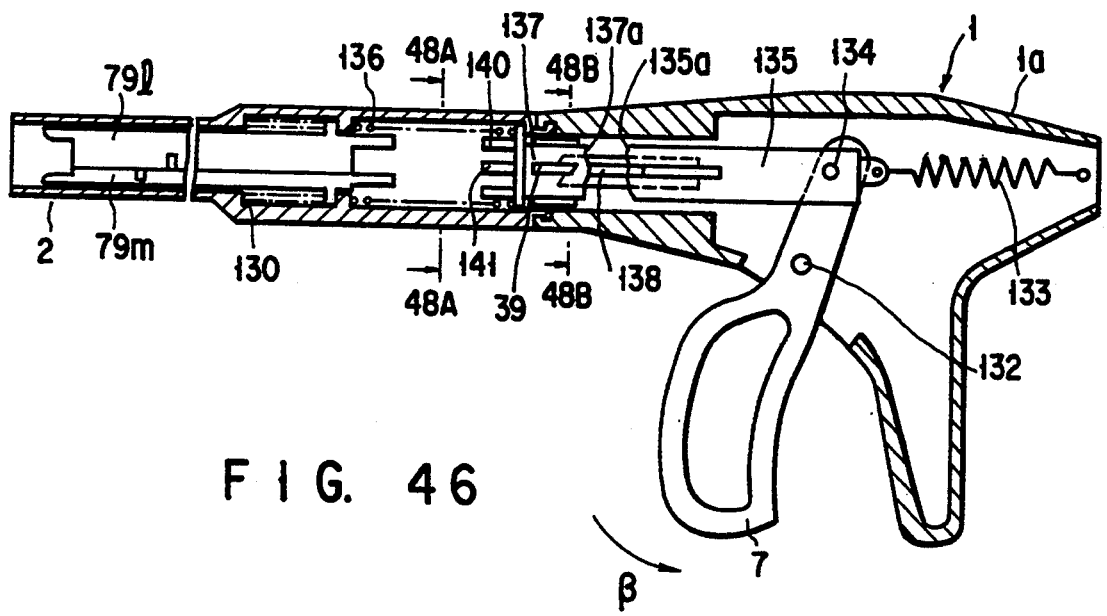
FIG. 46
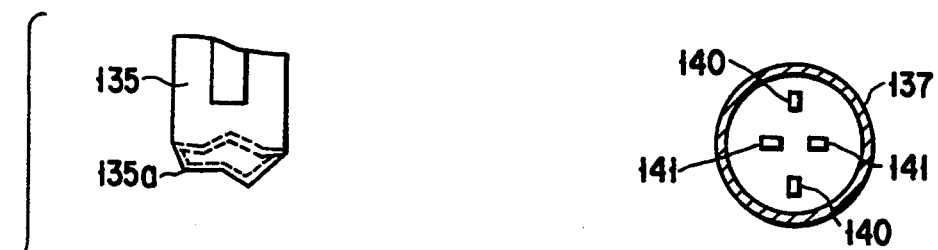
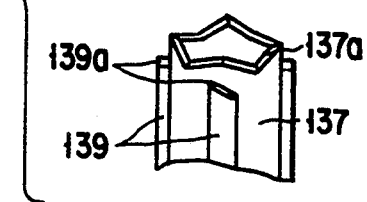
FIG. 47
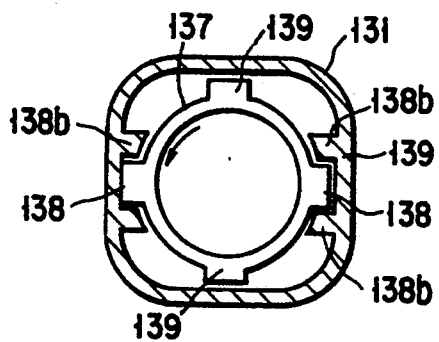
FIG. 48A
FIG. 48B

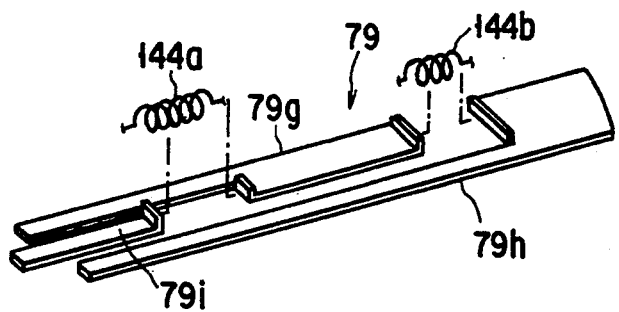
F I G. 52
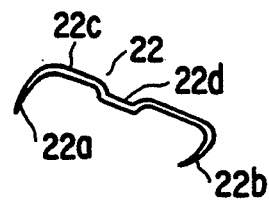
F I G. 54A
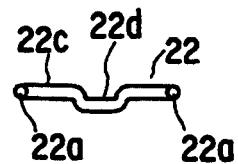
F I G. 54B

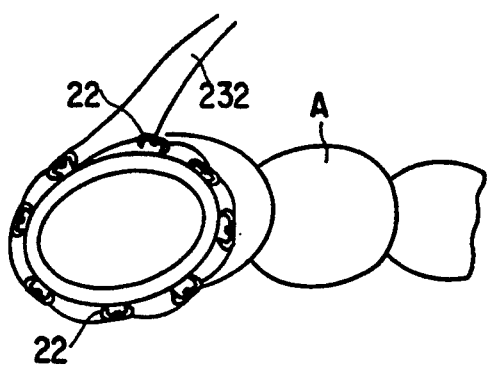
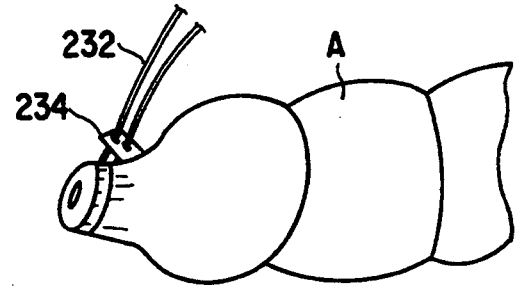
FIG. 77A     FIG. 77B
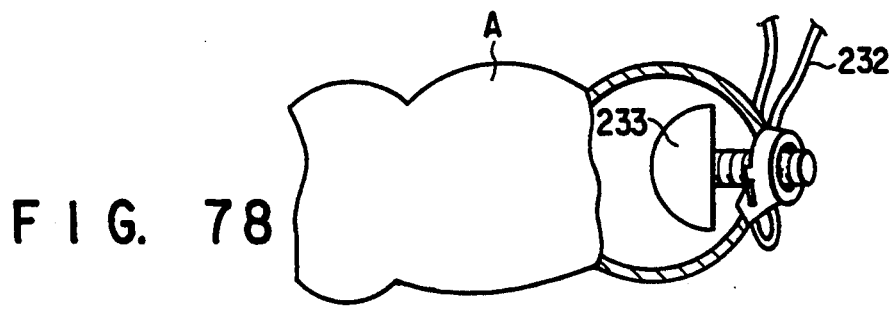
FIG. 78
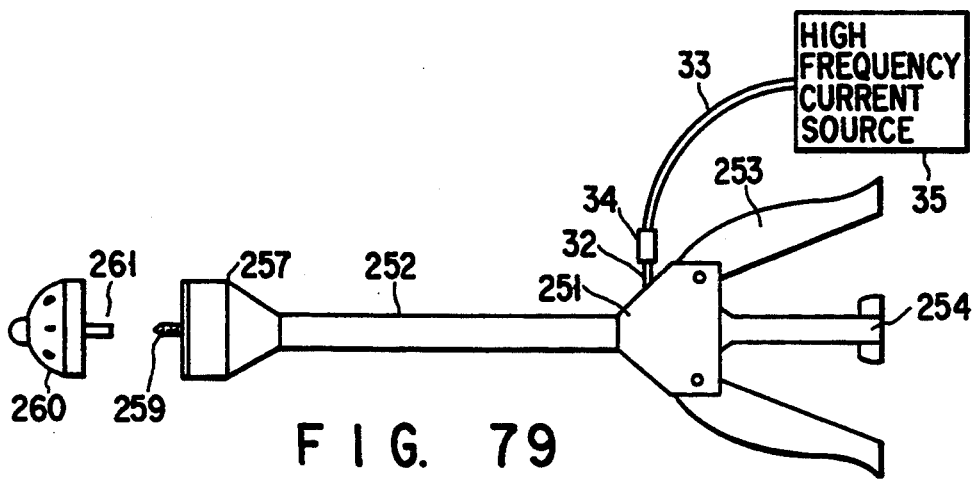
FIG. 79
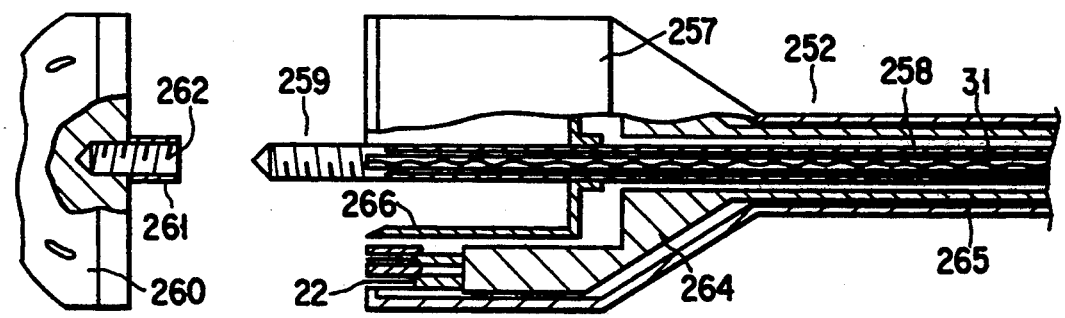
FIG. 80

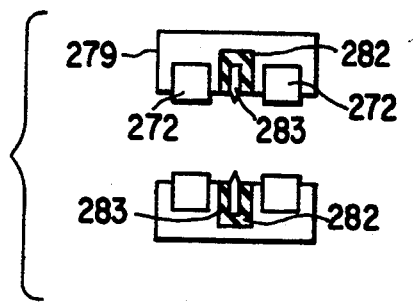
F I G. 85
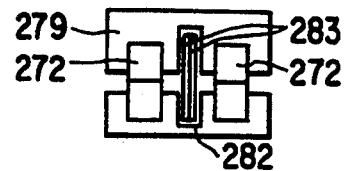
F I G. 87
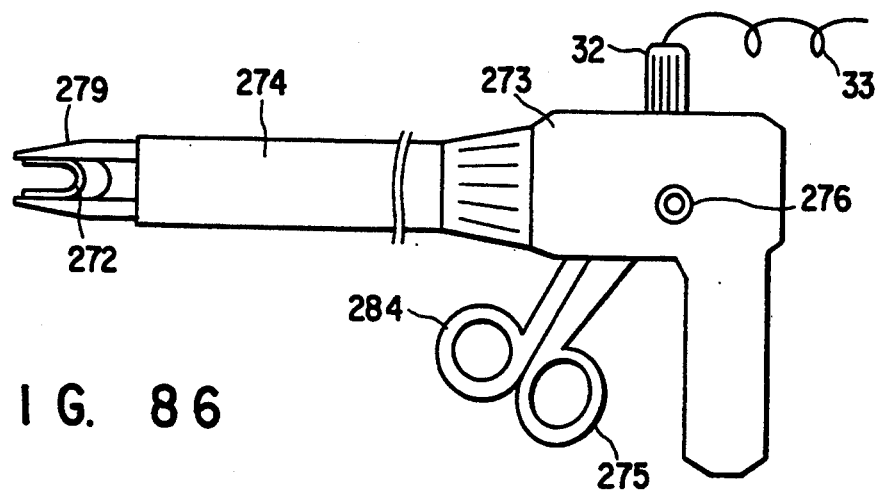
F I G. 86
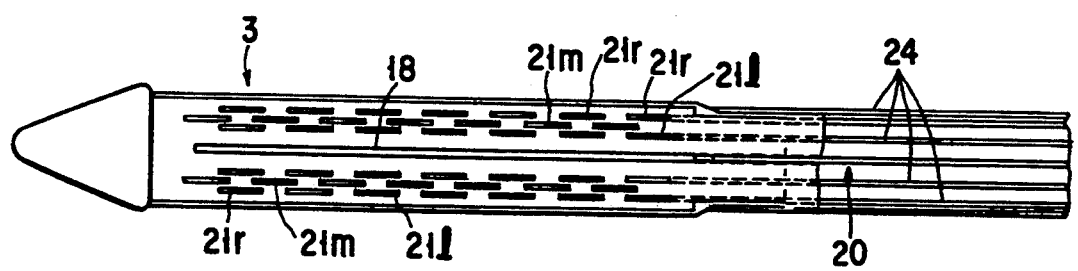
F I G. 88
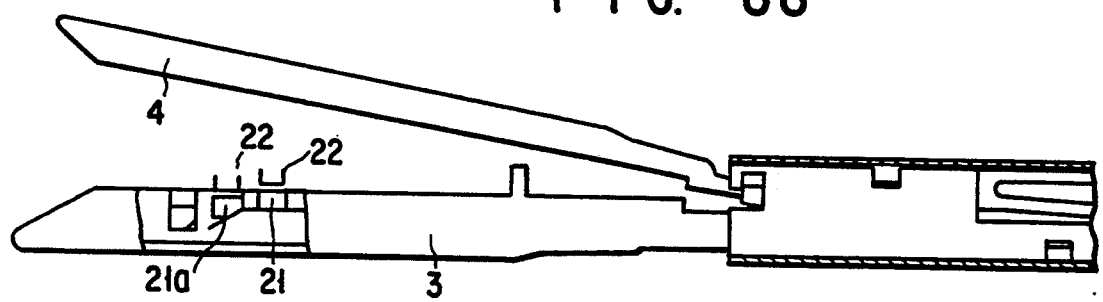
F I G. 89

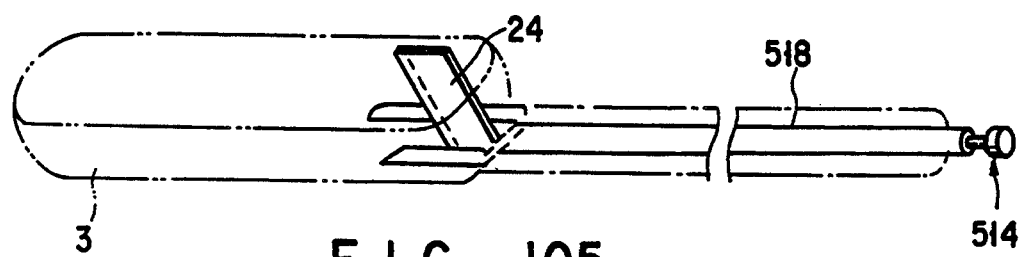
F I G. 105
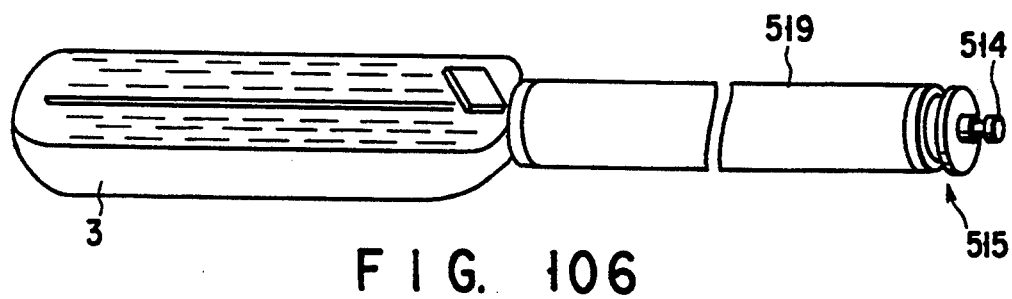
F I G. 106
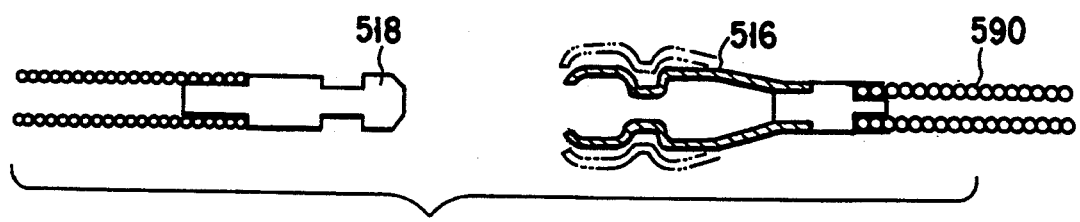
F I G. 107
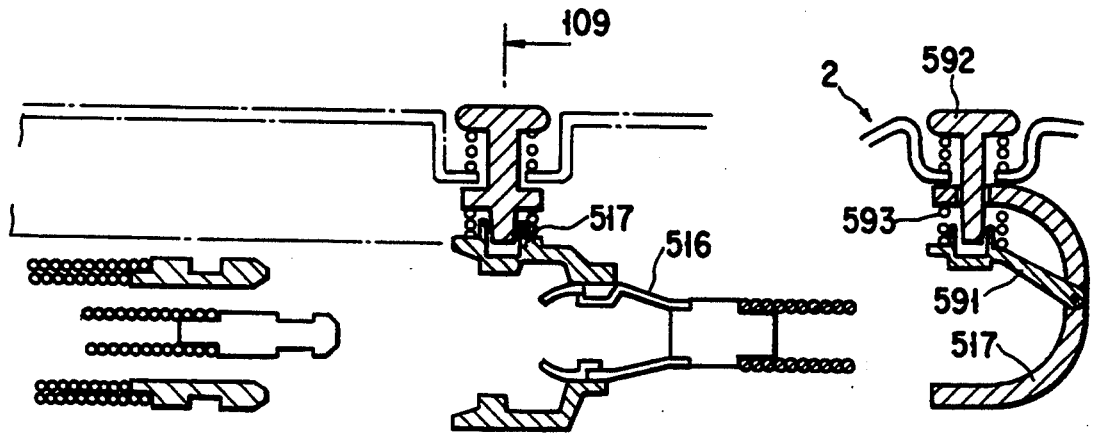
F I G. 108
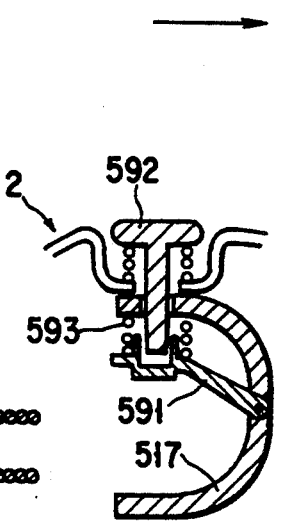
F I G. 109

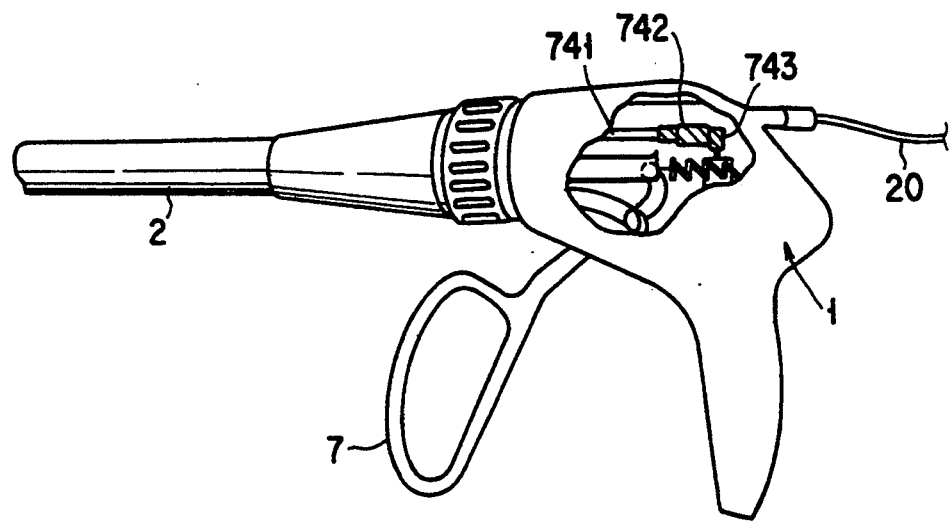
F I G. 113
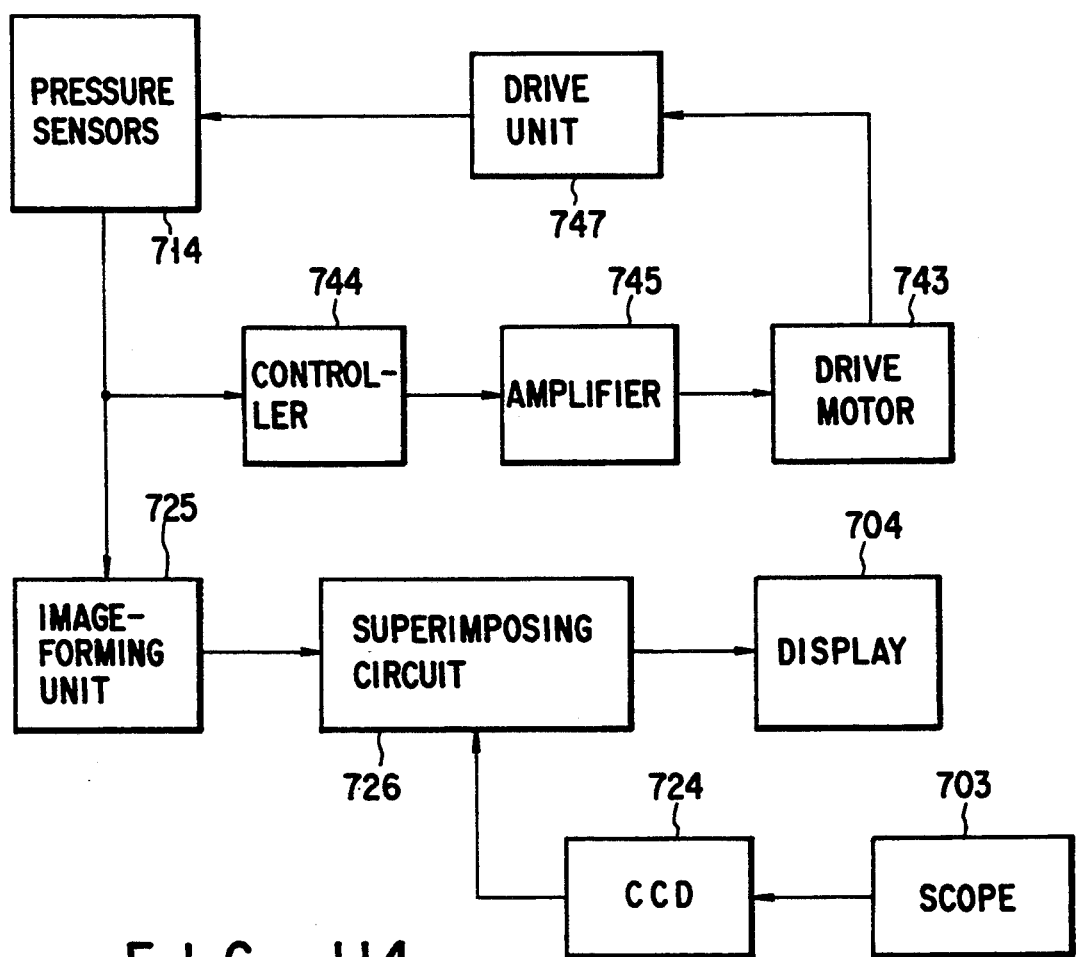
F I G. 114

SURGICAL DEVICE FOR STAPLING AND/OR FASTENING BODY TISSUES

BACKGROUND OF THE INVENTION

1. Field of the Invention

The present invention relates to a surgical device for stapling and/or fastening body tissues.

2. Description of the Related Art

To remove a gallstone or gallstones from the gallbladder, for example, the gallbladder needs to be extracted in order to prevent the forming of other stones. To extract the gallbladder, it is necessary to cut the junction between the gallbladder and the bile duct. Extending through this junction are bile arteries and the bile duct. Hence, to extract the gallbladder without damaging the same, the bile duct must be cut with a knife or the like and must be stapled immediately.

Various staplers are known which are designed for use in gallstone-removing procedures. Any of these staplers is inserted through an incision made in the abdominal wall into the body cavity where the gallbladder is located. The stapler is manipulated to apply staples to the body tissues, thereby to fasten them together. Some staplers of this type are disclosed in, for example, Published Examined Japanese Utility mode Applications Nos. 38-19282 and 60-41924 and Publish Unexamined Japanese Patent Application No. 3-12126.

The stapler disclosed in Published Examined Japanese Utility Model Application No. 38-19282 is designed for stapling the stomach. The stapler comprises a staple holder and an anvil. The staple holder contains staples and has a staple-feeding mechanism. Both the staple holder and the anvil curve in the same way as the stomach does. The staple holder is rotatably hinged to the anvil by a pin.

The stapler disclosed in Published Examined Japanese Utility Model Application No. 60-41924 is designed to staple a cancerous tumor. This stapler comprises a scissors-like stapling body. The stapling body is slender, consisting of a grip and a staple-holding section. The staple-holding section comprises a staple holder and an anvil which are hinged together at one end. Both the staple holder and the anvil curve in the same way as the cancerous organ does, and constitute a beak-shaped unit while placed in their closed positions.

The stapler disclosed in Published Unexamined Japanese Patent Application No. 3-12126 is designed to staple together body tissues located within a body cavity. This stapler comprises an insertion section, a stapling member, a firing handle and an operating handle. The stapling member is connected to the distal end of the insertion section and comprises an anvil and a cartridge. The cartridge is rotatably connected to the anvil and used to contain staples. The firing handle is coupled to the proximal end of the insertion section; it is squeezed to eject a staple from the cartridge. The operating handle is connected to the proximal end of the insertion section, too; it is operated to open and close the stapling member.

The stapler disclosed in Published Examined Japanese Utility Model Application No. 38-19282 has no insertion section, and cannot be inserted into a body cavity through an incision made in a body wall. Since the staple holder has no means for cutting the body tissues stapled together, a separate cutting instrument must be used to cut the body tissues.

When the stapler disclosed in Published Examined Japanese Utility Model Application No. 60-41924 is employed, it is necessary to incise a body wall (e.g., the abdominal wall, the chest wall, or the like) so that the insertion section may be inserted into a body cavity, giving rise to great attacks. Further, since the stapler has no means for cutting the body tissues stapled together, a separate cutting instrument must be used to cut the body tissues.

The stapling member of the stapler disclosed in Published Unexamined Japanese Patent Application No. 3-12126 is straight, axially aligned with the insertion section. If there is a conglutination in the body cavity, narrowing the cavity, it would be difficult to move the insertion section to the target body tissues. Further, if the target tissues are located away from the axis of the insertion section, a forceps or the like must be inserted into the body cavity to hold and place the tissues on the axis of the insertion section.

As described above, the conventional staplers have but low operability, requiring other surgical instruments to perform surgical operations. When they are used, it usually take a long time to complete the operations, causing much pain and toil on the part of the patient. None of the conventional staplers cannot perfectly stop the flow of blood or other body fluid from the body tissues after the tissues have been severed and stapled. There are two reasons for this. First, a gap remains between the anvil and the staple holder (or the cartridge) even when they are set in their closed positions. Second, a single clip or staple applied to body tissues to stop bleeding gets loose due to the force which the tissues exert on the clip or staple as they restore their shapes.

Generally, any bleeding tissues or organs, whether fastened or not with clips or staples, are solidified by means of an electric knife or the like, thereby stopping the bleeding. During endoscopic procedures, however, it is cumbersome for surgeons to remove the stapler or the clip applicator from the distal end of the endoscope and then to attach the electric-knife electrode.

SUMMARY OF THE INVENTION

The object of the present invention is to provide a surgical device which is inserted into a body cavity through an incision made in a body wall, for stapling, fastening, and cutting the body tissues located in the cavity, and which can reliably stop the bleeding at the stapled or fastened tissues, helping to shorten the time of a surgical operation.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 7 is a cross-sectional view of the distal end portion of the insertion section;

FIG. 8 is a sectional side view showing a part of the stapling member;

FIG. 9 is a diagram explaining how stitch body tissues together by means of the surgical stapler shown in FIG. 1;

FIG. 10 is a diagram showing the body tissues stitched together;

FIG. 30 is a sectional side view of the stapling section of the insertion section of the stapler, explaining how staples are loaded into the stapling section;

FIG. 31 is a sectional side view of the stapling section, explaining how each staple is deformed to fasten body tissues together;

FIG. 32 is a front view of the stapling section of the second embodiment;

FIG. 33 is an exploded view showing the stapling section;

FIG. 46 is a sectional side view of the stapler according to the third embodiment;

FIG. 47 is a perspective view showing the hollow cylindrical pusher and switching member, both incorporated in the operation section of the stapler;

FIG. 48A is a cross-sectional view, taken along line 48A—48A in FIG. 46; FIG. 48B is a across-sectional view, taken along line 48B—48B in FIG. 46 FIGS. 49A, 49B, and 49C are diagrams explaining how the stapler applies a staple to stitch body tissues together;

FIG. 52 is an exploded view showing a modified staple pusher;

FIG. 54A is a perspective view of a modified staple, and FIG. 54B is a front view thereof;

FIGS. 77A and 77B are perspective view of a severed tissue, FIG. 77A showing the tissue to be tied at its severed edge, and FIG. 77B showing the tissue tied at its severed edge;

FIG. 78 is a perspective view, explaining how an anvil is inserted into the tissue through the severed edge thereof;

FIG. 79 is a side view illustrating a stapler according to a fifth embodiment of the present invention;

FIG. 80 is a cutaway side view showing the distal end portion of the stapler;

FIGS. 84 and 85 are diagrams showing a modification of the clip applicator shown in FIG. 82, respectively;

FIGS. 86 and 87 are diagrams showing another modification of the clip applicator;

FIG. 88 is a plan view showing the cartridge of a modified stapling member;

FIG. 89 is a side view showing the modified stapling member and the distal end portion of the insertion section, to which the stapling member is connected;

FIG. 105 is a perspective view showing a pusher plate and a thin coiled wire having a first coupling, both incorporated in the stapler of FIG. 104;

FIG. 106 is a perspective view of a thick coiled wire having a second coupling, which is used in the stapler of FIG. 104;

FIG. 107 is a diagram showing the first and second coupling;

FIG. 108 is a sectional view illustrating the mechanism coupling the cartridge and insertion section of the stapler;

FIG. 109 is a cross-sectional view, taken along line 109—109 in FIG. 108;

FIG. 113 is a cutaway perspective view showing the stapler incorporated in the surgical operation system; and FIG. 114 is a block diagram showing the components of the surgical operation system.

DETAILED DESCRIPTION OF THE PREFERRED EMBODIMENTS

A stapler according to a first embodiment of the present invention will be described with reference to FIGS. 1 to 12.

Figure 1:
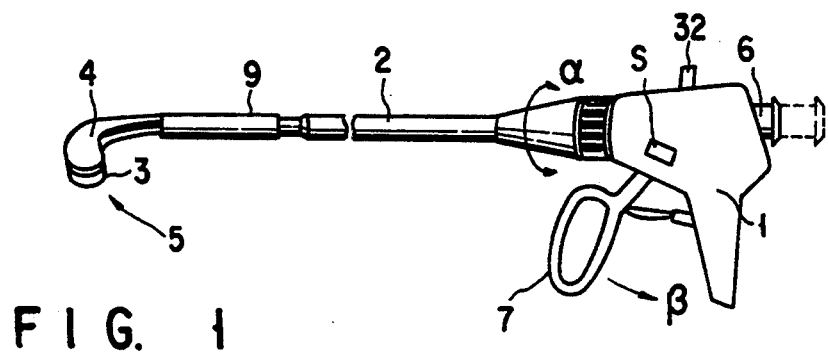
FIG. 1 is a perspective view of a surgical stapler according to a first embodiment of this invention.

As shown in FIG. 1, the stapler comprises an operation section 1, an insertion section 2, and a stapling member 5. The insertion section 2 is connected at its proximal end to the operation section 1. The insertion section 2 can freely rotate around its axis in the direction of arrow α. The stapling member 5 comprises a cartridge 3 and an anvil 4 and is coupled to the distal end of the insertion section 2. The operation section 1 has an operating member 6 and a staple-driving handle 7. The operating member 6 can be pushed and pulled to open and close the stapling member 5. When squeezed in the direction of arrow β, the handle 7 drives staples into living tissues to stitch the tissues together.

Figure 2:
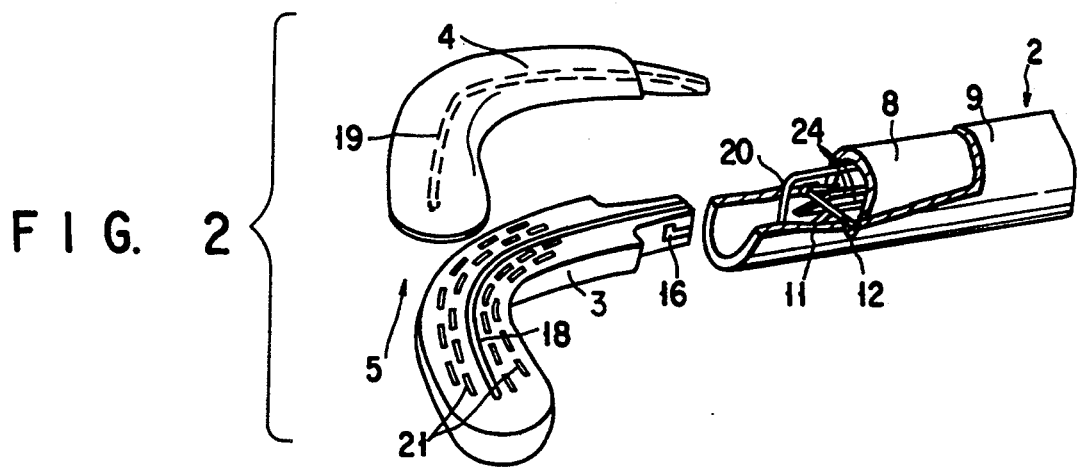
FIG. 2 is an exploded view showing the stapler illustrated in FIG. 1.
Figure 3:
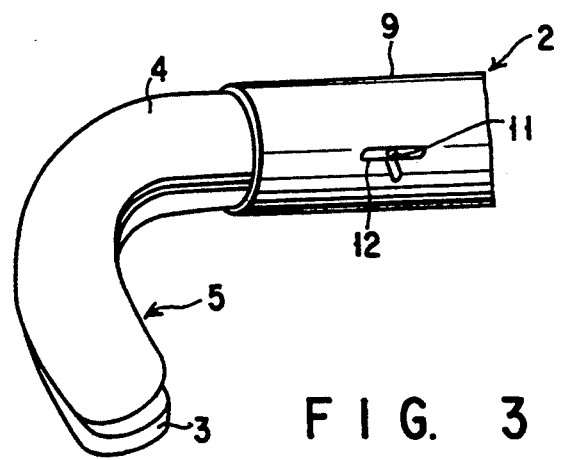
FIG. 3 is an enlarged view showing the distal end portion of the insertion section of the stapler.
Figure 4:
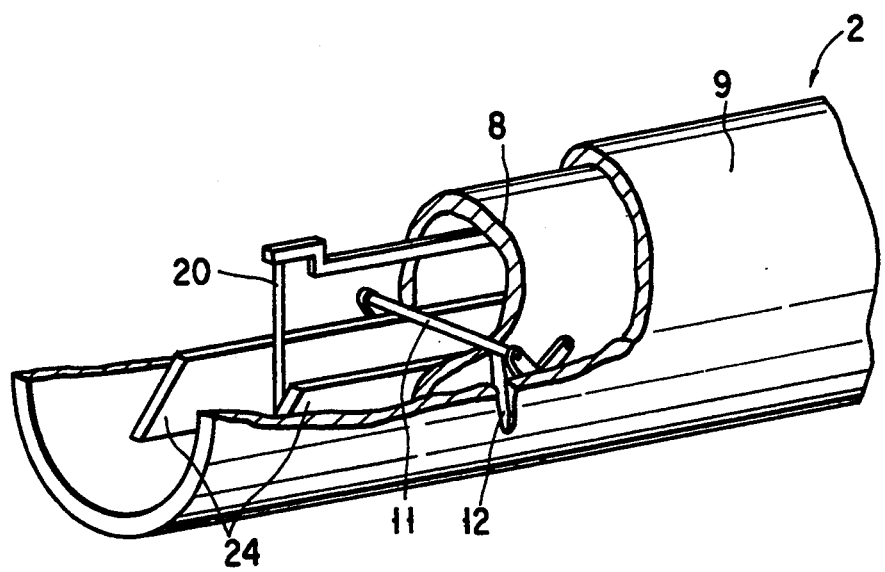
FIG. 4 is a cutaway perspective view showing the stapling member of the stapler and also the distal end portion of the insertion section thereof.
Figure 5:
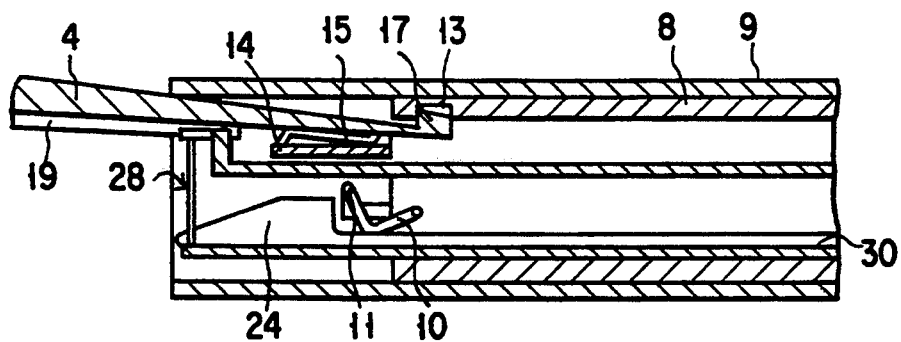
FIG. 5 is a sectional side view of the distal end portion of the insertion section, illustrating the stapling member in its closed position.
Figure 6:
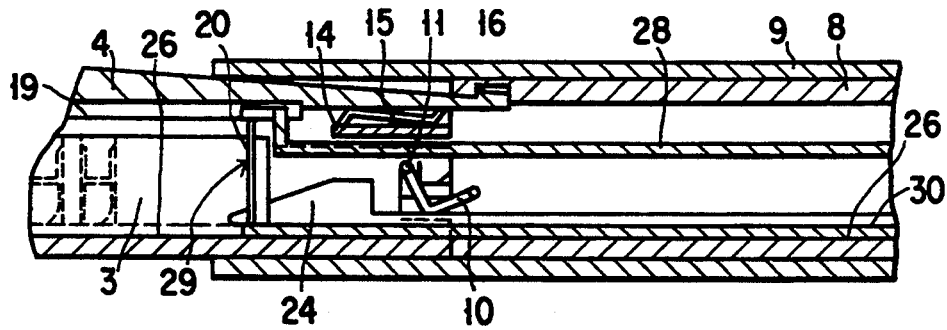
FIG. 6 is a sectional side view of the distal end portion of the insertion section, illustrating the stapling member in its open position.

As shown in FIGS. 2 to 8, the insertion section 2 comprises an inner tube 8 and an outer tube 9 mounted on the outer peripheral surface of the inner tube 8. The outer tube 9 can move back and forth, sliding on the inner tube 8, along the axis of the insertion section 2. The distal end portion of the outer tube 9 extends forward farther than the distal end of the inner tube 8. As FIGS. 5 and 6 show, a pair of connectors 10, each formed of a V-shaped spring, are pivotally connected at their proximal ends to the sides of the distal end portion of the inner tube 8. The proximal halves of the connectors 10 extend parallel to each other. A hinge pin 11 extends at right angles to the axis of the inner tube 8, and bridged between the proximal halves of the connectors 10. The end portions of the pin 11 rest in the substantially T-shaped slits 12 which is cut in the sides of the outer tube 9 as best shown in FIG. 3. The slits 12 serve as guides allowing for the vertical movement of the connectors 10 and for the movement of the outer tube 9 against the inner tube 8.

As shown in FIG. 5, an engagement recess 13 is cut in the inner surface of the distal end portion of the inner tube 8. A strip-like projection 14 protrudes from that region of the distal-end face of the inner tube 8 which is located near the engagement recess 13. A leaf spring 15 is mounted on the upper surface of the projection 14.

As shown in FIG. 2, the cartridge 3 has an L-shaped hinge groove 16 in its proximal end, opening at the end face. The hinge pin 11 is inserted in the hinge groove 16. Thus, the pin 11 can move up and down and can be removed from the cartridge 3.

As can be understood from FIGS. 5 and 6, the anvil 4 has a projection 17 protruding from the upper surface of its proximal end portion. The projection 17 fits into the recess 13 cut in the inner surface of the distal end portion of the inner tube 8, when the proximal end portion of the anvil 4 is inserted into the distal end portion of the inner tube 8. Then, the proximal end portion of the anvil 4 contacts the leaf spring 15 mounted on the upper surface of the projection 14. The spring 15 therefore biases the proximal end portion of the anvil 4 upwards. The projection 17 of the anvil 4 is thereby remains in the recess 13 of the inner tube 8, whereby the anvil 4 is coupled to the inner tube 8.

As a result, the cartridge 3 can rotate around the hinge pin 11, and the anvil 4 can also rotate, with the projection 17 serving as fulcrum. Hence, the stapling member 5, comprised of the cartridge 3 and the anvil 4, can open and close. Normally, the stapling member 5 is in its open position because the cartridge 3 and the anvil 4 are biased away from each other, due to the spring force of the connectors 10 and that of the leaf spring 15 when the outer tube 9 is thrust forward, slipping on the outer surface of the inner tube 8, the inner surface of the distal end of the outer tube 9 abuts on the proximal end portion of the cartridge 3 and that of the anvil 4, pressing them toward each other. The stapling member 5 is thereby closed.

As most clearly shown in FIG. 2 to 4, the stapling member 5 curves by about 90°. The cartridge 3 and the anvil 4, which are curving so, have cutter-guiding grooves 18 and 19 formed in their inner flat surfaces, opposing each other. The grooves 18 and 19 extend along the axes of the cartridge 3 and the anvil 4 and, hence, are curving. A wire-cutter 20, which will be described later, can slide along the grooves 18 and 19.

The inner surface of the cartridge 3 has slits 21 arranged in four rows—two rows extending on one side of the cutter-guiding groove 18, and two rows on the other side of the groove 18. As shown in FIG. 8, pushers 21a are slidably placed in the slits 21, respectively, and U-shaped staples 22 are inserted in the slits 21 and mounted on the pushers 21a, respectively.

The staples 22 are made of electrically conductive material such as stainless steel, titanium or tantalum, or electrically insulating material such as polylactide, polyglycolide or polydioxanone. Which material is selected for the staples 22 is determined by the intended use of the staples 22.

A pair of plate-guiding grooves 23 extend within the cartridge 3, along the curving axis thereof. A pair of pusher plates 24 can be moved back and forth along the plate-guiding grooves 23 as will be described later.

The anvil 4 has shallow grooves 25 formed in its inner surface as is illustrated in FIG. 8. These grooves 25 are arranged in four rows,—two rows extending on one side of the cutter-guiding groove 19, and two rows on the other side of the groove 19. The grooves 25 will meet the corresponding slits 21 of the cartridge 3 when the cartridge 3 and the anvil 4 are closed together. Each of the grooves 25 has an arcuate bottom so that both legs 22a and 22b of the staple 22 may be bent inwards, or toward each other as the staple 22 is pushed against the bottom of the groove 25.

The wire-cutter 20 and the pusher plates 24 are located within the inner tube 8 of the insertion section 2.

The inner tube 8 has a groove 26 cut in its inner surface. This groove 26 is continuous to the cutter-guiding groove 18 of the cartridge 3 and the cutter-guiding groove 19 of the anvil 4. Slidably inserted in the groove 26 is a cutter holder 28. The cutter holder 28 has two wire-holding projections protruding from its distal-end face and spaced apart from each other. The wire-cutter 20, which is a wire, is stretched vertically between the wire-holding projections of the holder 28. The wire-cutter 20 and the cutter holder 28 constitute a knife unit 29.

As shown in FIG. 6, the inner surface of the inner tube 8 includes a pair of plate-guiding surfaces 30 which are flush with the bottom of the plate-guiding grooves 23 formed in the cartridge 3. The pusher plates 24 made of metal plates are slidably mounted on the plate-guiding surfaces 30, respectively. The distal end 24a of each pusher plate 24 inclines downwards as is illustrated in FIG. 4.

The wire-cutter 20 and the pusher plates 24 are fastened at their proximal ends to the upper end of the staple-driving handle 7 (FIG. 1). Alternatively, their proximal ends may be connected by connecting means such as wires to the upper end of the handle 7, not directly fastened thereto. When the handle 7 is squeezed in the direction of arrow $\beta$ shown in FIG. 1, the wire-cutter 20 and the pusher plates 24 are thrust forward through the inner tube 7, moving into the cartridge 3 and the anvil 4.

The outer tube 9 is coupled at its proximal end to the operating member 6. As mentioned above, the operating member 6 is mounted at the rear of the operation section 1 and can be pushed and pulled. Thus, when the member 6 is pushed forward to the position indicated by the solid lines in FIG. 1, the outer tube 9 is moved forward, sliding on the inner tube 8. Subsequently, the inner surface of the outer tube 9 abuts on the proximal ends of the cartridge 3 and the anvil 4, thereby closing the stapling member 5. Conversely, when the member 6 is pulled backward to the position indicated by the broken lines in FIG. 1, the outer tube 9 is moves backward, and its inner surface bias the proximal ends of the cartridge 3 and the anvil 4. As a result, the cartridge 3 and the anvil 4 are rotated away from each other, by virtue of the spring force of the connectors 10 and that of the leaf spring 15; the stapling member 5 is opened.

Figure 12:
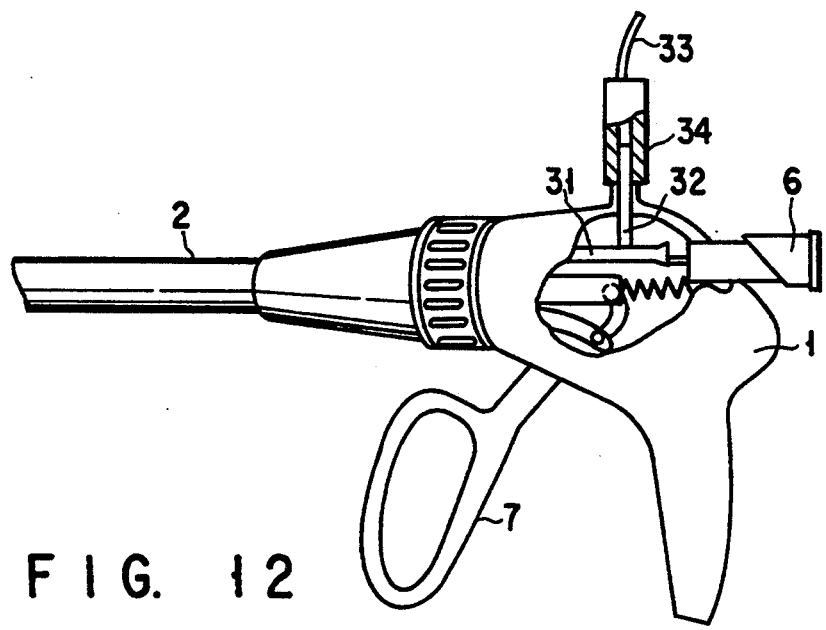
FIG. 12 is a cutaway side view showing the operation section of the stapler.

As illustrated in FIG. 12, an electric conductor member 31 extends through the operation section 1 and is connected at the distal end to the wire-cutter 20. The proximal end of the conductor 31 is connected to a connecting pin 32 protruding from the operation section 1. As may be understood from FIG. 1, a switch S is mounted on the rear end portion of the electric conductor 31, for supplying and not supplying a high-frequency current to the wire-cutter 20. The switch S is exposed on one side of the operation section 1 and can, therefore, be operated from outside.

Figure 11:
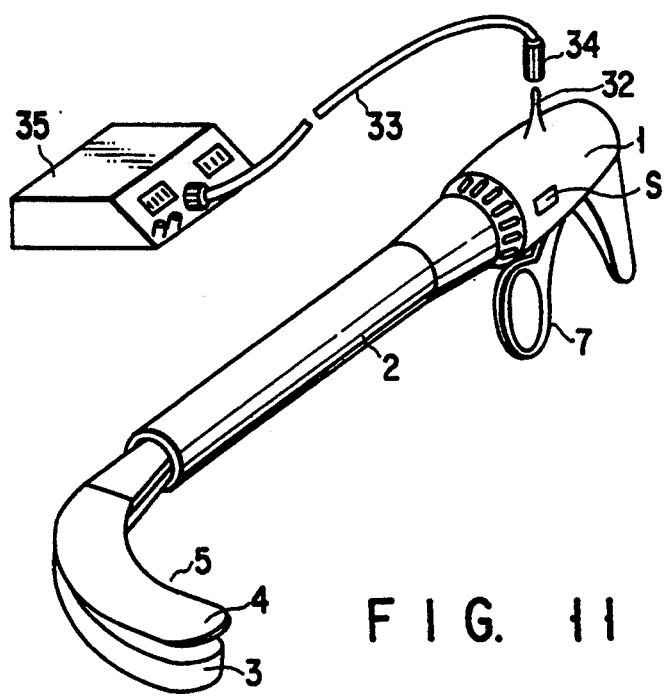
FIG. 11 is a perspective view showing the stapling system comprising the stapler and a high-frequency cautery device.

As FIG. 11 shows, a cable 33 has a connector 34 at one end. The connector 34 is coupled to the connecting pin 32. The other end of the cable 33 is connected to a high-frequency cautery device 35. The cautery device 35 can be controlled over a broad range to generate a high-frequency current which has a desired waveform and desired characteristics. Thus, the device 35 can supply a large incision current, a high coagulation current, or a mixed current serving as both an incision current and a coagulation current, in accordance with the use of the stapler shown in FIG. 1. Usually, a predetermined power of about 50 W is applied to the wire-cutter 20 to form an incision in a body wall. Nonetheless, the cautery device 35 can be controlled to set the output power at a suitable value in accordance with the location and/or condition of the living tissues which are to be stapled and severed.

The stapler described above is operated in the following way. A body wall or the like is incised. The stapling member 5 and the insertion section 2 are inserted into a body cavity through the incision. Since the stapling member 5 curves by about 90° with respect to the axis of the insertion section 2, it can be easily inserted into the body by rotating the section 2 in the direction opposite in that direction in which the member 5 is curving.

The insertion section 2 is inserted deeper into the body cavity, thus moving the stapling member 5 toward body tissues A to be stapled together. At this time, the operating member 6 is pulled to the position indicated by the broken lines in FIG. 1. The outer tube 9 is thereby pulled back, exposing the cartridge 3 and the anvil 4. Released from the outer tube 9, the cartridge 3 is rotated outwards by the spring force of the connectors 10, and the anvil 4 is rotated outwards by the force of the leaf spring 15. In other words, the stapling member 5 is opened. The member 5, now open, is moved such that the tissues A are caught between the cartridge 3 and the anvil 4. Then, the operating member 6 is pushed to the position represented by the solid lines in FIG. 1. The outer tube 9 is thereby moved forward, abutting at its inner surface on the distal end portion of the cartridge 3 and that of the anvil 4. The stapling member 5 is closed, thus clamping the body tissues A.

In this condition, the staple-driving handle 7 is squeezed in the direction of arrow $\beta$, moving the pusher plates 24 forward first through the inner tube 8 and then along the plate-guiding grooves 23, and also moving the wire-cutter 20 forward along the cutter-guiding grooves 18 and 19 formed in the opposing surfaces of the cartridge 3 and the anvil 4, respectively.

As the pusher plates 24 advance forward, their inclining distal ends 24a push up the pushers 21a of each row sequentially, ultimately driving the staples 22 into the tissues A, one after another. The legs 22a and 22b of each staple 22 pierce the living tissues A, abut on the bottom of the groove 25 formed in the inner surface of the anvil 4, and have their tips bent inwardly. As a result of this, the tissues A are stitched together with the staples 22 arranged in four parallel rows.

At the same time the tissues A are stitched together with four rows of staples 22, the wire-cutter 20 advances along the grooves 18 and 19. The cutter 20 cuts the tissues A along a curving line extending between the inner two rows of staples 22. This is because, as is best shown in FIG. 2, the grooves 18 and 19 extend between the inner two rows of slits 21 formed in the inner surface of the cartridge 3. Thus, the body tissues A are stapled and severed almost at the same time.

As the tissues A are stapled and severed, a high-frequency current is supplied from the cautery device 35 to the wire-cutter 20 of the knife unit 29 via the cable 33 and the electric conductor 31. Therefore, the tissues A is cauterized while being stitched together. Since the tissues A are severed while being cauterized, there is no risk of bleeding at the severed portions of the living tissues A.

Supplied with the cautery current (i.e., the high-frequency current), the wire-cutter 20 is heated. The cutter 20 need not have a sharp edge for severing body tissues.

As has been indicated, the stapling member 5 curves by about 90° with respect to the axis of the insertion section 2. It can therefore easily catch the target tissues A, particularly in the case where the tissues A are located on the axis of the section 2. Further, the stapling member 5 can be directed to any desired direction since the insertion section 2 can freely rotate with respect to the operation section 1.

Figure 13:
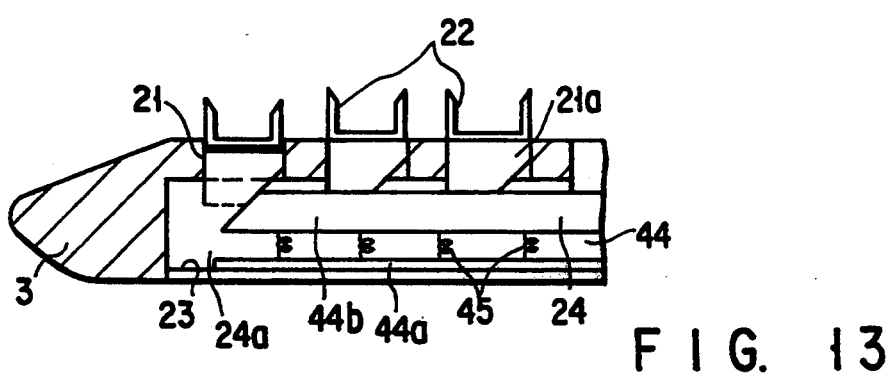
FIG. 13 is a sectional side view of the cartridge, illustrating modified pusher plates.
Figure 14:
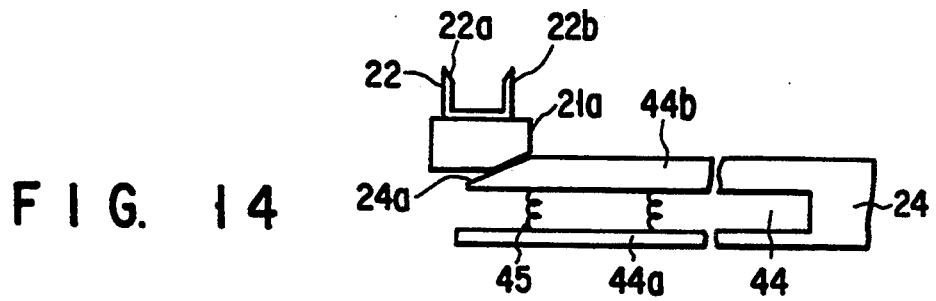
FIG. 14 is a side view of the modified pusher plates.
Figure 15:
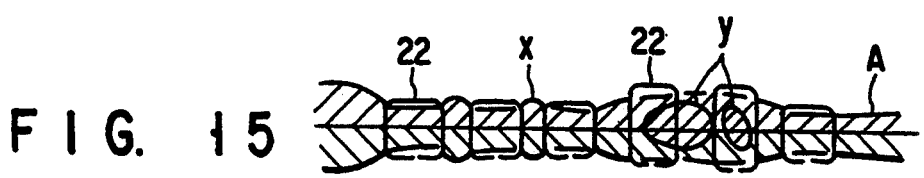
FIG. 15 is a sectional view showing the tissues stapled together by the stapler incorporating the modified pusher plates.

FIGS. 13, 14, and 15 show modified pusher plates 24. Each of the modified pusher plate 24 has a slit 44 which extends along its length and opening at its forward end. Hence, the slit 44 defines a lower strip 44a and an upper strip 44b. The lower strip 44a is in sliding contact with the bottom of the plate-guiding groove 23 formed in the cartridge 3. The upper edge of the upper strip 44b supports the pushers 21a. A number of compression coil springs 45 are interposed between the strips 44a and 44b, supporting the upper strip 44b such that the strip 44 can move up and down.

As the modified pusher plates 24 are moved forward along the plate-guiding grooves 23, they push the pushers 21a of each row, one after another. The pushers 21a push the staples 22 upward through the slits 21. The staples 22 are thereby driven into the target tissues A. The legs 22a and 22b of each staple 22 pierce the living tissues A, abut on the bottom of the groove 25 formed in the inner surface of the anvil 4, and have their tips bent inwardly. The tissues A are thereby stitched together with the staples 22 arranged in four parallel rows.

Any staple leg driven into a soft part x of the tissues A has a long bent tip, whereas any staple leg driven into a hard part y of the tissues A has a short bent tip—as is illustrated in FIG. 15. This is because the compression coil springs 45 are compressed more greatly when a staple 22 is driven into a hard part y, allowing the upper strip 44b to move downwards for a longer distance, than when a staple 22 is driven into a soft part x. Hence, any parts of the tissues A can be stitched together with the same clamping force, regardless of their hardness. This achieves neat and reliable stapling of living tissues.

Figure 16:
FIG. 16 is a side view showing another modified pusher plate.
Figure 17A:
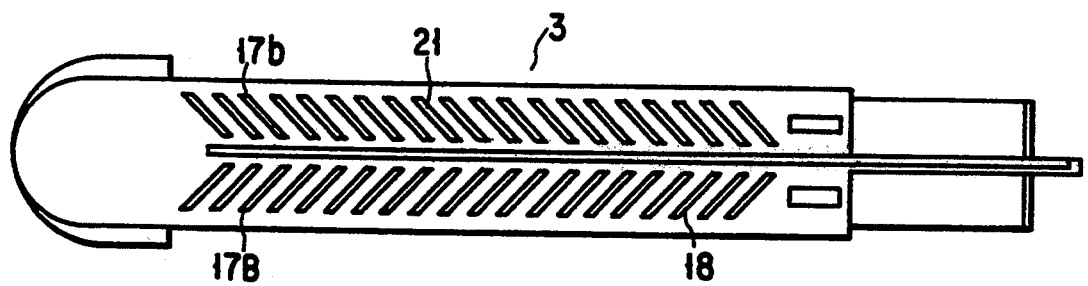
FIG. 17A is a plan view showing the cartridge of a modified stapling member.
Figure 17B:
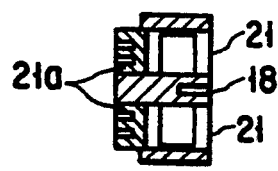
FIG. 17B is a cross-sectional view of the cartridge, taken along line 17B—17B in FIG. 17A.
Figure 17C:
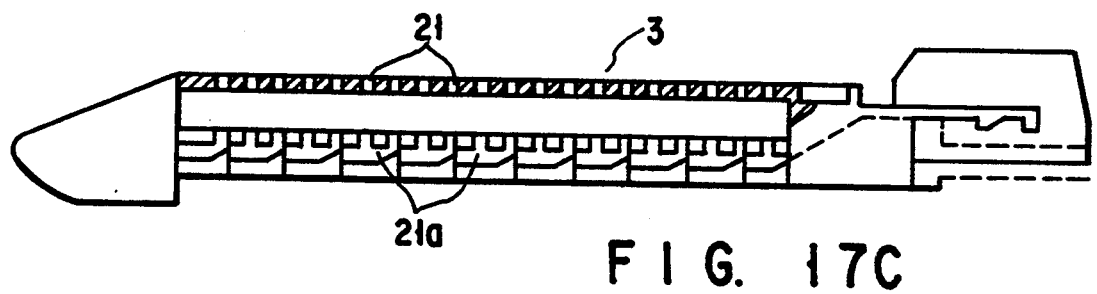
FIG. 17C is a partly cutaway side view of the cartridge.

FIG. 16 shows a modified pusher plates 24. This pusher plate 24 has a slit 46 cut in the distal end. The slit 46 inclines downward and toward the distal end and opening at the upper edge of the plate 24. Because of the slit 46, the distal end portion of the pusher plate 24 can plastically deformed when it abut on each pusher 21a. Hence, the modified pusher plate 24 has the same advantage as the modified pusher plates 24 shown in FIG. 14.

A modification of the stapling member 4 will be described with reference to FIGS. 17A, 17B and 17C, FIGS. 18A and 18B, FIG. 19, and FIGS. 20A and 20B.

The modified stapling member 5 has a cartridge 3 and an anvil 4. As is shown in FIGS. 17A to 17C and FIGS. 18A and 18B, the cartridge 3 is straight and has a cutter-guiding groove 18 and two rows of slits 21—all made in its upper surface. The groove 18 extends straight along the axis of the cartridge 3. The rows of slits 21 extend straight, parallel to the cutter-guiding groove 18, one row on one side of the groove 18 and the other row on the other side thereof. The slits 21 of each row are inclined to the groove 18 along which a wire-cutter (not show) is moved back and forth. Each slit 21 of one row laps at least partly with the corresponding slit 21 of the other row.

Figure 18A:
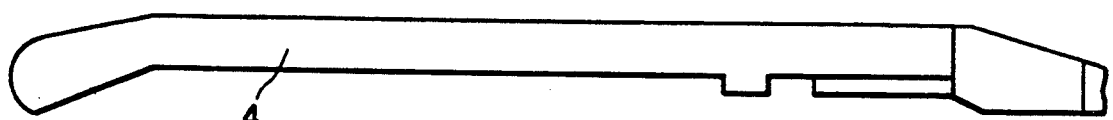
FIGS. 18A and 18B are a side view and plan view of the anvil of the modified stapling member.
Figure 18B:
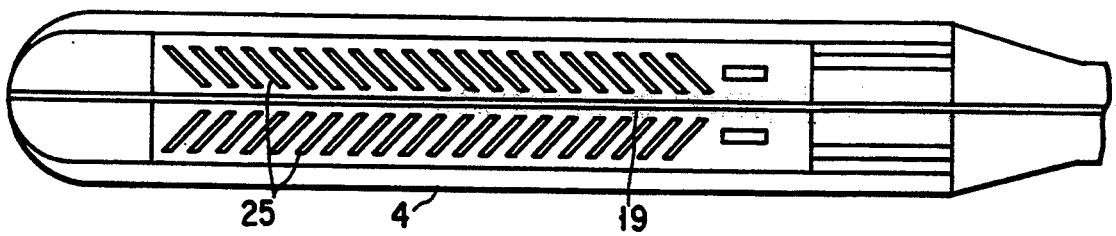
Figure 19:
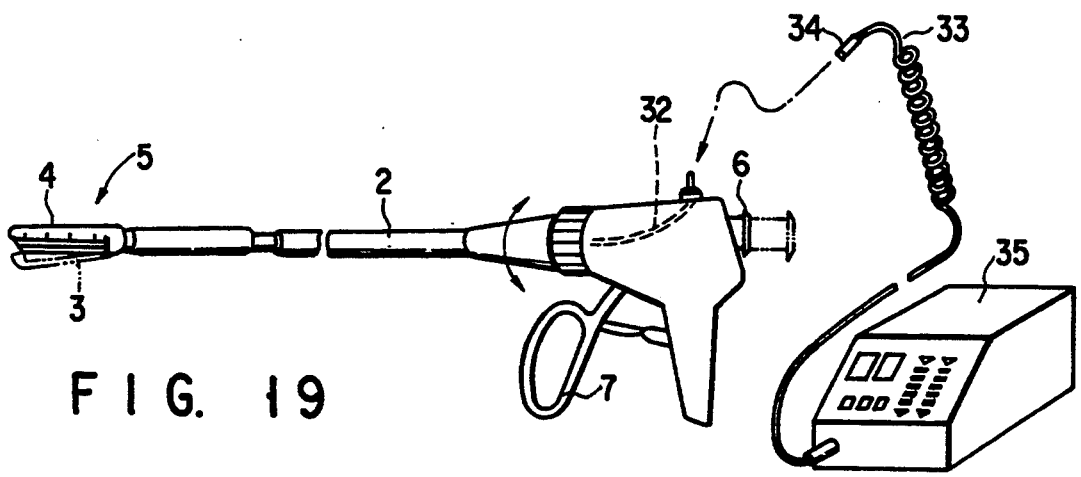
FIG. 19 is a perspective view of a stapler incorporating the modified stapling member.

As shown in FIG. 18B, the anvil 4 is straight and has a cutter-guiding groove 19 and two rows of grooves 25—all made in its upper surface. The groove 19 extends straight along the axis of the anvil 4. The rows of grooves 25 extend straight, parallel to the cutter-guiding groove 19, one row on one side of the groove 19 and the other row on the other side thereof. The grooves 25 of each row are inclined to the groove 1 along which a wire-cutter (not show) is moved back and forth. The grooves 25 are so located as to meet the corresponding slits 21 of the cartridge 3 when the cartridge 3 and the anvil 4 are closed together. Each of the grooves 25 has an arcuate bottom so that both legs 22a and 22b of a staple 22 may be bent inwards, or toward each other as the staple 22 is pushed against the bottom of the groove 25.

Figure 20A:
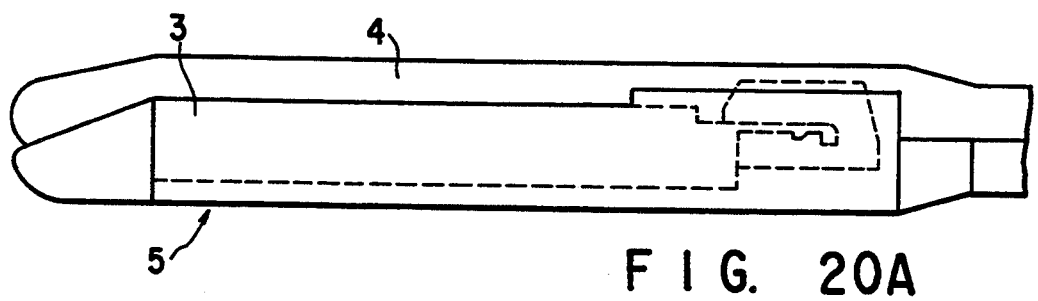
FIGS. 20A and 20B are a side view and front view showing the modified stapling member.
Figure 20B:

As shown in FIG. 20B, the inner surface of the cartridge 3, which opposes that of the anvil 4, is curved in the form of letter U, and the inner surface of the anvil 4 is rounded complementary to the U-curved inner surface of the cartridge 3. Further, the cartridge 3 and the anvil 4 have rounded outer surfaces of substantially the same curvature. Hence, the stapling member 5 has a circular cross section, while closed with the cartridge 3 and the anvil 4 placed in their closed positions. This helps to insert the stapling member 5 smoothly into a body cavity.

Figure 21:
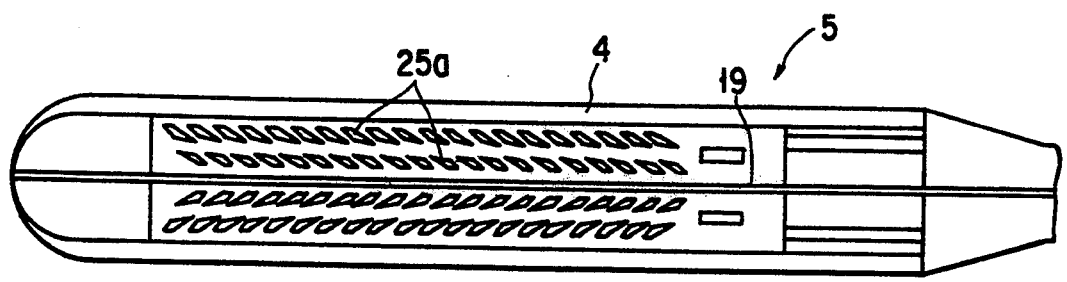
FIG. 21 is a plan view showing the anvil of another modification of the stapling member.
Figure 22:
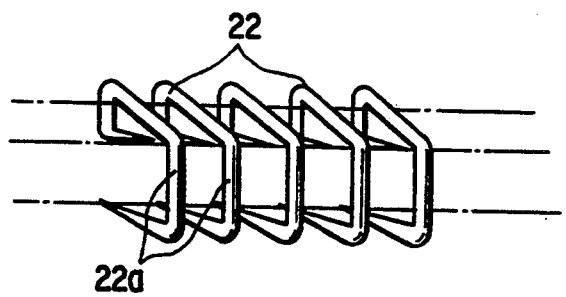
FIG. 22 is a perspective view showing staples applied by the stapling member shown in FIG. 21, stitching body tissues together.
Figure 23:
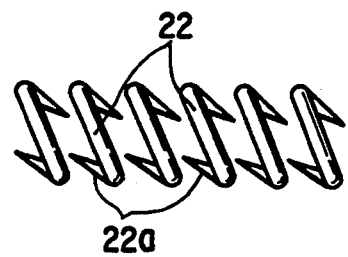
FIG. 23 is a plan view showing the staples applied by the stapling member shown in FIG. 21.

Another modification of the stapling member 5 will be described with reference to FIGS. 21, 22, and 23. This stapling member 5 is characterized in that the anvil 4 has in its inner surface two rows of grooves 25a on either side of the cutter-guiding groove 19, not one row of grooves 25a on either side of the groove 19 as in the stapling members 5 described above. Further, any corresponding two groove 25a of the rows are so directed and shaped that they serve to bent the legs 22a and 22b of a staple 22 toward each other but in staggered fashion as is illustrated in FIGS. 22 and 23.

More specifically, when each staple 21 is ejected from the cartridge 3, its legs 22a and 22b pierce body tissues and subsequently abut on the bottoms of the grooves 2. As a result, the tips of the legs 22a and 22b are bent toward each other, but in staggered fashion. With the leg tips thus bent, the staple 22 fastens the tissues so steadfastly that no body fluid such as blood or lymph will ooze out through the gaps between the staples 22.

Figure 24A:
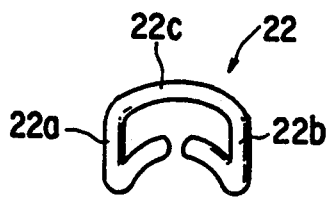
FIG. 24A is a perspective view showing a modified staple applied by a stapler according to the invention.
Figure 24B:
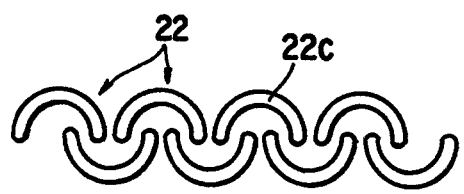
FIG. 24B is a plan view showing a row of staples identical to the staple shown in FIG. 24A.

FIGS. 24A and 24B show a modification of the staple 22. As shown in FIG. 24A, the modified staple 22 is characterized in that the head portion 22c connecting the legs 22a and 22b is arcuated in the plane perpendicular to the legs 22a and 22b, not straight as those of the staples described above. The tips of the legs 22a and 22b will be bent to curve in the same way as the head portion 22c when the staple 22 is applied by the stapler.

Stables 22 of this type are applied to body tissues, forming two rows as shown in FIG. 24B, such that the staples 22 of the first row are staggered by half pitch with respect to those of the second row, and that the head portion 22c of each staple 22 of one row surrounds the ends the head portions 22c of two adjacent staples 22 of the other row. Applied in this manner, the staples 22 stitch the body tissues firmly and reliably.

Figure 25A:
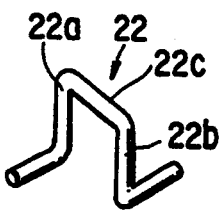
FIG. 25A is a perspective view showing another modified staple applied by a stapler according to the invention.
Figure 25B:
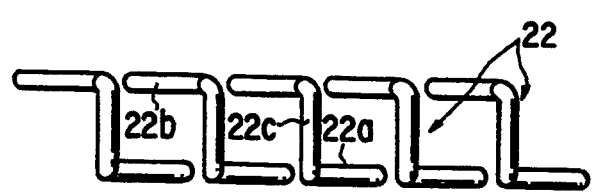
FIG. 25B is a plan view showing a row of the staples identical to the staple shown in FIG. 25A.

FIGS. 25A and 25B show another modification of the staple 22. As shown in FIG. 25A, this staple 22 consists of a straight head portion 22c and two straight legs 22a and 22b extending downward from the ends of the head portions 22c. The staple is characterized in that when it is applied, the tips of its legs 22a and 22b will be bent in the opposite directions as shown in FIG. 25A.

Stables 22 of the type shown in FIG. 25A are applied in the following way. The staples 22 are arranged in at least two rows on the sides of the cutter-guiding groove 18 of the cartridge 3, such that the head portions 22a of the staples 22 of each row extend at right angles to the groove 18 as is illustrated in FIG. 25B. Also, the staples 22 are arranged at such intervals that, when the legs 22a and 22b of each staple 22 are bent at their tips, the tips will lap the leg tips of the adjacent staples 22 as shown in FIG. 25B. The staples 22, thus arranged, are driven into body tissues, and the tips of their legs 22a and 22b are subsequently bent. Applied in this manner, the staples 22 stitch the body tissues firmly and reliably.

Figure 26A:
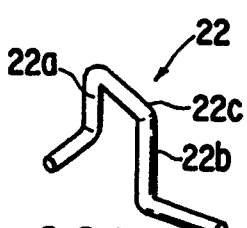
FIG. 26A is a perspective view showing still another modified staple applied by a stapler according to the invention.
Figure 26B:
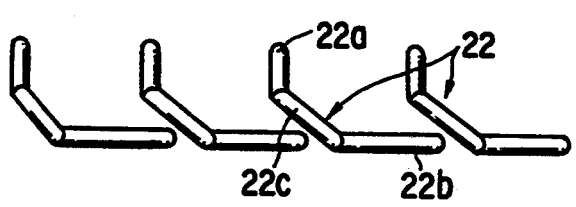
FIG. 26B is a plan view showing a row of the staples identical to the staple shown in FIG. 26A.

FIGS. 26A and 26B show still another modification of the staple 22. As shown in FIG. 26A, the staple 22 consists of a straight head portion 22c and two straight legs 22a and 22b extending downward from the ends of the head portions 22c. The staple is characterized in that when it is applied, the tips of its legs 22a and 22b will be bent at right angles to the remaining portions of the legs 22a and 22b and will be inclined to the head portion 22c at predetermined angles other than 90° in the opposite directions as shown in FIG. 25B.

Stables 22 of the type shown in FIG. 26A are applied in the following way. The staples 22 are arranged in at least two rows on the sides of the cutter-guiding groove 18 of the cartridge 3, such that the head portions 22a of the staples 22 of each row incline to the groove 18 as is illustrated in FIG. 26B. Also, the staples 22 are arranged at such intervals that, when the legs 22a and 22b of each staple 22 are bent at their tips, one of the tips will lap the head portion 22c of the next staple 22 as shown in FIG. 26B. The staples 22, thus arranged, are driven into body tissues, and the tips of their legs 22a and 22b are subsequently bent as shown in FIG. 26A. Applied in this manner, the staples 22 stitch the body tissues firmly and reliably.

Figure 28B:
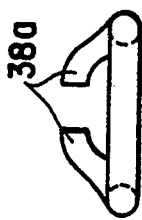
FIG. 28B is a plan view of a staple with its tips bent along the groove.
Figure 28A:
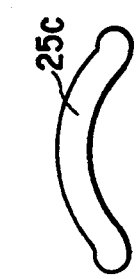
FIG. 28A is a plan view of one of identical grooves formed in the inner surface of an anvil, each for bending the tips of a staple.
Figure 27B:
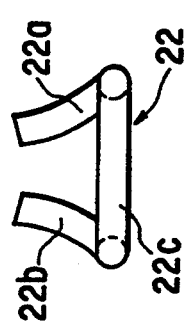
FIG. 27B is a plan view of a staple with its tips bent along the groove.
Figure 27A:
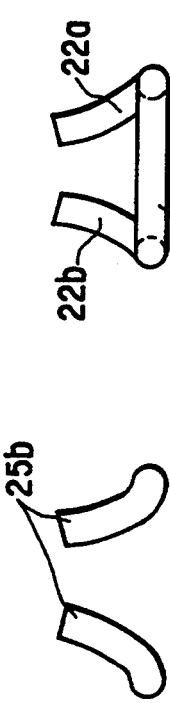
FIG. 27A is a plan view of one of identical grooves formed in the inner surface of an anvil, each for bending the tips of a staple.

FIGS. 27A and 28A are plan view of two types of grooves 25b and 25c, which are modifications of the grooves 25a described above.

The groove 24b shown in FIG. 27A consists of a pair of segment grooves which incline to each other. As the legs 22a and 22b of a substantially U-shaped staple 22 are pushed against the bottoms of these segment grooves, the tips of the legs 22a and 22b are bent, assuming the shapes identical to those of the segment grooves, as is illustrated in FIG. 27B.

The groove 25c shown in FIG. 28A is arching. As the legs 22a and 22b of a substantially U-shaped staple 22 are pushed against the bottom of the end portions of the groove 25c, the tips of the legs 22a and 22b are bent, each arching toward the other, as is illustrated in FIG. 28B.

A stapler according to a second embodiment of the present invention will be described with reference to FIGS. 29 to 34 and FIGS. 35A, 35B and 35C.

Figure 29:
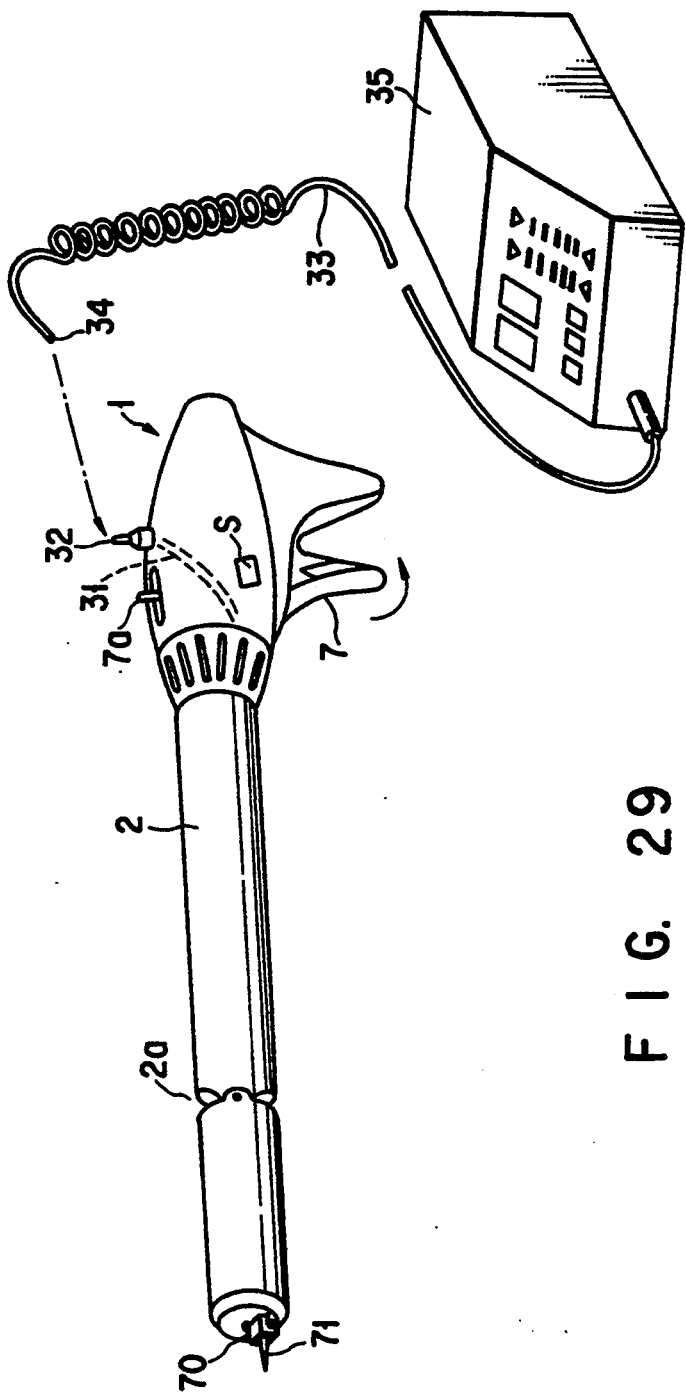
FIG. 29 is a perspective view of a stapler according to a second embodiment of the present invention.

As shown in FIG. 29, the stapler comprises an operation section 1, an insertion section 2, and a stapling section 2a connected to the distal end of the insertion section 2. The operation section 1 has a staple-driving handle 7 and a staple-bending lever 7a. The insertion section 2 is connected at its proximal end to the operation section 1, freely rotate around its axis. The stapling section 2a is coupled to the distal end of the insertion section 2.

The stapling section 2a contains a staple-ejecting member 70 and has a stylus 71 protruding from its distal-end face.

As sown in FIGS. 30, 31, and 32, the stapling section 2a of the insertion section 2, has a staple-holding groove 72 and an anvil-holding groove 73, both provided within the portion 2a and extending along the axis thereof. A staple track 74 rests in the staple-holding groove 72. The staple track 74 is a metal strip and has, at its distal end, an inclining portion 74a and a cam 75. As is best shown in FIG. 33, the cam 75 is connected to the portion 74a and has a channel-shaped cross section.

A staple-holding plate 76 is located above the staple track 74, spaced apart therefrom for a predetermined distance and extending substantially parallel to the staple track 74. Staples 22 are held between the gap of the staple track 74 and the staple-holding plate 76, arranged, end to end, in the lengthwise direction of section 2a. Each staple 22 is made of a thin wire bent in the form of A. The staples 22 are positioned with their legs directed to the distal end of the stapling section 2a and are biased toward the staple outlet 78a by a coil spring 77 which pushes the rearmost staple 22.

A staple pusher 79 is mounted on the staple-holding plate 76 and can slide back and forth through a passage 80. A horizontal groove (not shown) is formed in the distal-end face of the staple pusher 79, which serves as a staple-pushing member 79a. The staple pusher 79 has a projection 79b protruding from the upper surface. The projection 79b is connected to the staple-driving handle 7 incorporated in the operation section 1. Hence, as the handle 7 is rotated, the staple 79 slides through the stapling section 2a, back and forth between the staple outlet 78a and the staple-pushing member 79a.

An anvil 81 is located in the anvil-holding groove 73 and can move back and forth. The anvil 81 has a slit 81a in the middle portion and a projection 81b protruding from the upper surface. The projection 81b is inserted in a groove 73a formed in the bottom of the anvil-holding groove 73. Hence, the anvil 81 can be moved but for a distance equal to the length of this groove the 73a. The projection 79b of the staple pusher is loosely inserted in the slit 81a.

A flange 81c extends downwards from the distal end of the anvil 81. The flange 81c abuts on the middle portion a staple 22, making it easy to bend the staple 22. The anvil 81 has a slit 81d located between the projection 81b and the flange 81c. A release spring 82 is inserted in the slit 81d. The front end of the spring 82 contacts the front of the slit 81d, and the rear end of the spring 82 is held in a hole made in the upper surface of the anvil 81. The middle portion of the spring 82 is bent, forming a V-shaped portion 82a which extends downwards through the slit 81d. The V-shaped portion 82a can accumulates a force strong ought to release each staple 22 from the flange 81c.

The staple-ejecting member 70 contained in the stapling section 2a has a staple-ejecting opening 70a and a staple-ejecting groove 70b communicating with the opening 70a, both formed in the distal-end face of the section 2a. The staple-ejecting groove 70b has a width for allowing the passage of the staples which have been deformed.

The stapling section 2a is rotatably coupled to the distal end 2c of the insertion section 2. To be more specific, the stapling section 2a is covered by a hollow cylindrical cover 85, the distal end 2c of the section 2 is covered by a hollow cylindrical cover 86. The cover 85 is hinged to the cover 86 by a hinge 87.

An operating wire 7a extends through the hollow cylindrical cover 86 and the hinge 87 and is connected at its rear end to the staple-bending lever 7a of the operation section 1. The distal end of the wire 7a is fastened to the hollow cylindrical cover 85. The hinge 87 contains a coil spring 88. The spring 88 connects the covers 85 and 86, end to end, biasing the insertion section 2 and the stapling section 2a in mutual axial alignment.

The proximal end portion 2b of the stapling section 2a has an axial through hole 89. The proximal end portion of the staple pusher 79 is slidably inserted in this hole 89 and has a large rear end. A compression spring 97 is located in the hole 89, loosely mounted on the proximal end portion of the staple pusher 79 and interposed between the large end of the pusher 79 and the front edge of the hole 89. The spring 97 therefore biases the staple pusher 79 toward the operation section 1.

Figure 34:
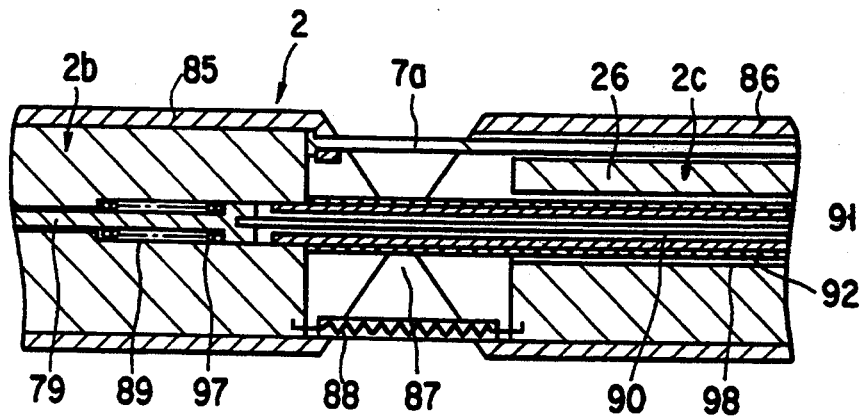
FIG. 34 is a sectional side view of the stapling section.

The insertion section 2 has an axial through hole 98. An operation wire 90 extends through this hole 98 and is connected at the rear end to the staple-driving handle 7, and at the front end to the proximal end of the staple pusher 79. As shown in FIG. 34, the wire 90 is wrapped with a coil sheath 92, which in turn is covered by an operating tube 92 made of soft material. The distal end portions of the sheath 91 and the tube 92 extend through the hinge 87 and coupled to the proximal end portion 2b of the stapling section 2a.

When the staple-bending lever 7a is rotated toward the proximal end of the operation section 1, the operating wire 7a is pulled in the same direction, rotating the hollow cylindrical cover 85, with the hinge 87 serving as fulcrum. Thus, the stapling section 2a is rotated with respect to the insertion section 2. When the lever 7a is released, the coil spring 88 contained in the hinge 87 rotates the cover 85 in the opposite direction, placing the same into the axial alignment with the hollow cylindrical cover 86. The stapling section 2a thereby resumes the axial alignment with the insertion section 2, whereby the sections 2 and 2a forms a straight unit.

A lock mechanism may be used to lock the staple-bending lever 7a in the pulled condition so that the stapling section 2a remains rotated or inclined with respect to the insertion section 2. Even while the section 2a is so rotated, the operation wire 90 can move the staple pusher 79 when the staple-driving handle 7 is squeezed, and the pusher 79 can deform the staple 22.

Referring back to FIG. 29, the operation section 1 contains an electric conductor 31 and has a connecting pin 32 protruding outwards. The pin 32 can be connected to the connector 34 fastened to an end of a cable 33 which is connected at the other end to a high-frequency cautery device 35. The conductor 31 extends from the pin 32 through the insertion section 2 and the stapling section 2a. As shown in FIG. 30, the conductor 31 is connected to the stylus 71 which protrudes from the distal-end face of the stapling section 2a. That portion of the stylus 71 which is embedded in the distal end of the section 2a is wrapped with an insulator 71b such as a rubber tube and is therefore electrically insulated from the stapling section 2a.

The stapler shown in FIG. 29 is manipulated to apply staples 22 in the following manner, to stitch body tissues together.

When the staple-driving handle 7 is squeezed in the direction of arrow β shown in FIG. 1, pushing the operating wire 90 forward. The staple pusher 79 connected to the staple pusher 79 is moved forward. The staple-pushing member 79a of the pusher 79 abuts on the arching end portions of the staple 22, pushing the staple 22 forward. The staple 22 pushes the rear half of the V-shaped portion 82a of the release spring 82. The spring 82 is thereby thrust forward. The anvil 81, which holds the spring 82 in its slit 81d, is subsequently moved forward, too.

The anvil 81 stops moving the moment the projection 81b abuts on the front edge of the groove 73a formed in the bottom of the anvil-holding groove 73. By contrast, the staple pusher 79 and the staple 22 are further moved forward. When released from the middle portion of the staple 22, the release spring 82 pushed upwards, making the staple 22 move to a position in front of the spring 82. At this time, the middle portion of the staple 22 abuts on the flange 81c which extends downwards from the distal end of the anvil 81.

As the staple pusher 79 is further moved forward, the staple 22 is clamped between the staple-pushing member 79a and the flange 81c and is eventually deformed or closed. More specifically, the projections of the member 79a push the arching end portions of the staple 22, while the flange 81c holds the middle portion of the staple 22. Hence, the end portions of the staple 22 are bent forward until they abut on each other. Meanwhile, the V-shaped portion of the spring 82 is kept compressed by the staple-pushing member 79a, spring 82 accumulates force. At this time, the handle 7 can no longer be squeezed further. When the handle 7 is released, the operating wire 90 is pulled toward the operation section 1, moving the staple pusher 79 backward. Then, the release spring 82 exerts the accumulated force on the closed staple 22, whereby the staple 22 is released from the flange 81c and subsequently ejected from the stapling section 2a, passing through the staple-ejecting groove 70b which is formed in the distal-end face of the section 2a.

As the staple pusher 79 is moved toward the operating section 1 after the staple 22 has been deformed, the projection 79b of the staple pusher 79 abuts on the read end of the slit 81a of the anvil 81. The anvil 81 is, therefore, moved toward the operation section 1, too. Both the staple pusher 79 and the anvil 81 are moved until the projection 81b of the anvil 81 abuts on the rear edge of the groove 73a. When the staple pusher 79 and the anvil 81 are stopped, the staple outlet 78a is no longer covered by the pusher 79. Now that the staple outlet 78a is opened, the next staple 22 is pushed toward the distal end of the staple pusher 79, by virtue of the spring force of the staple track 74.

The distal end of the staple track 74 closes the staple-holding groove 72 and the staple outlet 78a. Thus, the next staple 22 is prevented from moving outward through the outlet 78a. At the time the staple pusher 79 passes over the outlet 78a, the lower surface of the pusher 79 contacts the cam 75 which is integral with the staple track 74. Thereafter, the distal end portion of the staple track 74 is pushed back into the staple-holding groove 72, and the next staple 22 is moved to the distal end of the staple track 74.

Figures 35A, 35B, 35C:
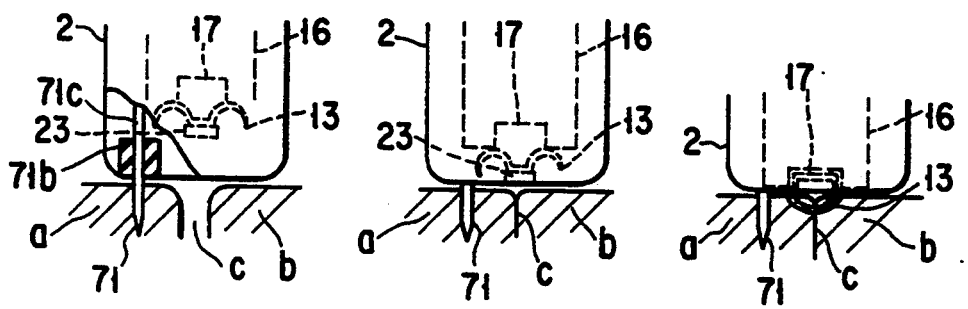
FIGS. 35A, 35B and 35C are diagrams explaining how the stapler applies staples to stitch body tissues together.
Figures 36A, 36B:
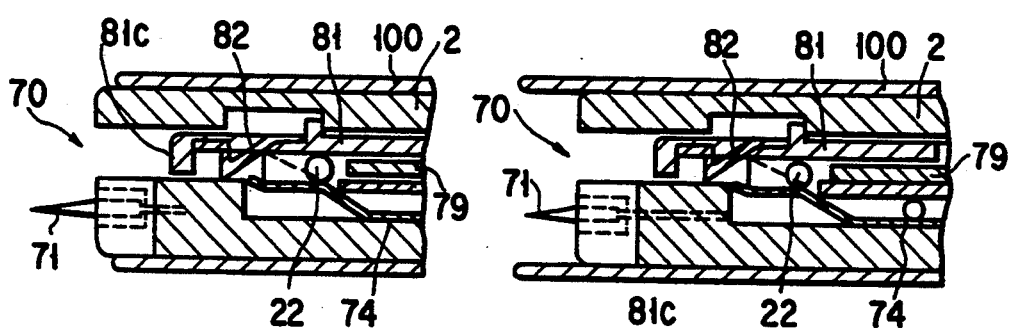
FIGS. 36A and 36B are sectional side views of the distal end portion of a modification of the stapler according to the second embodiment, FIG. 36A showing the hollow cylindrical cover pulled to its retreated position, and FIG. 36B showing the cover thrust to its forward position.

With reference to FIGS. 35A, 35B, and 35C, it will be described how the stapler shown in FIG. 29 is manipulated to stitch a wound c. First, as shown in FIG. 35A, the distal end of the stapling section 2a is placed on the tissues a and b on the sides of the wound c. As a result, the stylus 71 is driven into one of the tissues, for example tissue A. Then, as shown in FIG. 35B, the stapling section 2a is moved sideways, pulling the tissue a to the tissue b, thus closing the wound c. In this condition, the staple pusher 79 is moved for ward. The staple 22 is bent until their end portions pierce into the tissues A and b and finally abuts on each other at the closed wound c as illustrated in FIG. 35C. The wound c is thereby stitched.

Before driven into the tissue A, the stylus 71 is placed in touch with the tissue A. Then, a high-frequency current is supplied from the cautery device 35 to the stylus 71 via the cable 33, the connecting pin 32, and the conductor 31. The energized with this current, the stylus 71 generates heat. The heat is applied to a limited portion of the tissue A, thereby cauterizing this portion. Once cauterized, the tissue a becomes easy to pierce, allowing a smooth penetration of the stylus 71. Even if the stylus 71 pierces a blood vessel, if any in the cauterized portion, there will be no bleeding because the blood vessel has been cauterized.

The use of the stylus 71 enables a surgeon to stitch and close the wound c easily, with a single hand, while recognizing where the tissues a and b are located.

A modification of the stapler shown in FIG. 29, i.e., the second embodiment of the invention, will be described with reference to FIGS. 36A and 36B and FIGS. 37 and 38.

Figure 37:
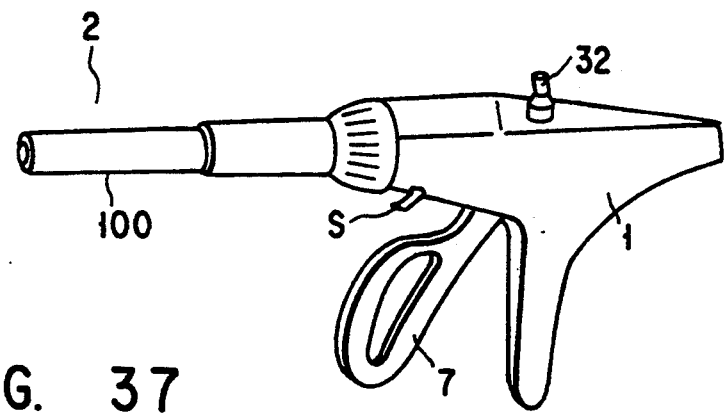
FIG. 37 is a perspective view showing the modification of the stapler.

As shown in FIG. 37, a hollow cylindrical cover 100 covers almost the entire length of an insertion section 2. The cover 100 can be slid along the axis of the insertion section 2. When moved to a forward position, the cover 100 covers a stylus 71 protruding from the distal end of the section 2. The cover 100 is connected at its proximal end to the body 1a of an operation section 1 an can rotated around its axis.

Figure 38:
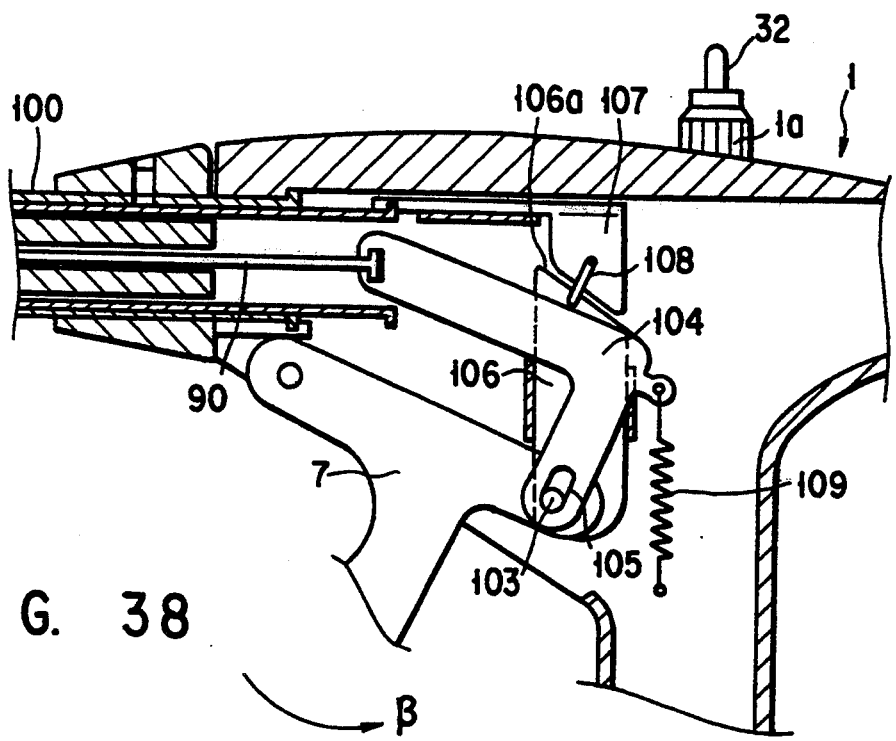
FIG. 38 is a sectional side view showing a part of the operation section of the modification of the stapler.

The operation section 1 has a staple-driving handle 7 which is rotatably coupled to the body 1a. As FIG. 38 shows, a pin 103 protrudes from the handle 7 and fitted in an elongated hinge hole 105 formed in one arm of an L-shaped pusher link 104. A sliding cam 106 is rotatably connected to the staple-driving handle 7. An L-shaped sliding member 107 is movably connected to the sliding cam 106 by a U-shaped pin 108. Am operating wire 90 is connected at the rear end to the other arm of the pusher link 104, and the forward end to a stapler pusher 79. The sliding member 107 is coupled to the hollow cylindrical cover 100. A spring 109 is connected to the pusher link 104, biasing the staple-driving handle 7 to rotate in the direction opposite to the direction of arrow β.

When the staple-driving handle 7 is squeezed in the direction of arrow β, the sliding cam 106 is moved up, pushing the sliding member 107 backward. The cover 100, which is connected to the sliding member 107, is thereby slid backward, exposing the stylus 71 protruding from the distal end of the insertion section 2. As the handle 7 is further squeezed in the direction of arrow β, the pusher ling 104 is rotated, pushing the staple pusher 79 forward. Thus pushed, the pusher 79 deforms a staple 22, stitching body tissues together.

Since the cover 100 covers the stylus 71 unless the staple-driving handle 7 is squeezed, there is no risk that the stylus 71 damages the tissues within a body cavity. A ratchet may be engaged with the handle 7 so that the handle 7 may be latched in a position to hold the cover 100 at its forward position.

Figure 39A:
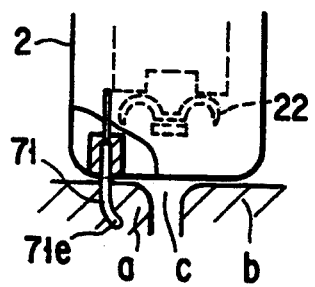
FIGS. 39A, 39B, and 39C are diagrams explaining how a modified stylus serves to stitch a wound.
Figure 39B:
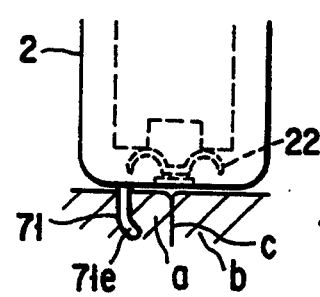
Figure 39C:
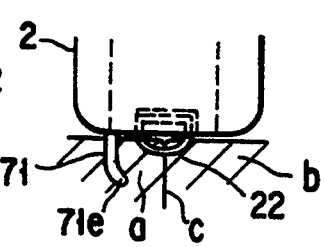

FIGS. 39A, 39B, and 39C show a modified stylus 71. As shown in FIG. 39A, this stylus 71 has a tip 71e which curves toward the axis of the insertion section 2. Due to the curving tip 71e, the stylus 71 helps to move the tissue a to the tissue b as shown in FIG. 39B. Hence, the wound c can be reliably closed and stitched with staple 22 as is illustrated in FIG. 39C.

Figure 40A:
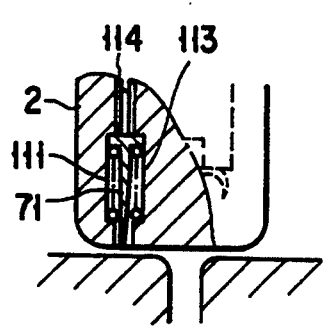
FIGS. 40A and 40B are diagrams explaining how a modified stylus is used.
Figure 40B:
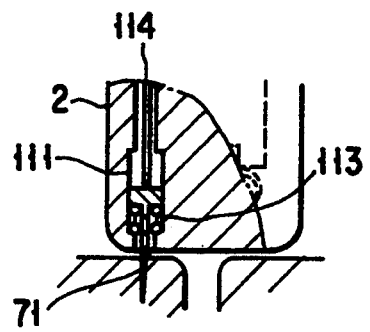

FIGS. 40A and 40B show the distal-end portion of a modified insertion section 2. As shown in these figures, a bore 111 is formed in the distal-end portion of the section 2. A stylus 71 is contained in this bore 111 and biased by a spring 113 to move away from the distal-end face of the section 2. The rear end of the stylus 71 is connected to a rod 114 which extends through the insertion section 2 and connected to the operation section 1. Hence, when the rod 114 is thrust forward, the stylus is pushed out of the hole 111 against the force of the spring 113. The stylus 71 remains in the bore 111 unless pushed by the rod 114, and would not damage tissues within a body cavity.

Figure 41:
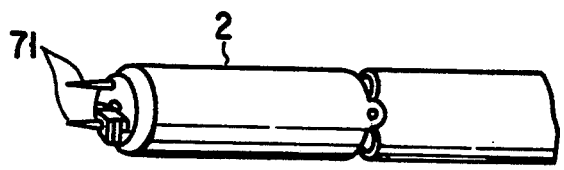
FIG. 41 is a perspective view of a modified insertion section having two styluses protruding from the distal-end face.

FIG. 41 illustrates a modification of the insertion section 2. The modified section 2 is characterized by two styluses 71 which protrude from the distal-end face of the section 2, extending parallel to each other. Once driven into a tissue at positions on one side of a wound, the styluses 71 serve to close the wound more neatly than is possible with a single stylus. If necessary and possible, three or more styluses may be fastened to the distal-end face of the section 2 to accomplish neat wound-closing and wound-stitching.

Figure 42A:
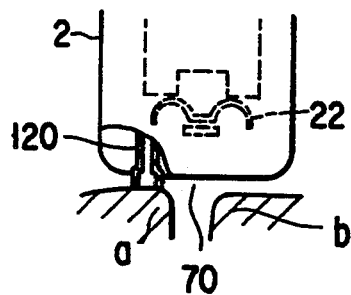
FIGS. 42A, 42B, and 42C are diagrams showing another modified insertion section having a suction tube, and explaining how the tube is used to close a wound.
Figure 42B:
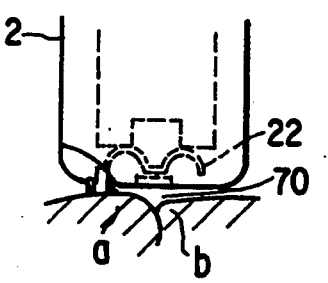
Figure 42C:
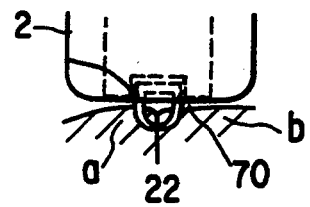

FIGS. 42A, 42B, and 42C show another modification of the insertion section 2. This modified section 2 is characterized in that a suction tube 120 is used in place of the stylus 71. The tube 120 is located near the staple-ejecting member 70 and is connected to a vacuum pump or the like (not shown). The insertion section 2 is moved until the suction tube 120 touches a tissue a. The vacuum pump or the like is driven, whereby the section 2 holds the tissue a. The section 2 is moved sideways, bringing the tissue a into contact with the tissue b and thus closing the wound c. Then, a staple 22 is driven into the tissues a and b, thereby stitching the wound c. With this modified insertion section 2 it is easy to find the wound c (or an incision), improving the operability of the stapler.

Figure 43A:
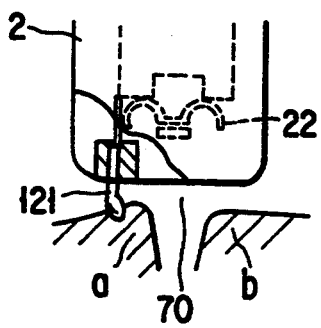
FIGS. 43A, 43B, and 43C are diagrams showing still another modified insertion section having a scoop-like member protruding from the distal-end face, and explaining how the scoop-shaped member is used to close a wound.
Figure 43B:
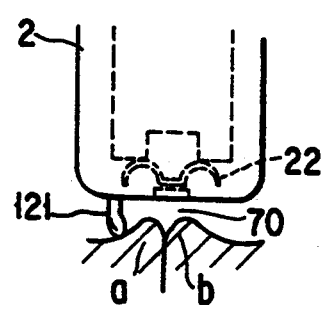
Figure 43C:
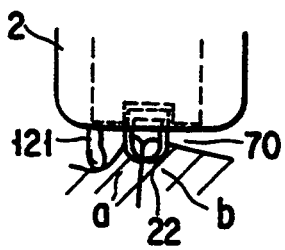
Figure 44:
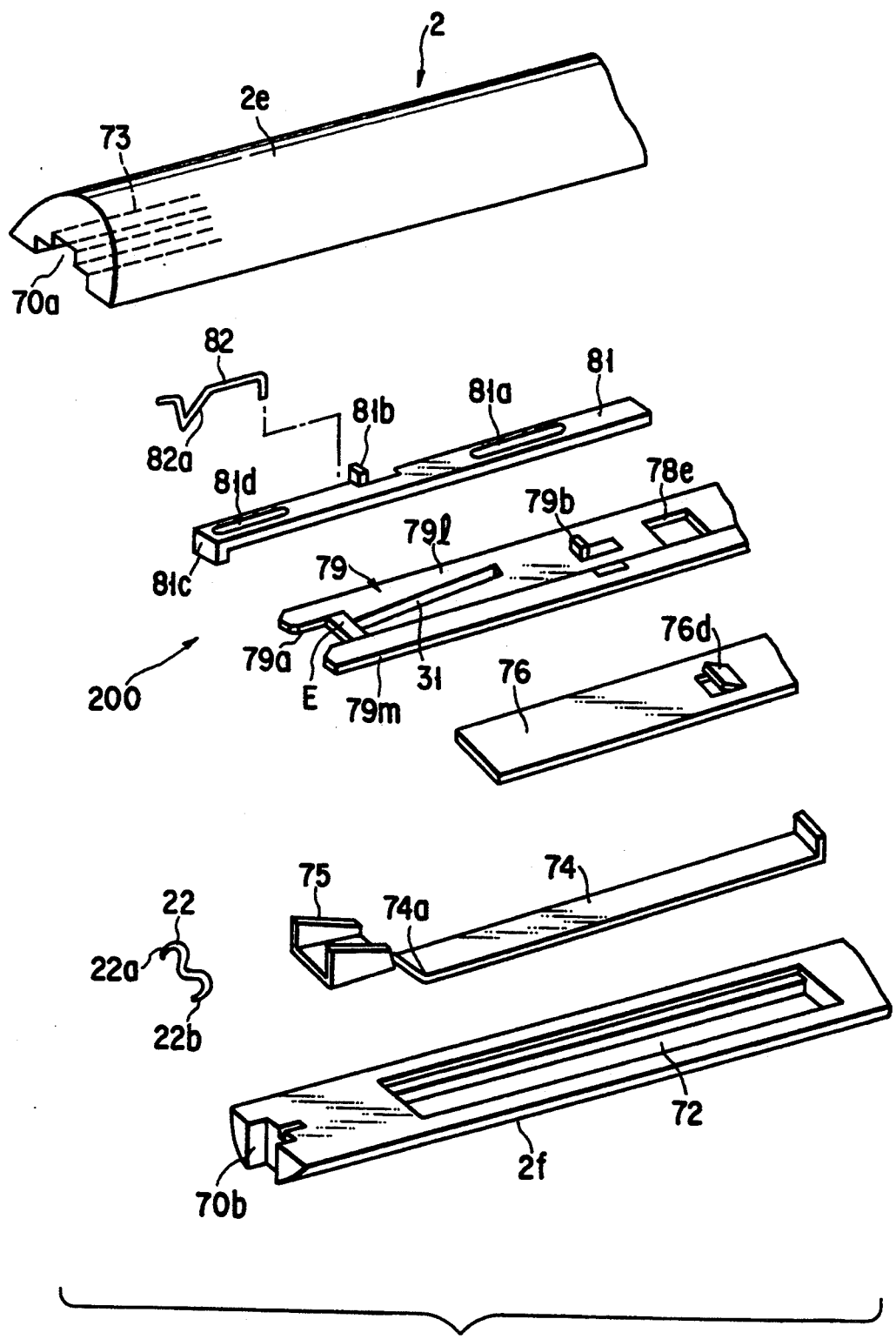
FIG. 44 is an exploded view of the insertion section of a stapler according to a third embodiment of the present invention.

FIGS. 43A, 43B, and 43C show another modification of the insertion section 2. This modified section 2 is characterized in that a scoop-shaped member 121 protrudes from the distal-end face and is located near the staple-ejecting member 70. The insertion section 2 is moved until the member 121 catches a tissue a. The section 2 is then moved sideways, whereby the member 121 brings the tissue a into contact with the tissue b and thus closing the wound c. Then, a staple 22 is driven into the tissues A and b, thereby stitching the wound c. Since the scoop-shaped member 121 is slender, it does not hide the wound c. Nor does it damage the tissues since its tip is rounded. The member 121 may assume any other shape, provided that it can easily take hold of a tissue.

A stapler according to a third embodiment of the invention will be described, with reference FIG. 44, FIGS. 45A, 45B and 45C, FIG. 46, FIG. 47, FIGS. 48A and 48B, FIGS. 49A, 49B and 49C, and FIG. 50.

FIGS. 44 and FIGS. 45A, 45B and 45C show a stapling mechanism incorporated in the distal end portion of an insertion section 2. The section 2 comprises an upper cover 2e and a lower cover 2f. The upper cover 2e has a staple-ejecting opening 70a at its end face. The lower cover 2f has a staple-ejecting groove 70b formed in its end face. The lower cover 2f has a staple-holding groove 72 formed in its inner surface, and the upper cover 2e has an anvil-holding groove 73 formed in its inner surface. A staple track 74 rests in the staple-holding groove 72. The staple track 74 is a metal strip and has, at its distal end, an inclining portion 74a and a cam 75.

A staple-holding plate 76 is located above the staple track 74. The plate 76 has a claw 76d which prevents a forward movement of the plate 76. Staples 22 are held between the gap of the staple track 74 and the staple-holding plate 76, arranged, end to end, in the lengthwise direction of the insertion section 2. Each staple 22 is made of a thin wire bent in the form of $\omega$. The staples 22 are positioned with their legs directed to the distal end of the insertion section 2 and are biased toward the staple outlet 78a by a coil spring 77 which is held in the staple-holding groove 72 and which pushes the rearmost staple 22.

Figure 50:
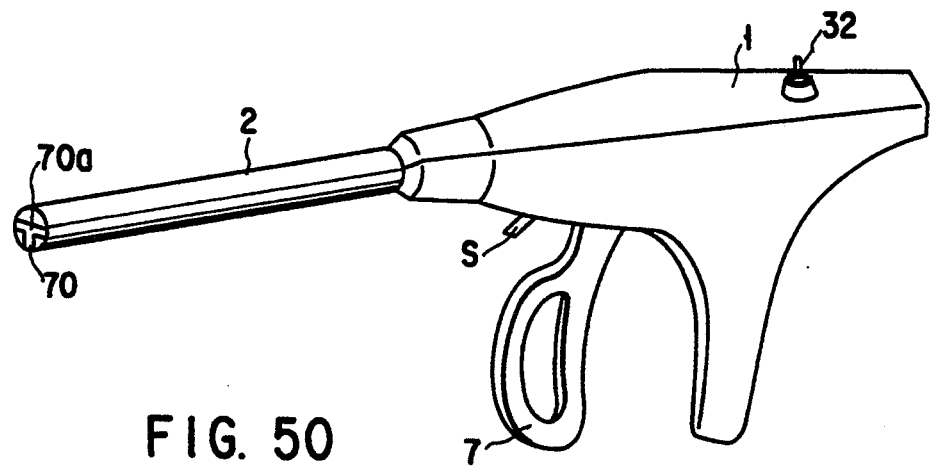
FIG. 50 is a perspective view of the stapler according to the third embodiment of the invention.

Mounted on the staple-holding plate 76 are a right staple pusher 79l and a left staple pusher 79m which extend along the axis of the section 2, parallel to each other. The pushers 79l and 79m can move back and forth into and out of the staple outlet 78a, and constitute a staple pusher 79. The right staple pusher 79l has a cutout at its distal end. Because of this cutout, the distal end portions of the pushers 79l and 79m define a U-notch 79a. An electrode E is mounted on the distal end of the staple pusher 79. An electric conductor 31 is connected at the forward end to the electrode E and at the rear end to a connecting pin 32 which protrudes from an operation section 1 as shown in FIG. 50. The electrode E is connected to the staple pusher 79 in the case where the pusher 79 is made of insulating material such as synthetic resin, or connected to an insulating coating or an insulator covering the pusher 79 in the case where the pusher 79 is made of electrically conductive material such as metal. The distal end of the electrode E extends into the U-shaped notch 79a and is exposed therein. Hence, the electrode E can contact a staple 22 at least while the staple 22 remains in the distal end of the insertion section 2 immediately before it is deformed.

The right staple pusher 79l has a projection 79b and a hole 78e. Inserted in the hole 78e is the claw 76d of the staple-holding plate 76. Both the right staple pusher 79l and the left staple pusher 79m are biased backward by a return spring 130 which is contained in the distal end portion of the operation section 1. The pushers 79l and 79m are coupled to a staple-driving handle 7 by a connecting means (later described). As the handle 7 is operated, the pushers 79l and 79m can move back and forth between the staple outlet 78a and a staple-forming section 78b.

An anvil 81 is located above the right right staple pusher 79l and inserted in the anvil-holding groove 73. The anvil 81 can move back and forth. The anvil 81 has a slit 81a and a projection 81b. In the slit 81a, the projection 79b of the right staple pusher 79l is fitted. The projection 81b protrudes from the upper surface and inserted in a groove 73a formed in the bottom of the anvil-holding groove 73. The groove 73a prevents an excessive movement of the anvil 81.

A flange 81c extends downwards from the distal end of the anvil 81. The flange 81c abuts on the middle portion a staple 22, making it easy to bend the staple 22. The anvil 81 has a slit 81d located between the projection 81b and the flange 81c. A release spring 82 is inserted in the slit 81d. The middle portion of the spring 82 is bent, forming a V-shaped portion 82a which extends downwards through the slit 81d. The V-shaped portion 82a can accumulates a force strong enough to release each staple 22 from the flange 81c.

FIGS. 46 and 47 and FIGS. 48A and 48B show the operation section 1. As is shown in FIG. 46, the staple-driving handle 7 is rotatably coupled to the frame 1a of the section 1 by a pivot pin 132 and is biased by a spring 133 to rotate in the direction opposite to arrow $\beta$.

A hollow cylindrical pusher 135 is coupled to the upper end of the handle 7 by a connecting pin 134. The pusher 135 can therefore be moved back and forth as the handle 7 is rotated. The pusher 135 has four continuous cam surfaces 135a formed on the distal-end face and arranged in the circumferential direction of the pusher 135. A hollow cylindrical switching member 137 is located in front of the pusher 135 and can move back and forth. The member 137 has a round cam surface 137a at its distal end. This cam surface 137a opposes the cam surfaces 135a of the pusher 135.

The switching member 137 is biased toward the operation section 1 by a bias spring 136. The member 137 has elongated guides 139 formed on the outer circumference of the member and spaced at regular intervals in the circumferential direction. The guides 139 have a cam surface 139a each at the end and are set in sliding engagement with grooves 138 formed in the inner surface of the frame 1a, respectively. Each groove 138 extends along the axis of the operation section 1 and is defined by a pair of parallel strips 138b which protrudes from the inner surface of the frame 1a. A hollow cylindrical outer pusher 140 protrudes from the distal-end face of the switching member 137. Four inner pushers 141 protrude from the distal-end face of the member 137, too, and extend through the outer pusher 140 as is shown in FIG. 48. The inner pushers 141 are parallel to one another and spaced apart by angular distance of 90°.

Both the hollow cylindrical pusher 135 and the switching member 137 are prevented from rotating around their axes by means of the grooves 138 formed in the inner surface of the frame 1a. While the pusher 135 is supported in the grooves 138, its cam surfaces 135a abut on the cam surface 137a of the switching member 137, displaced by ¼ pitch with respect to the cam surface 1237a.

When the staple-driving handle 7 is squeezed in the direction of arrow $\beta$ against the force of the spring 133, the pusher 135 is moved forward, pushing the switching member 137 in the same direction. When the member 137 reaches a position where the grooves 138 are not located, the pusher 135 is rotated until its cam surfaces 135a are aligned with the cam surface 137a of the switching member 137, eliminating the ¼-pitch displacement with respect to the cam surface 1237a.

As the handle 7 is further squeezed in the direction of arrow $\beta$, the switching member 137 is biased backward by the bias spring 136. The cam surfaces 139a of the guides 139 thereby abut on the cam surface 138a formed in the grooves 138, whereby the switching member 137 is rotated by 90°, making each guide 139 slide into the next groove 138. Thus, the member 137 is intermittently rotated as the handle 7 is squeezed, each time through an angle of 90°.

The rear end portion of the right staple pusher 79l is located outside the axis of the operation section 1, whereas the rear end portion of the left staple pusher 79m is located inside the axis of the operation section 1. As described above, the switching member 137 is intermittently rotated, each time by 90°, as the handle 7 is squeezed. Hence, the outer pusher 140 and one of the inner pusher 141 alternately abuts on the rear end of the staple pusher 79.

It will now be described how the stapler shown in FIG. 46 is manipulated to stitch body tissues together.

Figure 45A:
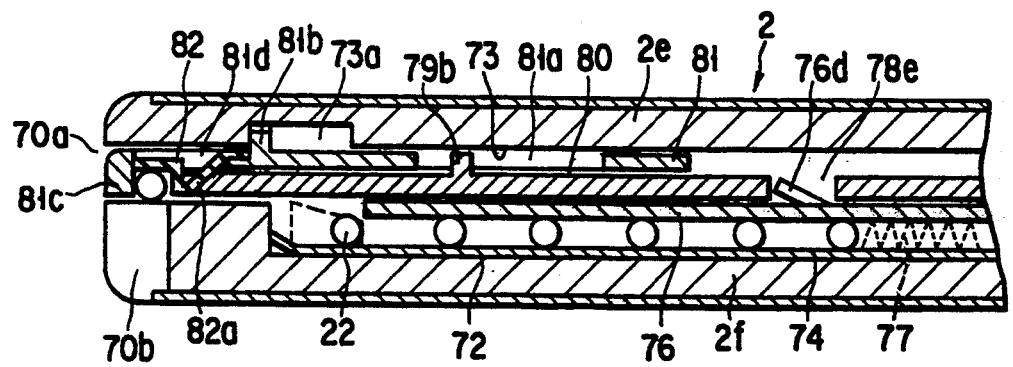
FIG. 45A is a sectional side view of the insertion section, showing how the stapler is operated to deform a staple.
Figure 45B:
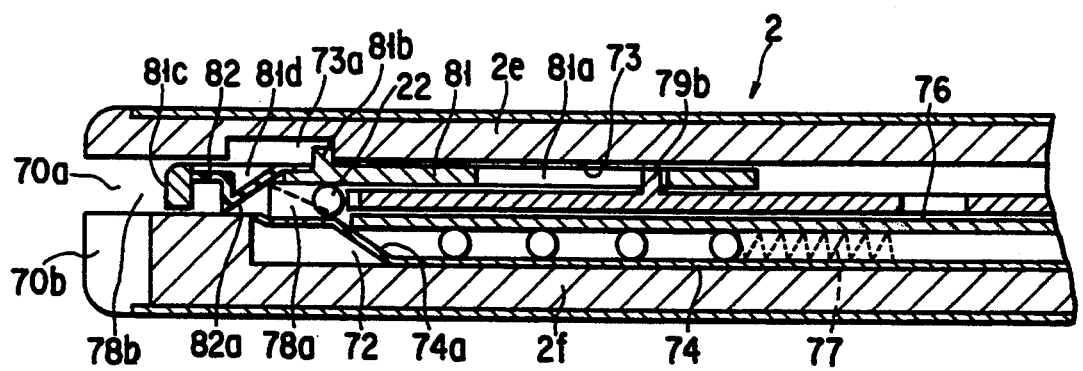
FIG. 45B is a sectional side view of the insertion section, showing how the stapler is operated to load staples.
Figure 45C:
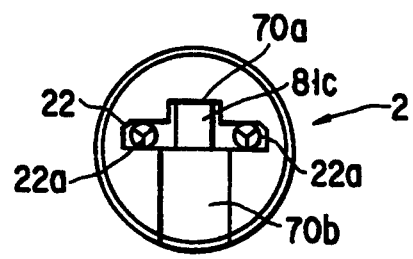
FIG. 45C is a front view of the insertion section.

FIGS. 45B and 45C show the insertion section 2 and explain how staples 22 are loaded in the section 2. When the staple-driving handle 7 is squeezed, the pusher 135 is moved forward, pushing the switching member 137 in the same direction. The outer pusher 140 pushes the right staple pusher 791 toward the distal end of the insertion section 2.

In the staple outlet 78a, a staple 22, which has been pushed up from the front end of the staple track 74, is pressed onto the V-shaped portion 82a of the release spring 82. At this time both the anvil 81 and the release spring 82 connected together. Hence, the anvil 81 is moved toward the distal end of the insertion section 2.

Thereafter, the projection 81b protruding from the upper surface of the anvil 81 abuts on the front edge of the groove 73a formed in the bottom of the anvil-holding groove 73. The anvil 81 is thereby stopped. The right staple pusher 791 and the staple 22 are further moved toward the distal end of the section 2. Then, the release spring 82 is pushed away from the middle portion of the staple 22, and the middle portion of the staple 22 abuts on the flange 81c.

As the right staple pusher 791 further moves toward the distal end of the section 2, it deforms the arcuate leg 22a of the staple 22. When the handle 7 is completely squeezed, it no longer exerts force to the right staple pusher 791. Although the return spring 130 biases the pusher 791 backward, the pusher 791 is held at the staple-deforming position by the claw 76d of the staple-holding plate 76.

When the staple-driving handle 7 is squeezed again in the direction of arrow β, the switching member 137 is rotated by 90° around its axis, whereby one of the inner pusher 141 abuts on the left staple pusher 79m, exerting a force on the pusher 79m. The left staple pusher 79m is moved forward, deforming the arcuate leg 22b of the staple 22.

While the pusher 79m is deforming the leg 22b of the staple 22, it is held at the staple-deforming position by the claw 76d of the staple-holding plate 76, whereas the right staple pusher 791 is released from the claw 76d. As the handle 7 is released, any force is no longer applied to the left staple pusher 79m. Thus, the release spring 82 pushes down the staple 22 now deformed, whereby the staple 22 is ejected through a staple-ejecting groove 6. Both staple pushers 791 and 79m are moved backward to their initial positions.

During the staple-deforming process, a high-frequency current is supplied from a high-frequency cautery device (not shown) to the electrode E via the connecting pin 32 and the electric conductor 31. The current flows through the staple 22 which contacts the electrode E. Thus, the legs 22a and 22b of the staple 22 are readily deformed, stitching body tissues together.

After the staple 22 has been deformed, both staple pushers 791 and 89m move backward, returning to their initial positions, by virtue of the force of the return spring 130. The projection 79b of the right staple pusher 791 abuts on the rear edge of the slit 81a of the anvil 81, whereby the anvil 81 is moved backward, too. The pusher 791 and the anvil 81 are moved backward until the projection 81b of the anvil 8 contacts the rear edge of the groove 73a formed in the bottom of the anvil-holding groove 73. The time the pusher 791 and the anvil 81 are stopped, the staple outlet 78a is opened. Then, the next staple 22 is pushed up due to the spring force of the distal end portion of the staple track 74, and are located in front of both staple pushers 791 and 79m.

Figure 49A:
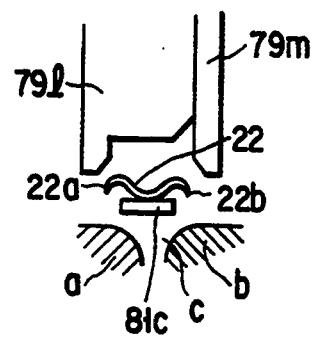
Figure 49B:
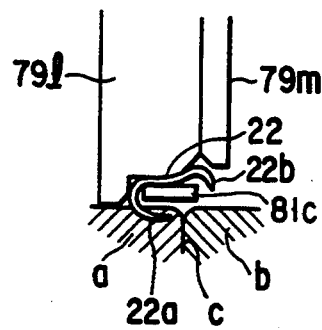
Figure 49C:
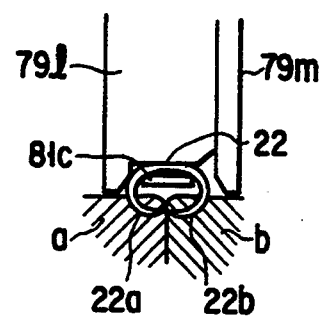

To apply a staple 22 to target tissues, the distal end of the insertion section 2 is moved, placing the staple-ejecting opening 70a at the gap between the tissues A and b, as is shown in FIG. 49A. Next, the staple-driving handle 7 is squeezed, pushing the right staple pusher 791 forward. Thus pushed, the pusher 791 bends the leg 22a of the staple 22 as shown in FIG. 49B, driving the leg 22a into the tissue a. Then, the insertion section 2 is moved sideways, pulling the tissue a into contact with the tissue a. Next, the handle 7 is squeezed again, thrusting the left staple pusher 79m forward. The pusher 79m bends the leg 22b of the staple 22, driving the same into the body tissue b, as is illustrated in FIG. 49C. As a result, the tissues are stapled together. The stapler enables a surgeon to gather the tissues a and b, without using forceps. Since nothing protrude from the distal-end face of the section 2, the wound to be stapled can be seen well.

Figure 51:
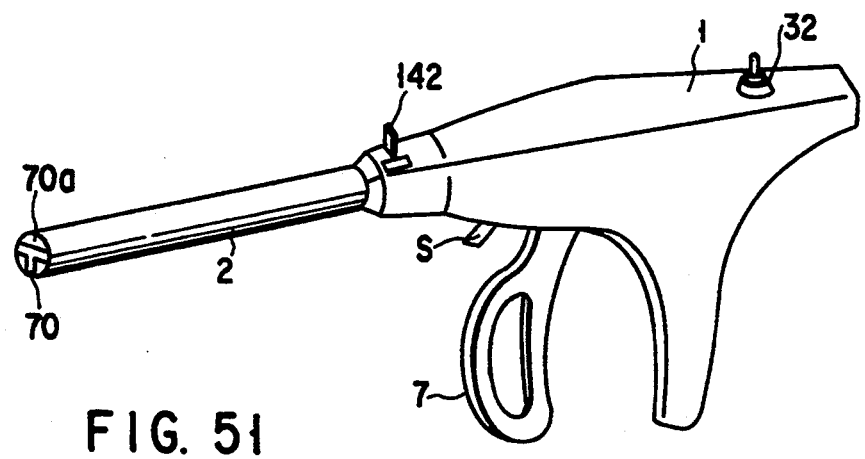
FIG. 51 is a perspective view showing a modification of the stapler according to the third embodiment of the invention.

A modification of the stapler shown in FIG. 46 will be described, with reference to FIG. 51. As shown in FIG. 46, the modified stapler has a switching lever 142 rotatably connected to the operation section 1. The lever 142 is operated to switch the staple-deforming between two modes. The first mode is to deform the legs 22a and 22b of a staple 22 one after another, and the second mode is to deform the legs 22a and 22b at the same time. More precisely, when the lever 142 is operated, selecting the first mode, the staple pushers 791 and 79m are left separated; when the lever 142 is operated, selecting the second mode, the staple pushers 791 and 79m are coupled together. The first mode is preferable in the case the tissues a and b are spaced apart and one needs to be pulled into contact with the other. The second mode is desirable in the case where the tissues a and b contact each other.

A modification of the staple pusher 79 will be described with reference to FIG. 52 and FIGS. 53A to 53D. As FIG. 52 shows, the modified staple pusher 79 comprises three components, i.e., a right staple pusher 79g, a left staple pusher 79h, and a center staple pusher 79i. The pushers 79g and 79i are connected by a spring 114a, and the pushers 79g and 79h are connected by a spring 144b.

Figures 53A, 53B, 53C, 53D:
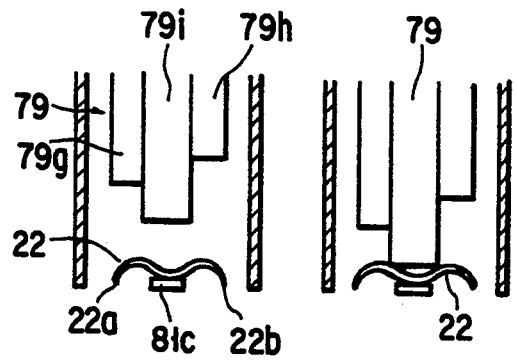
FIGS. 53A to 53D are diagrams explaining how the modified staple pusher of FIG. 52 deforms a staple to stitch body tissues together.

In operation, the center staple pusher 79i is moved forward as shown in FIG. 53A, until the pusher 79i and the flange 81c clamp the middle portion of a staple 22 as illustrated in FIG. 53B. Next, the right staple pusher 79g is pulled forward by the spring 144a, bending one leg 22a of the staple 22 as is shown in FIG. 53C. Finally, the left staple pusher 79h is pulled forward by the spring 114b, bending the other leg 22b of the staple 22 as is illustrated in FIG. 53D.

During this staple-deforming process, a high-frequency current is supplied from a high-frequency cautery device to the electrode E via the connecting pin 32 and the electric conductor 31. The current flows through the staple 22 which contacts the electrode E. Thus, the legs 22a and 22b of the staple 22 are readily deformed, stitching body tissues together.

Since the middle portion of the staple 22 is clamped between the flange 81c and the center staple pusher 79i, the legs of the staple 22 can be deformed more readily than otherwise, and the middle portion of the staple 22 can be deformed appropriately.

The three stages of deforming the staple 22, i.e., deforming the middle portion, the bending the left leg 22a, and the bending the right leg 22b, may be performed to predetermined degrees, by incorporating a ratchet mechanism in the operation section 1.

FIG. 54A and 54B show two modifications of the staple 22. This staple 22 consists of a middle portion 22c having a curving portion 22d, and two legs 22a and 22b which extend straight from the ends of the middle portion 22c. The portion 22d is curved in a plane perpendicular to the legs 22a and 22b.

Figures 55A, 55B, 55C, 55D:
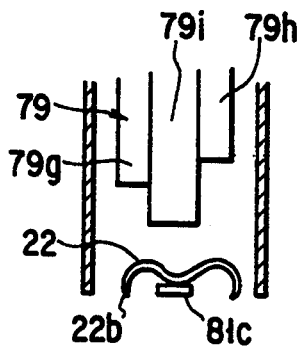
FIGS. 55A to 55D are diagrams explaining how the modified staple shown in FIGS. 54A, 54B is deformed to stitch body tissues together.
Figure 56:
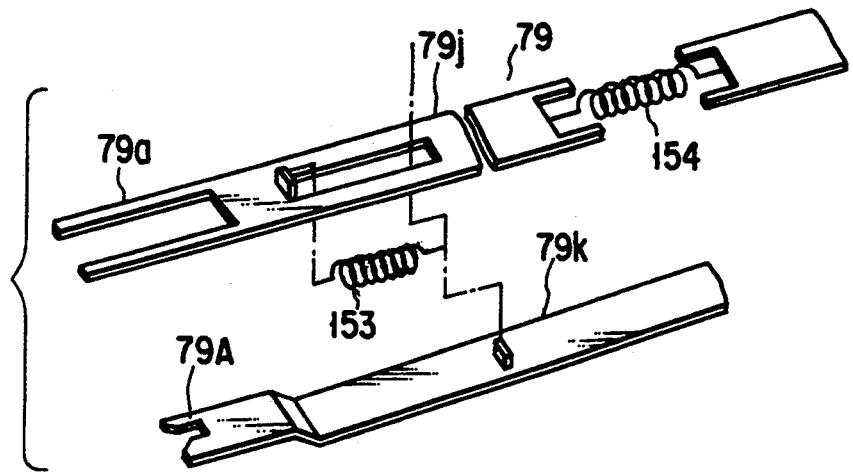
FIG. 56 is an exploded view showing another modified staple pusher.

The modified staple shown in FIGS. 54A and 54B is deformed in the following way by the staple pusher 79 of the type shown FIG. 52. First, the center staple pusher 79i is moved forward as shown in FIG. 55A, until the pusher 79i and the flange 81c clamp the portion 22d of a staple 22 as illustrated in FIG. 55B. Next, the right staple pusher 79g is pulled forward by the spring 144a, bending one leg 22a of the staple 22 as is shown in FIG. 55C. Finally, the left staple pusher 79h is pulled forward by the spring 114b, bending the other leg 22b of the staple 22 as is illustrated in FIG. 55D. Since the center staple pusher 79i fits in the curving portion 22d, the staple 22 is held in place steadfastly, making it easy to pull a first tissue to a second tissue after the leg 22a has been driven into the first tissue.

Another modification of the staple pusher 79 will be described with reference to FIG. 56 and FIGS. 57A, 57B and 57C. This modified pusher 79 comprises two staple pusher 79j and 79k which are located one above the other. The upper staple pusher 79j has a U-notch formed in the distal end. The lower staple pusher 79k has an elevated horizontal distal end portion is inserted in the U-notch of the upper pusher 79j. The pushers 79j and 79k can slide back and forth. A spring 153 biases the lower pusher 79k backward with respect to the upper pusher 79j. A spring 154 is connected to the rear end of the upper pusher 79j.

Figure 57A:
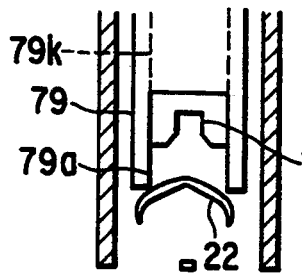
FIGS. 57A, 57B, and 57C are diagrams explaining how the modified staple of FIG. 56 deforms a staple to stitch body tissues together.
Figure 57B:
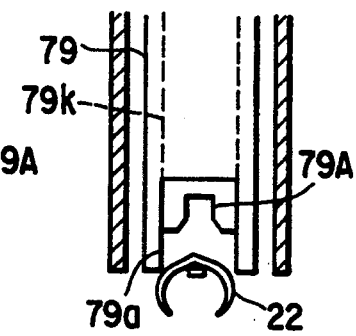

In operation, a force is applied from the operation section to the staple pushers 79j and 79k, moving them forward. First, the projections 79a of the upper pusher 79* abut on a staple 22 as shown in FIG. 57A. As the pushers 79* and 79k are further driven forward, the projections 78a bend the staple 22 as shown in FIG. 57B. Thereafter, only the lower staple pusher 79k is moved forward, whereby the distal end 79A of the lower staple pusher 79k bends the staple 22 further as illustrated in FIG. 57C.

Figure 57C:
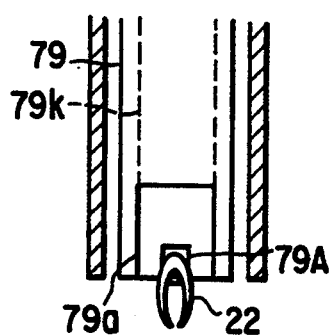

Therefore, the staple 22 can gather target tissues firmly as it is bent as shown in FIGS. 57B and 57C. Since the staple 22 is bent in two stages, first by the upper staple pusher 79j and then by the lower staple pusher 79k, the tissues can be gathered even if they are spaced apart for a relatively long distance. In other words, the staple pusher 79 shown in FIG. 56 can deform a staple 22 to stitch a wide-opening incision.

Figure 58:
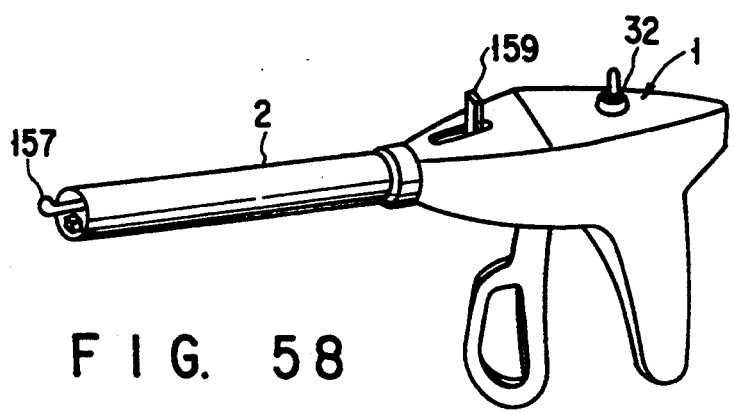
FIG. 58 is a perspective view of a modified stapler.
Figure 59A:
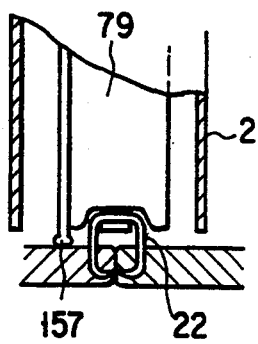
FIGS. 59A and 59B are diagrams explaining how the stapler of FIG. 58 applies a staple to fasten body tissues together.
Figure 59B:
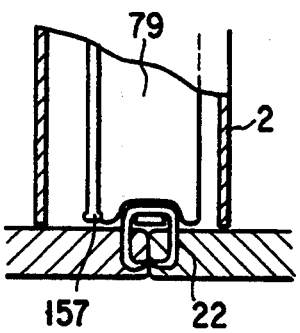

A modification of the stapler shown in FIG. 46 will be described with reference to FIG. 58 and FIGS. 59A and 59B. This modified stapler is characterized in two respects. First, a guide rod 157 extends through the insertion section 2 and protrudes from the distal end of the section 2. Second, a control lever 159 is rotatably connected to the operation section 1, to move the guide rod 157 back and forth to change the distance over which the rod 157 protrudes from the section 2.

If the body tissues to staple together are thick, the guide rod 157 is projected longer from the section 2. If the tissues are thin, the guide rod 157 is projected short from the section 2. The guide rod 157 and the lever 159 serve to staple living tissues of various thicknesses. A scale may be mounted on the guide rod 157 so that the distance between the tissues and the distal end of the insertion section 2 may be measured.

Figure 60A:
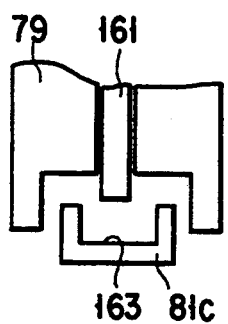
FIGS. 60A, 60B, and 60C are diagrams showing a modified staple pusher and explaining how the staple pusher deforms a staple in various forms.
Figure 60B:
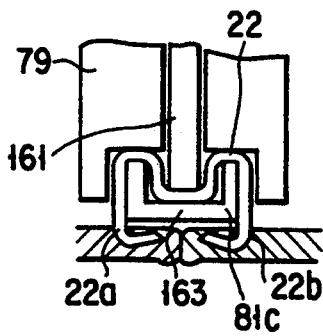
Figure 60C:
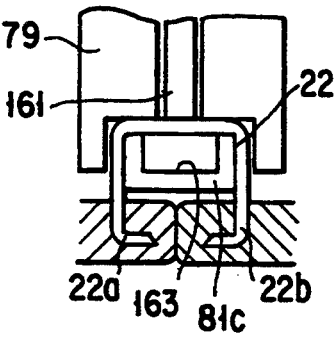

Still another modified staple pusher 79 will be described with reference to FIGS. 60A, 60B, and 60C. This modified staple pusher 79 is characterized in two respects. First, a member 161 is moved back and forth to change the form in which to bend a staple 22. Second, the flange 81c has a U-notch 163 opening to the member 161. By changing the distance by which the member 161 is thrust into the U-notch 163, the staple pusher 79 can bend the staple 22 bent in various shapes, thus adjusting the lengths of the legs 22a and 22b of the staple 22, as can be understood from FIGS. 60A, 60B, and 60C.

Figure 61:
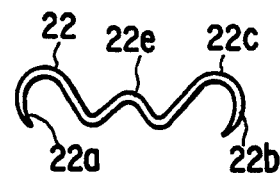
FIG. 61 is a perspective view of a modified staple.

With reference to FIG. 61, a modified staple 22 will be described. As shown in FIG. 61, the staple 22 consists of two legs 22a and 22b and a middle portion 22c connecting the legs 22a and 22b. Each leg has a sharp tip. The middle portion 22c has a section 22e bulging in the direction opposite to the direction in which the legs 22a and 22b extend.

Figure 62A:
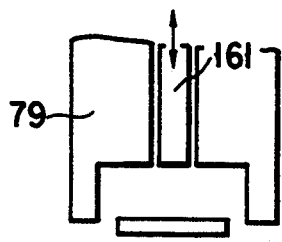
FIGS. 62A, 62B, and 62C are diagrams showing a modified staple pusher and explaining how the modified staple pusher deforms the modified staple shown in FIG. 61.

FIG. 62A shows a modified staple pusher 79. The pusher 79 has a groove 167 extending in the axial direction, and a U-notch formed in the distal end. A member 161 is fitted in the groove 167. The member 161 can be moved into and out of the U-notch of the pusher 79, virtually changing the depth of the U-notch. In accordance with the depth of the U-notch thus changed, the lengths of the legs 22a and 22b of the staple 22 (FIG. 61) are changed as the staple 22 is deformed by the pusher 79. Thus, the staple pusher 79 serves to staple living tissues of various thicknesses.

Figure 63:
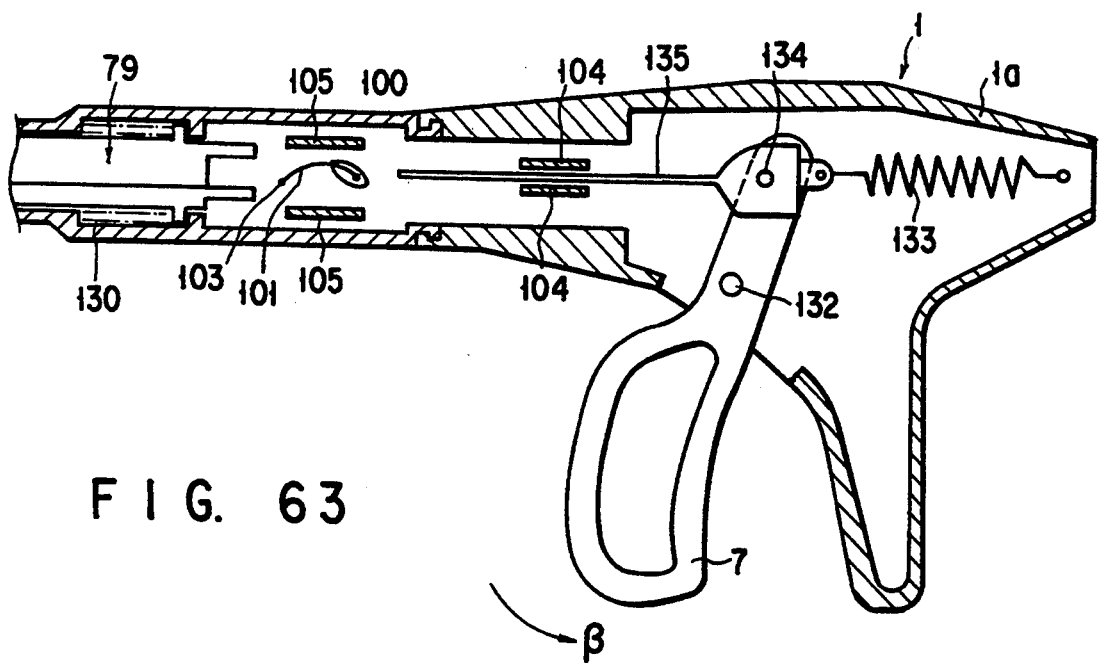
FIG. 63 is a sectional side view of a modification of the stapler according to the third embodiment of the invention.

A modification of the stapler shown in FIG. 46 will be described with reference to FIG. 63 and FIGS. 64A to 64D. In this modified stapler, a pusher 135 has a thin, plate-like distal end portion. The pusher 135 is held by a holder 104 and can be moved along the length of the operation section 1. The holder 104 protrudes of the inner surface of the frame 1a of the section 1. A streamline member 100 is connected to one end of a leaf spring 101 by a pin 102 and can rotate around the pin 102. The other end of the leaf spring 101 is fastened to the frame 1a by a pin 103. The leaf spring 101 is normally arching upwards as shown in FIG. 63. Two guides 105 extend parallel to the axis of the operation section 1—one above the member 100 and the spring 101 and the other below the member 100 and the spring 101. These guides 105 guide the distal end portion of the pusher 135 toward the staple pusher 79.

Figure 64A:
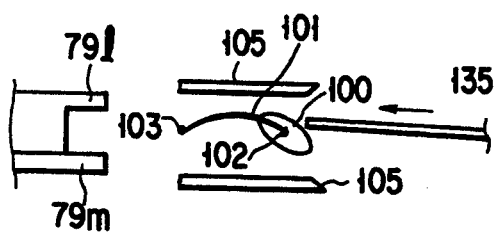
FIGS. 64A to 64D are diagrams explaining how the operation section of the modified stapler is operated.
Figure 64B:
Figure 64C:
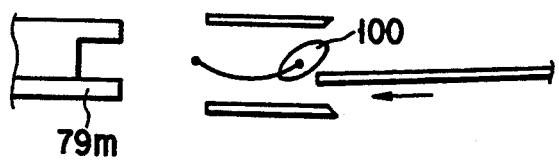
Figure 64D:
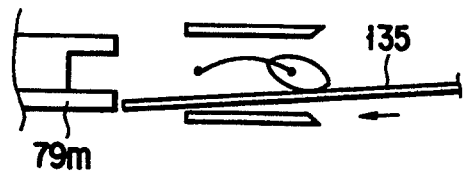

The operation section 1 is manipulated in the following manner. When the handle 7 is squeezed in the direction of arrow β, the pusher 135 is moved forward. The distal end of the pusher 135 abuts on the upper side of the streamline member 100 as is shown in FIG. 64A. As the pusher 135 is further moved forward, its distal end comes to contact the rear end of the right staple pusher 79l, pushing the pusher 79l forward. The pusher 79l bends the right leg of a staple. At this time, the pusher 135 presses and bends the leaf spring 101 downward as shown in FIG. 64B. Next, the staple-driving handle 7 is released, and the spring 133 rotates the handle 7 in the direction opposite to arrow β, thereby moving the pusher 135 backward. The leaf spring 101 remains bent downward, and the streamline member 100 remains inclined upward. Then, the handle 7 is squeezed again in the direction to arrow A, making the pusher 135 abut on the lower side of the streamline member 100 as is illustrated in FIG. 64C. As the pusher 135 is further moved forward, it abuts on the rear end of the left stapler pusher 79m. The pusher 79m is thereby thrust forward, bending the left leg of the staple as is shown in FIG. 64D. At this time, the pusher 135 presses and bends the leaf spring 101 upwards. Thus, the leaf spring 101 is set in the initial state. Even if the handle 7 is released, the spring 101 remains in this state.

Hence, every time the staple-driving handle 7 is squeezed and released, the pusher 135 moves the two staple pushers 79l and 79m alternately, making them deform a staple.

A stapler according to a fourth embodiment of the present invention will be described, with reference to FIG. 65, FIGS. 66A to 66C, and FIGS. 67 to 73.

Figure 65:
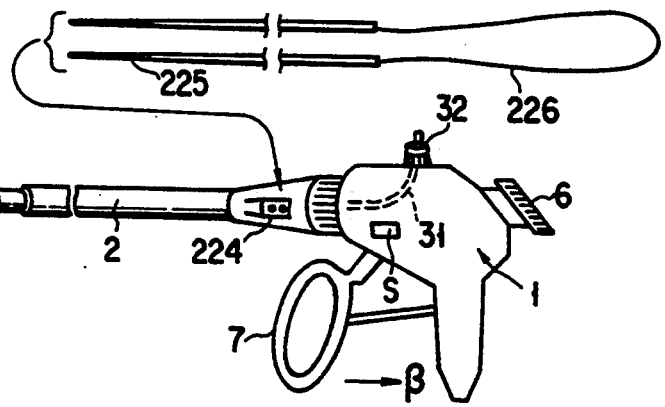
FIG. 65 is a perspective view of a stapler according to a fourth embodiment of the invention.
Figure 66A:
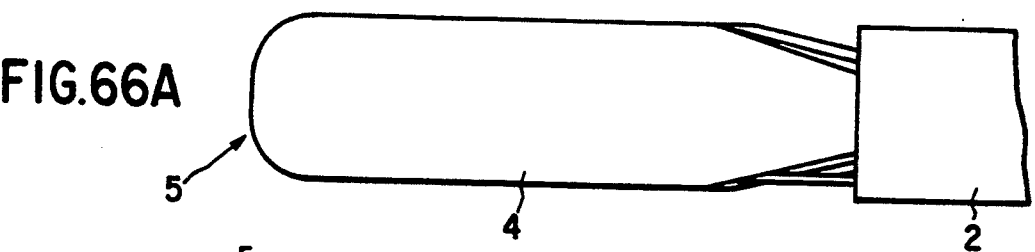
FIGS. 66A, 66B, and 66C are a plan view, right-side view, and left-side view showing the stapling member of the stapler shown in FIG. 65.
Figure 66B:
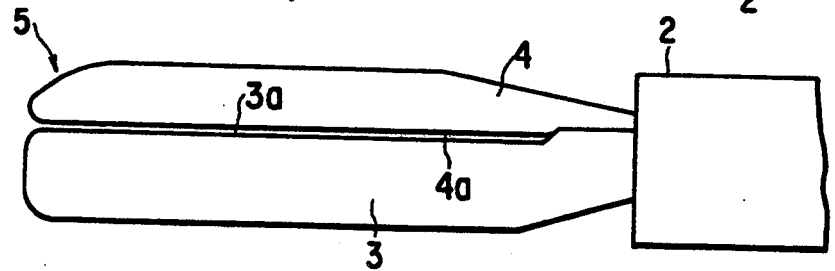
Figure 66C:
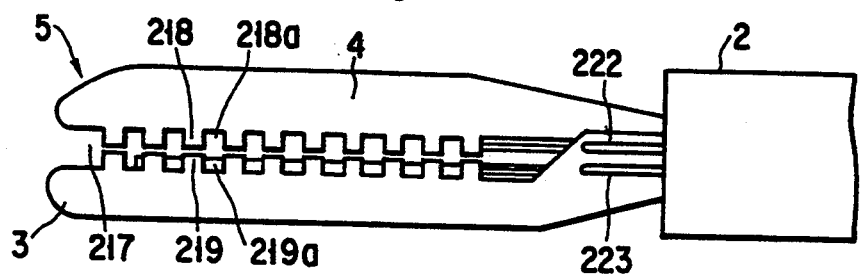

AS shown in FIG. 65, the stapler comprises an operation section 1, an insertion section 2 coupled to the distal end of the operation section 1, and a stapling member 5 connected to the distal end of the insertion section 2. The stapling member 5 has a cartridge 3 and an anvil 4. The operation section 1 has an operating member 6, a staple-driving handle 7, a connecting pin 32, and a switch S. The operating member 6 can be pulled and pushed to open and close the stapling member 5. The connecting pin 32 can be connected to a high-frequency cautery device (not shown). The switch W is operated to supply a high-frequency current from the cautery device to the stapling member 5 and to shut off the current supplied from the cautery device.

Figure 67:
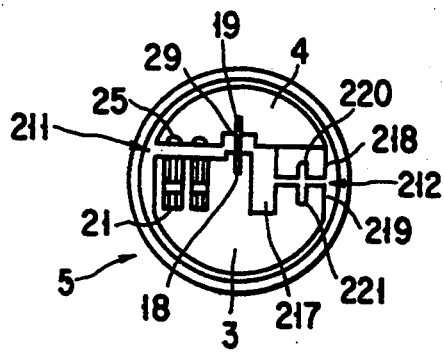
FIG. 67 is a front view of the stapling member.
Figure 68:
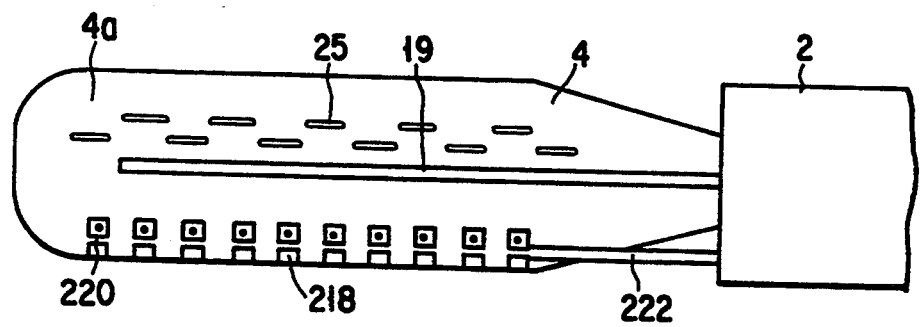
FIG. 68 is a plan view showing the anvil of the stapling member.
Figure 69:
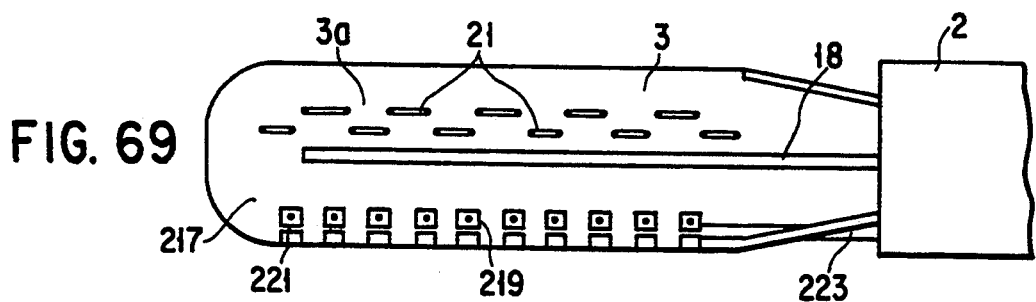
FIG. 69 is a plan view showing the cartridge of the stapling member.

As shown in FIGS. 67 to 69, cutter-guiding grooves 18 and 19 are formed in the inner surface of the cartridge 3 and that of the anvil 4, respectively, extending along the center lines of the cartridge 3 and the anvil 4. A cutter 29 is slidably inserted in the grooves 18 and 19, for cutting an tissue A held between the cartridge 3 and the anvil 4.

As shown in FIG. 67, the cartridge 3 contains a stapling unit 211 and a thread-applying unit 212. The stapling unit 211 is located on one side of the cutter-guiding groove 18, and the thread-applying unit 212 on the other wide of the groove 18.

Figure 70:
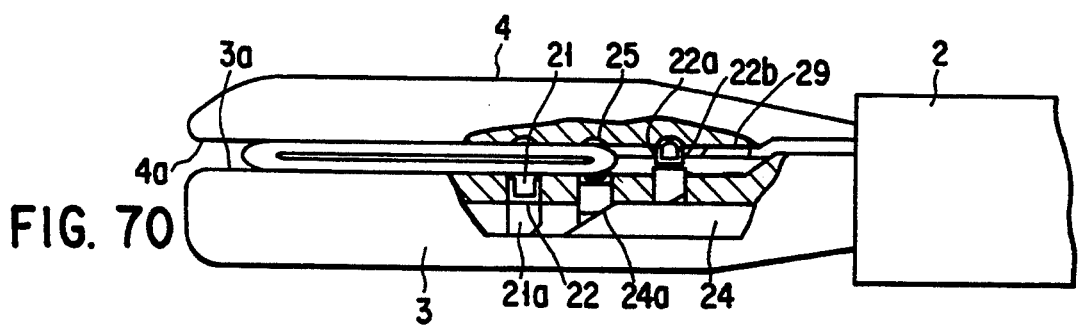
FIG. 70 is a cutaway side view of the stapling member.

As shown in FIG. 69, the stapling unit 211 has slits 21 arranged in staggered fashion in two rows. That is, any slit of one row overlaps the ends of the adjacent two slits of the other row. As shown in FIG. 70, pushers 21a are slidably placed in the slits 21, respectively, and can protrude upward from the inner surface of the cartridge 3. U-shaped staples 22 are inserted in the slits 21 and mounted on the pushers 21a, respectively, each with its legs 22a and 22b extending upwards. A pair of plate-guiding grooves (not shown) extend within the cartridge 3 along the row of slits 21. A pair of pusher plates 24 can be moved back and forth along the plate-guiding grooves.

As is shown in FIG. 68, grooves 25 are formed in the inner surface of the anvil 8. The grooves 25 are arranged in staggered fashion in two rows; they are so positioned as to meet the slits 21 of the stapling unit 211 when the inner surface of the anvil 4 contacts that of the cartridge 3. Each of these grooves 25 has an arcuate bottom so that the legs 22a and 22b of a staple may be bent inward and toward each other when they are pressed against the bottom of the groove 25.

The thread-applying unit 212 has an elongated recess 217 formed in the inner surface of the cartridge 3 and extending substantially parallel to the cutter-guiding groove 18. Teeth 219 are mounted in the recess 217, spaced apart equidistantly.

Figure 71:
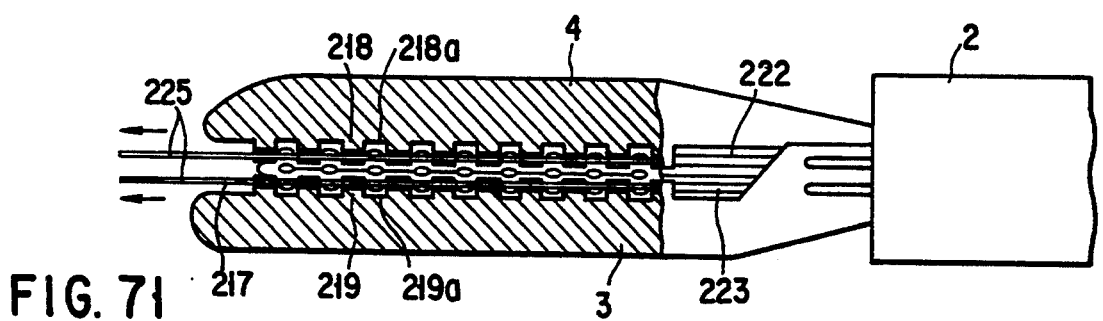
FIG. 71 is another cutaway side view of the stapling member, explaining how a tying thread is applied to body tissues.

Teeth 218 are mounted on the inner surface of the anvil 4. They are so located as to contact the teeth 219 when the inner surface of the anvil 4 contacts that of the cartridge 3. Hence, when the stapling member 5 is closed, the teeth 218 of the anvil 4 abuts on those 219 of the cartridge 3 as is shown in FIG. 71. A target tissue A is thereby clamped between the row of teeth 218 and the row of teeth 219, and parts of the tissue A bulge in the spaces 218a among the teeth 218 and the spaces 219a among the teeth 219.

Figure 62B:
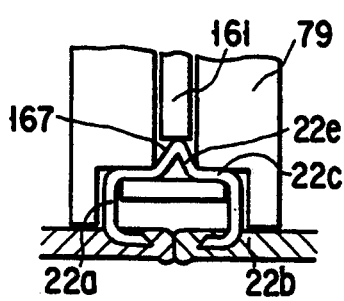
Figure 62C:
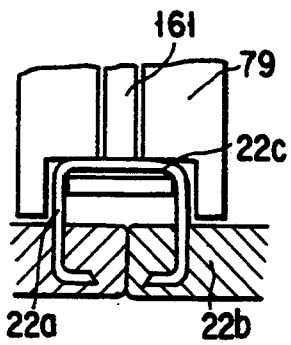

As shown in FIGS. 68 and 69, each tooth 218 has a thread-guiding groove 220, and each tooth 219 has a thread-guiding groove 221. The grooves 220 form a thread passage, the rear end of which communicates with one end of a flexible guide pipe 222. Similarly, the groove 221 form a thread passage, the rear end of which communicates with one end of a flexible guide pipe 223. The flexible pipes 222 and 223 are connected at the other end to a channel port 224 which is formed in one side of the operation section 1 as shown in FIG. 62. A tying thread 226 is inserted through the channel port 224 into the thread passages defined by the groove 220 and 221.

Figure 72:
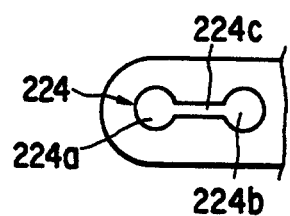
FIG. 72 is a plan view showing the channel port incorporated in the operation section of the stapler.

As is shown in FIG. 72, the channel port 224 has a pair of wire-guiding holes 224a and 224b. The port 224 also has a thread-guiding slit 224c connecting the holes 224a and 224b. The insertion section 2 has two thread-guiding holes—one extending between the hole 224a and the guide pipe 222, and the other extending between the hole 224b and the guide pipe 223.

As shown in FIG. 65, a tying thread 226 is fastened at its ends to the read ends of two guide wires 225. The guide wires 225 are inserted through the holes 224a and 224b, the thread-guiding holes formed in the section 2 and the flexible pipes 222 and 223 into the thread passages formed in the stapling member 5.

The stapler shown in FIG. 65 is manipulated in the following way. An incision is formed in a body wall such as the abdominal wall. The stapling member 5 and the insertion section 2 are inserted into a body cavity through the incision. The insertion section 2 is further pushed, thus moving the stapling member 5 toward the target tissue A. The operating member 6 is pulled, opening the stapling member 5. The member 5 is further moved until it catches the target tissue A. Then, the operating member 6 is pushed, closing the stapling member 5. The tissue A is thereby clamped between the cartridge 3 and the anvil 4. At this time, the teeth 218 of the anvil 4 press the tissue A onto the teeth 219 of the cartridge 3. Those parts of the tissue A, which are not clamped between the teeth 218 an 219, bulge in the spaces 218a and 219a among the teeth 218 and among the teeth 219, as is illustrated in FIG. 71.

In this condition, the staple-driving handle 7 is squeezed in the direction of arrow β, the pusher plates 24 are moved forward along the plate-guiding grooves, and the knife unit 29 are moved forward along the wire cutter-guiding grooves 18 and 19. As the pusher plates 24 move forward, their inclining distal ends 24a push up the pushers 21a sequentially, ultimately driving the staples 22 into the tissue A, one after another. The legs 22a and 22b of each staple 22 pierce the wall of the tissue A, abut on the bottom of the groove 25 formed in the inner surface of the anvil 4, and have their tips bent inwardly. As a result of this, the stapling unit 211 stitches the tissue A with the staples 22 arranged in two parallel rows.

Immediately after the tissue A is stitched, the cutter 29, which is moving forward along the grooves 18 and 19, severs the tissue A. Immediately before the cutter 29 cuts the tissue A, a high-frequency current is supplied from a cautery device (not shown) to the wire-cutter 29 via a cable (not shown) connected to the connecting pin 32. Therefore, the tissue A is cauterized while being severed, and there is no risk of bleeding at the severed portions of the living tissues A.

Then, the guide wires 225 are inserted through the holes 224a and 224b of the channel port 224, thus guiding the tying thread 226 into the operation section 1. Further, the wires 225 are inserted through the thread-guiding holes formed in the section 2 and the flexible pipes 222 and 223 into the thread passages formed in the stapling member 5. As a result, the half of the thread 226 is guided into the passage defined by the groove 220 of the teeth 218 of the anvil 4, whereas the remaining half of the thread 226 is guided into the passage defined by the grooves 221 of the cartridge 3.

One of the guide wires 225 pierces those parts of the tissue H2 located in the spaces 219a among the teeth 219 of the cartridge 3, while the other guide wire 225 pierces those parts of the tissue H2A located in the spaces 218a among the teeth 218 of the anvil 4. The tips of the wires 225, which protrude from the tissue H2, are held by forceps or the like and then pulled from the distal end of the stapling member 5. As a result, both halves of the tying thread 226 pass through the bulging parts of the tissue H2 located in the spaces 218a and 219a, stitching the edge of the tissue H2 severed from the tissue A.

Figure 73:
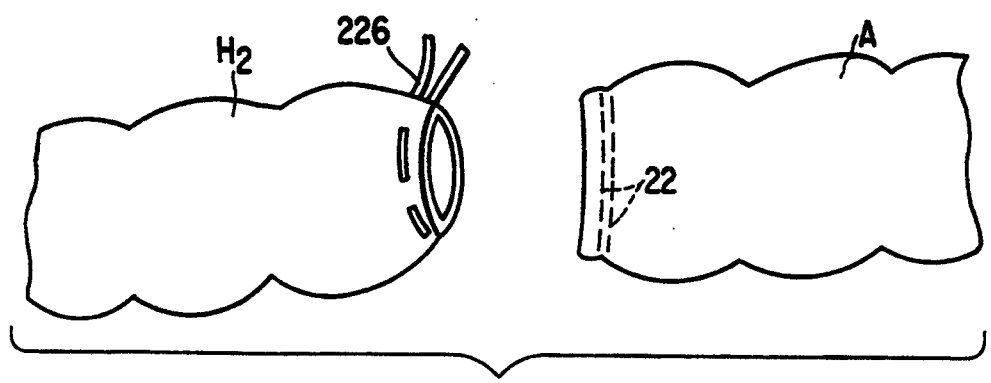
FIG. 73 is a perspective view illustrating an tissue stitched by the stapler.

Then, the operating member 6 is pulled, opening the stapling member 5. The stapled tissue A and the stitched tissue H2 can thereby be removed from the nip between the cartridge 3 and the anvil 4, as is shown in FIG. 73.

As described above, the staples 22 are driven into the tissue A by means of the sapling unit 211 located on one side of the cutter-guiding grooves 18 and 19, thus stapling together the opposing walls of the tissue A. Next, the cutter 29 is operated, severing the tissue into two portions. Thereafter, the thread-applying unit 212 located on the other side of the grooves 18 and 19 is operated, stitching the edge of the tissue portion H2 with the tying thread 225. Thus, the stapler shown in FIG. 65 can apply not only staples 21 but also a tying thread 226. Therefore, the stapler enables a surgeon to staple the opposing walls of a tubular tissue A and stitch the severed edge of a tubular tissue H2 with the tying thread 226, with ease and efficiency, after affected tissues have been removed from the tissue.

Figure 74:
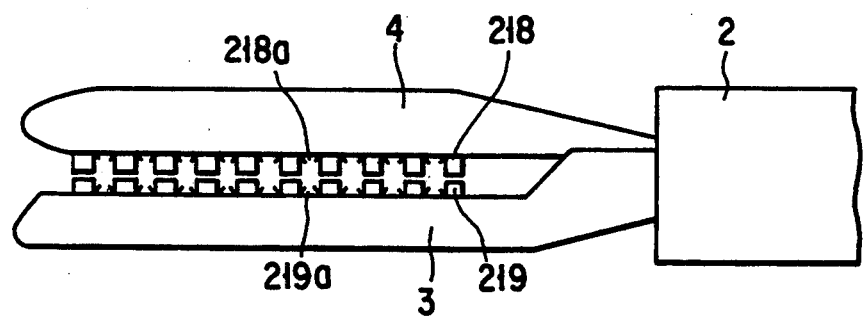
FIG. 74 is a side view a modification of the fourth embodiment, which is designed to apply staples with a tying thread wound around them.
Figure 75:
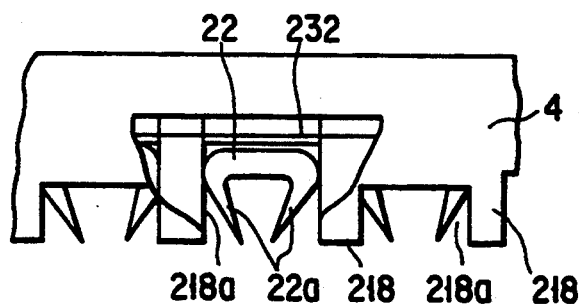
FIG. 75 is a diagram showing the staples inserted in the cartridge of the modified stapler.
Figure 76:
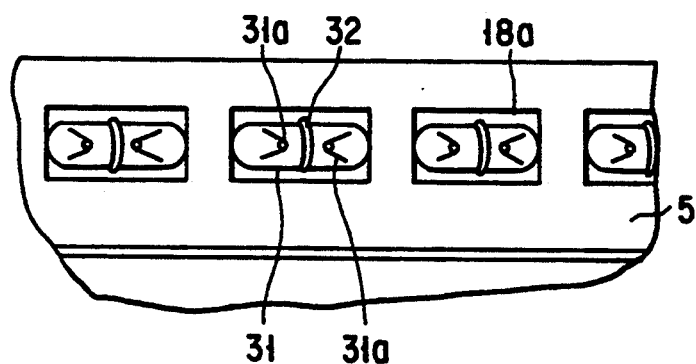
FIG. 76 is a plan view of the cartridge, showing the slits containing the staples.

FIGS. 74 to 75, FIG. 77A and 77B, and FIG. 78 show a modification of the thread-applying unit 212. As is shown in FIGS. 74 and 75, staples 22, with a single tying thread 232 wound around them, are placed in the spaces 218a among the teeth 218 of the anvil 3 and the spaces 219a among the teeth 219 of the cartridge 3. The legs 22a and 22b of each staple 22 are inclined toward each other, and one turn of the thread 232 is mounted on the middle portion of each staple 22. In other words, the staples 22 are connected by the typing thread 232.

When the stapling member 5 is closed, a tissue A is clamped between the cartridge 3 and the anvil 3. The staples 22 are thereby driven into the bulging parts of the tissue A which are located the spaces 218a among the teeth 218 of the anvil 3 and the spaces 219a among the teeth 219 of the cartridge 3. Hence, the staples 22 are secured to the tissue A.

Thereafter, other staples 22 are driven into the tissue A by means of the sapling unit 211 located on one side of the cutter-guiding grooves 18 and 19. These staplers 22 fasten the opposing walls of the tubular tissue A together. Then, the cutter 29 is operated, severing the tissue into two portions. Next, the operating member 6 on the operation section 1 is pulled, opening the stapling member 5. The tissue A into which the staples 22 with the thread 232 wound around them have been driven is removed from the nip between the cartridge 3 and the anvil 4. As shown in FIG. 77A, the thread 232 connects the staples 22. The thread 232 is pulled, tying the severed edge of the tissue A as illustrated in FIG. 77B.

Thus, as with the fourth embodiment, a surgeon can not only staple the opposing walls of a tubular tissue A but also stitch the severed edge of a tubular tissue with the tying thread 232. Also, as in the fourth embodiment, the severed edge of the tubular tissue A can be stitched with the tying thread 232, with ease and efficiency, after affected tissues have been cauterized and then removed from the tissue A.

In addition, the severed edge of the tubular tissue can be stitched together more easily than in the fourth embodiment in which the guide wires 225 are manipulated to apply the tying thread 226 to the severed edge of the tissue H2. This is because the thread 232 is applied merely by driving the staples 22 into the tissue A.

As shown in FIG. 77B, the end portions of the thread 232 are passed trough two holes of a fastener 234. Then, the end portions of the thread 232 are pulled, with the fastener 234 positioned near the severed edge of the tissue A. The severed edge of the tubular tissue A is thereby squeezed or collapsed with much ease.

The anvil 233 of a stapler designed to fasten a tubular tissue may be inserted into the tubular tissue A from the severed edge as is illustrated in FIG. 78. In this case, the severed edge of the tissue A can easily be fastened to the severed edge of another tubular tissue by means of the stapler.

Figure 81:
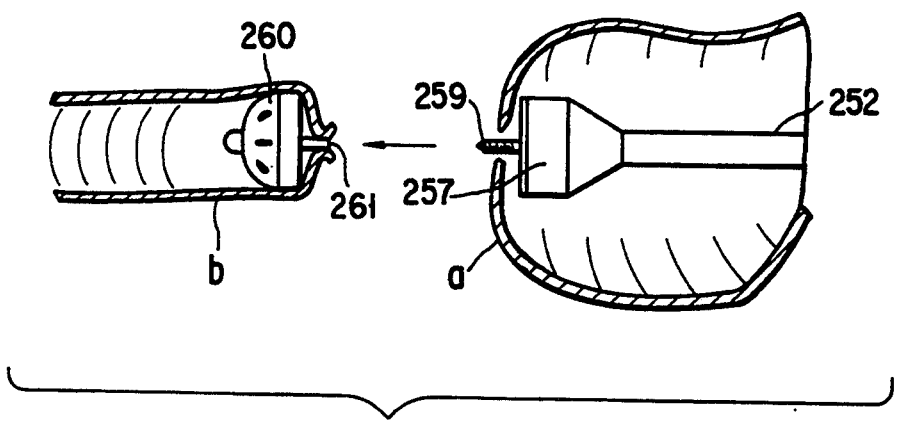
FIG. 81 is a diagram explaining how the stapler applies staples.

A stapler according to a fifth embodiment of the present invention, will be described with reference to FIGS. 79, 80, and 81.

As FIG. 79 shows, this stapler comprises an operation section 251 and an insertion section 252 connected at its proximal end to the operation section 251. The operation section 251 has a pair of handles 253, an adjustment screw 254, and a connecting pint 32. A cylindrical staple receptacle 257 is coupled to the distal end of the insertion section 252. The receptacle 257 contains a plurality of U-shaped staples 22 arranged in a circle.

An anvil shaft 258 extends through the insertion section 252 and the staple receptacle 257—coaxial therewith. A connecting screw 259 is connected to the distal end of the anvil shaft 258. The connecting screw 259 can rotate around its axis and can move along its axis; it protrudes from the distal end of the receptacle 257. An anvil 260 has connecting rod 261 which has a screw hole 262, in which the connecting screw 259 can be fit in screw engagement. The connecting screw 259 is fastened at the proximal end to the adjustment screw 254 which extends through the insertion section 252. The screw 259 is electrically connected to the connecting pin 32 by a cable 31 which extends through the anvil shaft 258.

A pusher 264 is located in the staple receptacle 257, for pushing the staples 22 forward. The pusher 264 can be moved back and forth along the axis of the receptacle 257. The pusher 264 is connected to the handles 253 by a connecting tube 265 which extends through the insertion section 252. A hollow cylindrical cutter 266 is located in the staple receptacle 257, surrounded by the staple 22 arranged in a circle. The cutter can be moved along the axis of the receptacle 257.

The connecting pin 32 is connected to the connector 34 coupled to one end of a cable 33. The other end of the cable 33 is connected to a cautery device 35.

The stapler shown in FIG. 79 is operated in the following way to apply the staples 22 to the abutting ends of tubular tissues, thereby to fastening the tubular tissues.

First, a tubular tissue A is positioned between the staple receptacle 257 and the anvil 260, and the anvil 260 is inserted into another tubular tissue b, with the connecting rod 261 protruding from the closed end of the tissue b. While applying a high-frequency current to the connecting screw 259, the screw 259 is thrust into the end wall of the tissue A and subsequently pierces the end wall of the tissue a. Then, the screw 259 is inserted into the screw hole 262 of the connecting rod 261 which pierces the end wall of the tissue b and protrudes therefrom. The connecting screw 259 is rotated around its axis until it is set in screw engagement with the connecting rod 261.

Next, the adjustment screw 254 is rotated, rotating the connecting screw 259 and moving the same back and forth, thereby adjusting the distance between the receptacle 257 and the anvil 260. Then, the handles 253 are squeezed, thrusting the pusher 264 forward. The pusher 264 pushes and drives the U-shaped staples 22 into the abutting walls of the tissues a and b. The legs of each U-shaped staple 22 abut on the anvil 260 and are bent toward each other. As a result, the walls of the tubular tissues a and b are stitched together. The cylindrical cutter 266 is thrust forward, cutting off the unnecessary inner parts of the stapled walls.

As described above, a high-frequency current is supplied to the connecting screw 259, whereby the end wall of the tissue a is cauterized and becomes easy to pierce. The screw 259 can therefore easily pierce the wall of the tissue a. Even if the screw 259 pierces a blood vessel, if any in the cauterized portion, there will be no bleeding because the blood vessel has been cauterized, too. No sharp stylus needs to be attached to the distal end of the connecting screw 259. The stapler has improved operating efficiency.

Figure 82:
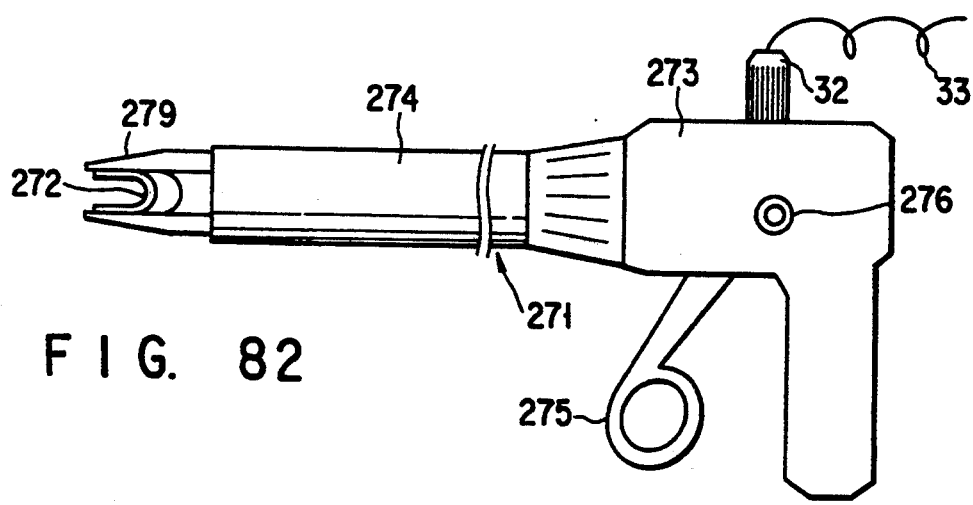
FIG. 82 is a side view of a clip applicator which is a sixth embodiment of this invention.
Figure 83:
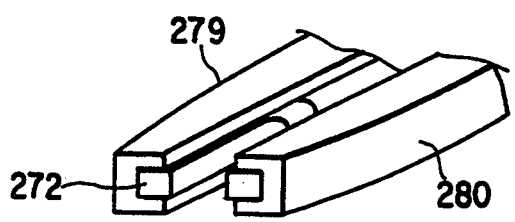
FIG. 83 is a perspective view showing the distal end portion of the clip applicator.

A clip applicator 271, which is a sixth embodiment of the present invention, will be described with reference to FIGS. 82 and 83.

The clip applicator 271 has a clip receptacle (not shown) which contains a plurality of 272. As shown in FIG. 82, the clip applicator 271 comprises an operation section 273 and an insertion section 274. The operation section 273 has a handle 275, a switch 276, and a connecting pin 32. The pin 32 is electrically connected to a high-frequency cautery device (not shown) by a cable 33.

Jaws 279 are connected to the distal end of the insertion section 274. The Jaws 279 can be opened and closed by operating the handle 275. When closed, the jaws 279 deform a clip 272 already held between them, thereby to ligate a blood vessel or the like.

The frame of the operation section 274, the insertion section 274, and the handle 275 are made of electrically insulating material such as plastics. The jaws 279 are made of electrically conductive material such as stainless steel. As can be understood from FIG. 83, the jaws 279 is coated with an insulating film 280, such as Teflon coating, ceramic coating, paint, or the like—except for the inner surface which contacts the clip 272.

The clip applicator is operated in the following way. After a blood vessel to ligate is placed in the gap between the legs of the clip 272 loaded between the jaws 279, the handles 275 are squeezed, closing the jaws 279. The clip is thereby deformed plastically, clamping the blood vessel. In this condition, the switch 276 is operated, supplying a high-frequency current to the clip 272 through the jaws 279 and subsequently cauterizing the clamped portion of the blood vessel. The clip applicator is operated again in the same way, thus deforming clips 272, clamping another portion of the blood vessel, and cauterizing this portion. Thereafter, that portion of the blood vessel which extends between the clamped by the clips 272 is cut off.

The blood vessel is clamped by virtue of the plastic deforming of the clip 272, thus stopping the blood flow in the vessel. Then, the clamped portion of the blood vessel is cauterized with a high-frequency current. Hence, there is no bleeding at the clipped portion of the blood vessel. Should the clip 272 slips from, or is removed by mistake from, the blood vessel during a surgical operation, no bleeding will occur at the clipped portion because this portion has been cauterized.

Figure 84:
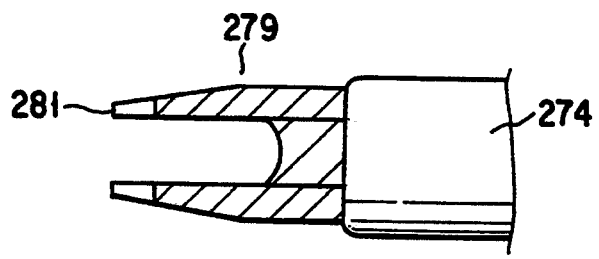

FIG. 84 shows a modification of the clip applicator 271. As is illustrated in FIG. 84, the jaws 279 has non-insulating tips 281. These tips 281 may either monopolar or bipolar. Bleeding occurs unexpectedly in the process of inserting the insertion section 274 into a body cavity. To stop such bleeding, it suffices to set the non-insulating tips 281 in contact with the bleeding tissues and to operate the switch 276. When the switch 276 is closed, a high-frequency current is supplied to the bleeding tissues via the non-insulating tips 281, cauterizing the tissues. Once cauterized, the tissues stops bleeding. The Jaws 279 having a non-insulating tip 281 each can be utilized not only to accomplish hemostasis, but also to peel tissue layers.

Hence, should any tissues start bleeding while the insertion section 274 is being inserted into a body cavity, the section 274 need not be immediately pulled from the body cavity and a high-frequency forceps need not be inserted into the body cavity at once. The modified clip applicator enables a surgeon to perform prompt and timely hemostasis, increasing the efficiency of surgical operations.

FIG. 85 shows a second modification of the clip applicator. As can be understood from this figure, each jaw 279 of this modified clip applicator have two recesses, an insulating body 282 embedded in the inner surface, and an electrode blade 283 held by the insulating body 282. Hence, a pair of clips 272 can be held between the jaws 279.

The modified clip applicator is operated as follows. First, a blood vessel to ligate is placed between the legs of the clips 272 held by the jaws 279. This done, the handles 275 are squeezed, closing the jaws 279. The clips 272 are thereby plastically deformed, clamping or ligating the blood vessel. Next, the switch 276 is operated, supplying a high-frequency current to both electrode blades 283. The electrode blades 283 heat and cut that portion of the blood vessel which is located between the clips 272.

With the modified clip applicator it is possible to apply two clips 272 to a tubular tissue at a time. In addition, hemostasis is achieved at the severed edges of the tissue since the electrode blades 283 cut the tissue by using a high-frequency current. Even if the clips 272 clamp the tissue less tightly than desired, no hemostatic measures need to be taken. The high-frequency current may be so reduced as to cauterize that portion of the blood vessel which is located between the clips 272, instead of cutting that portion of the blood vessel. In this case, too, reliable hemostasis can be accomplished.

A third modification of the clip applicator (the sixth embodiment) will be described with reference to FIGS. 86 and 87. As shown in FIG. 86, a jaw-operating handle 275 is rotatably connected to the frame 273 of the operation section. As shown in FIG. 87, the jaws 279 can hold two clips 272 at a time. Each jaw 279 has a groove formed in the inner surface of its distal end portion. The grooves of the jaws define a blade passage. Located in the blade passage are a pair of electrode blades 283 connected to a blade-operating handle 284 which is rotatably coupled to the operation section.

The modified clip applicator shown in FIG. 86 is operated in the following way. A blood vessel to ligate is placed between the legs of the clips 272 held between the jaws 279. Then, the handle 275 is operated, closing the jaws 279. Both clips 272 are thereby deformed plastically, clamping the blood vessel at two portions. In this condition, the switch 276 is operated, whereby a high-frequency current is applied to the clips 272 via the jaws 279. While supplying the current to the clips 272, the blade-operating handle 284 is operated, moving both electrode blades 283 forward. The electrode blades 283, which have a sharp edge each, can cut the blood vessel well.

A modified stapling member will be described with reference to FIGS. 88 and 89. As is shown in FIG. 89, the stapling member comprises a cartridge 3 and an anvil 4. The cartridge 3 has a cutter-guiding groove 18 formed in its inner surface as is illustrated in FIG. 88. Three rows of slits 21a, 21b and 21c are formed in the inner surface of the cartridge 3 on either side of a cutter-guiding groove 18. Hence, the cartridge 3 has six rows of slits formed in its inner surface. Inserted in these slits are staples 21 which can be moved up and down. Pushers 21a are located below the staples 21 and can be moved vertically. Each pusher 21a is wide enough to simultaneously contact three adjacent staples 21r, 21m, and 21l which are arranged side by side. Four pusher plates 24 extend through the cartridge 3 along the length thereof and parallel to each other—two located on one side of the cutter-guiding groove 18, and the remaining two on the other side of the groove 18. The pusher plates 24 can be moved back and forth at the same time for the same distance. The two pusher plates 24 on each side of the groove 18 abut on the lower side of each pusher 21a as they are thrust forward. The pushers 21a, the staples 22, and the pusher plates 24 are made of electrically conductive material such as metal. By contrast, the cartridge 3 and the anvil 4 are made of electrically insulating material.

The modified stapling member further comprises an operation section (not shown). The operation section has a connecting pin which is electrically connected to the pusher plates 24 at one end. The other end of the connecting pin can be connected to a high-frequency cautery device, as in the fourth embodiment (FIG. 65). Hence, a high-frequency current can be supplied to the pusher plates 24.

With this modified stapling member, a high-frequency current is supplied to all staples driven into a tubular organ being stapled, such as intestine. Hence, hemostasis can be accomplished at the same time the organ is stitched and an unnecessary part thereof is cut off.

The high-frequency current may be supplied some of the staples, not to all of them. For instance, the current can be supplied to only the staples 22 inserted in the center row of slits 211 if the pushers 21a located below the outer rows of slits 21m and 21r are made of electrically insulating material.

The pushers 21a need not be made electrically conductive material for the purpose of supplying the high-frequency current to the staples 22. Rather, the cartridge 3 and the anvil 4 may be made of conductive material, and the high-frequency current may be supplied from the high-frequency cautery device.

A stapler according to a seventh embodiment of the invention will be described with reference to FIG. 90 through FIG. 95.

Figure 90:
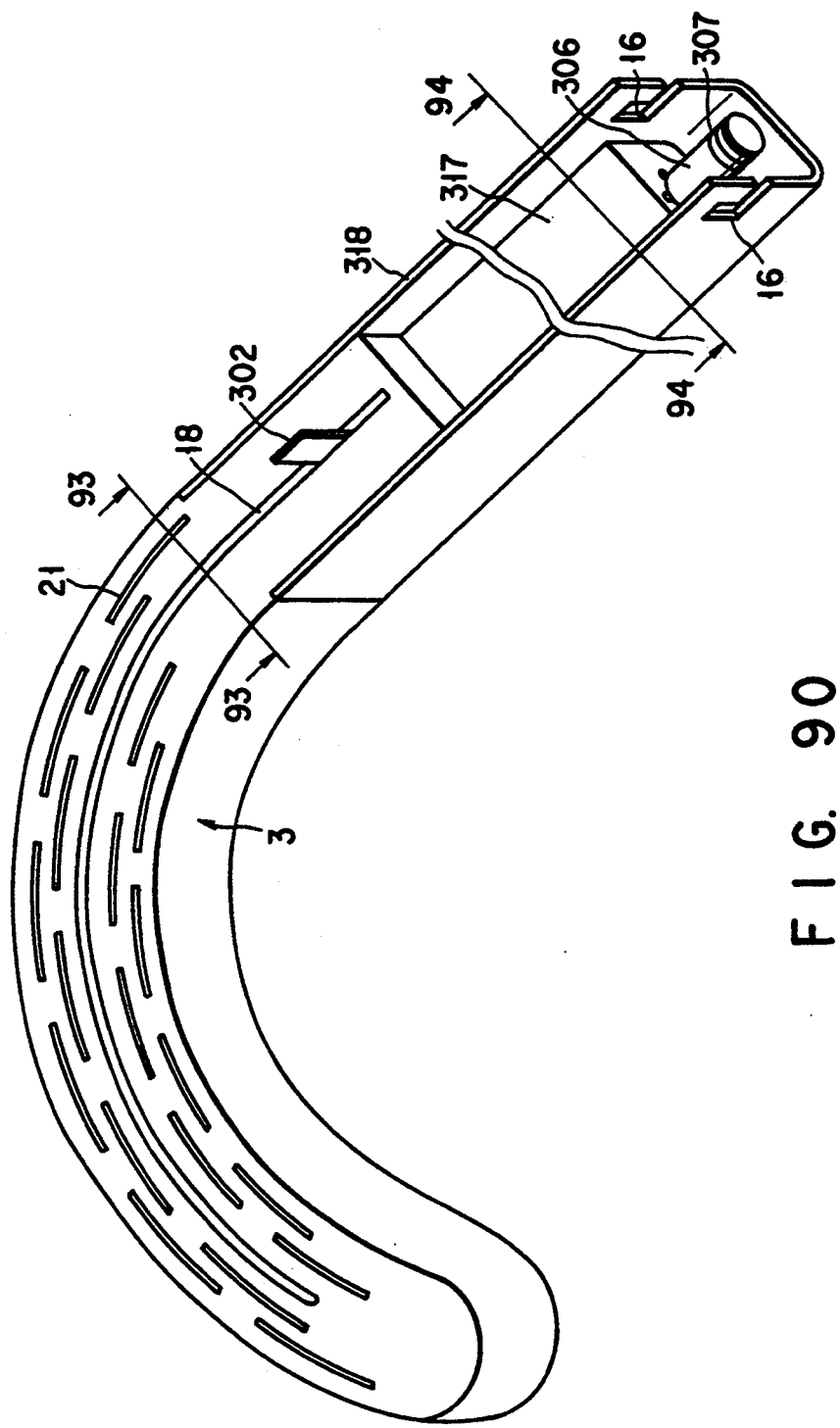
FIG. 90 is a perspective showing the cartridge of the modified stapling member of a stapler according to a seventh embodiment of the present invention.
Figure 91:
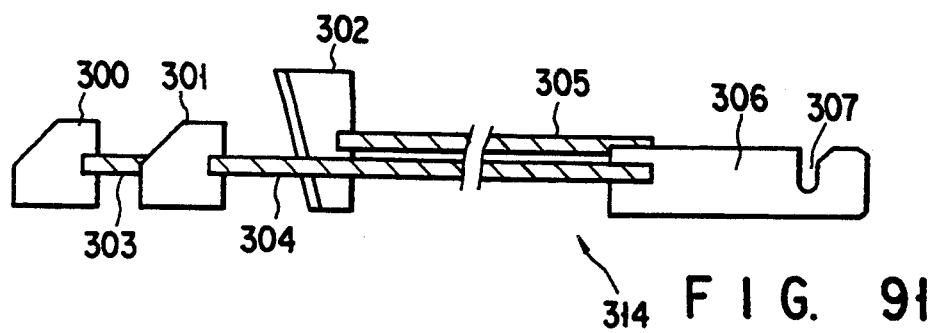
FIG. 91 is a side view showing the pushers, the cutter, and the members connecting the pushers and the cutter—all incorporated in the cartridge shown in FIG. 90.
Figure 92:
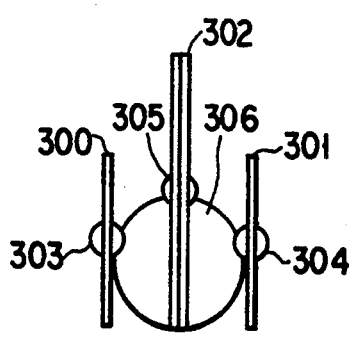
FIG. 92 is a front view illustrating the components shown in FIG. 91.
Figure 93:
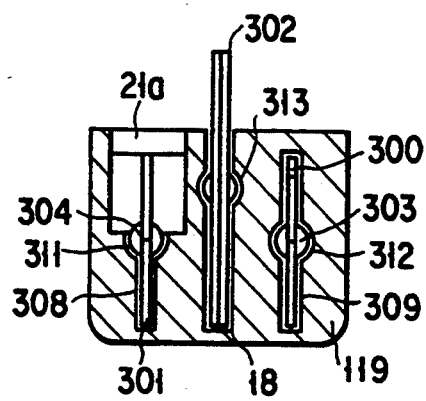
FIG. 93 is a cross-sectional view of the cartridge, taken along the line 93—93 in FIG. 90.

This stapler is similar to the first embodiment (FIGS. 1 to 12) in that the cartridge 3 curves, as evident from FIG. 90, in a plane perpendicular to the direction of ejecting staples. The stapler basically differs from the first embodiment in that pushers 300 and 301 which correspond to the pusher plates 24, and a cutter 302 which corresponds to the wire cutter 20 are located in the cartridge 3, not incorporated in the insertion section (not shown).

The pushers 300 and 301 and the cutter 302 are connected to wires 303, 304, and 305 which are connected at the proximal end to a connector 306. The pushers 300 and 301, the cutter 302, the wires 303 to 305, and the connector 305 are made of flexible material and constitute a flexible assembly 314. The assembly 314 is rotatably coupled to the insertion section by means of an annular groove 307 formed in the circumference of the connector 306 and a pin (not shown) protruding from the distal end of the insertion section.

The cartridge 3 can be removably coupled to the insertion section. Instead, it may be secured to the insertion section. If so, the connector 305 can be dispensed with, and the wires 303 to 305 extend through the insertion section and connected to the constituent members of the operation section (not shown).

Figure 94:
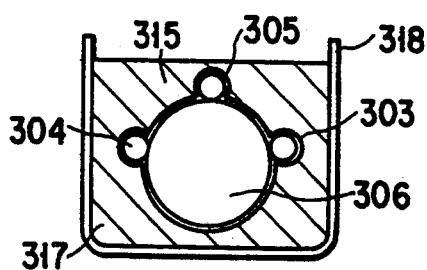
FIG. 94 is a cross-sectional view of the cartridge, taken along the line 94—94 in FIG. 90.

The pushers 300 and 301 can be moved back and forth along guide grooves 308 and 309 formed in the inner surface of the cartridge 3. Similarly, the cutter 302 can move back and forth along the cutter-guiding groove 18 formed in the inner surface of the cartridge 3. The wires 303, 304, and 305 can be pulled and pushed through guide holes 311, 312 and 313 made in the cartridge 3, as is shown in FIG. 94. The connector 306 can also move along the length of the cartridge 3 through the guide hole 315 made in a member 317 located in the proximal end portion of the cartridge 3.

The guide grooves 308 and 309 and the guide holes 311 to 313 extend parallel to the curving axis of the cartridge 3. Nonetheless, the flexible assembly 314, which is composed of the pushers 300 and 301, the cutter 302, the wires 303 to 305, and the connector 305, can smoothly move back and forth because of its own flexibility.

The wires 303, 304, and 305 may be stranded stainless-steel wires. They are guided by flexible guides (not shown) which are, for example, tubes or coils.

As shown in FIG. 90, staple-ejecting slits 21 are formed in the inner surface of the cartridge 3. The slits 21 are arranged in four rows—two located on one side of the cutter—guiding groove 18, and the other two located on the other side of the groove 18. The slits 21 of the two rows on either side of the groove 18 are so positioned that any of one row overlaps the adjacent two of the other row. All slits 21 have the same length, and staples of the same size are driven through these slits 21. Instead, the slits 21 of the outer row on either side of the cutter-guiding groove 18 may be longer than those of the inner row, so that longer staples may be ejected through the slits 21 of the outer row.

Figure 95:
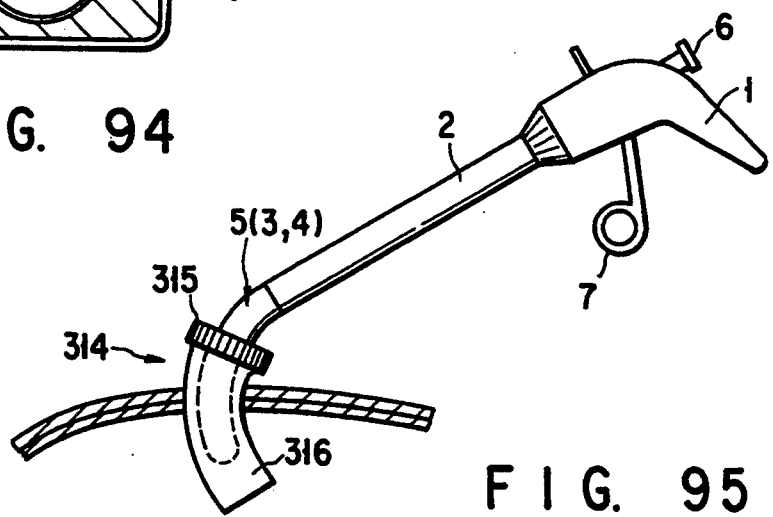
FIG. 95 is a diagram explaining how to operate the stapler according to the seventh embodiment of the present invention.

As is shown in FIG. 95, the stapler can be used in combination with a trocar 314 which comprises a cap 315 and a sheath 316 connected to the cap 315. The sheath 316 is made of, for example, PTFE and is flexible enough to bend as much as the cartridge 3 is curving. Although not shown, a valve means is attached to the proximal end of the trocar 314, for prevent the leakage of gas from the body cavity into which the sheath 316 has been inserted. Instead, the valve means may be removal coupled to the flexible sheath 316.

As shown in FIG. 95, the cartridge 3 is connected to an anvil 4, constituting a stapling member 5. To insert the stapling member 5 into a body cavity, it is closed and then inserted into the trocar 314. Being flexible unlike the convention rigid ones, the sheath 316 of the trocar 314 bends as the member 5 is gradually inserted into it, allowing the passage of the stapling member 5. Thus, the stapling member 5 can be smoothly inserted into a body cavity through the trocar 314. Thereafter, the stapler is manipulated in the same way as the first embodiment.

Figure 96:
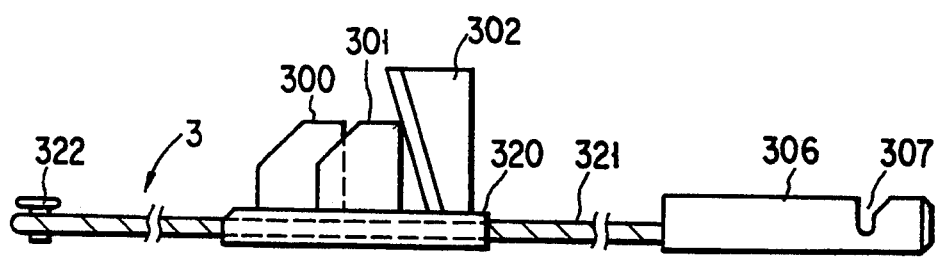
FIGS. 96 and 97 are a side view and top plane view, respectively, showing a mechanism which may be incorporated in the seventh embodiment, for driving the pushers and the cutter.
Figure 97:
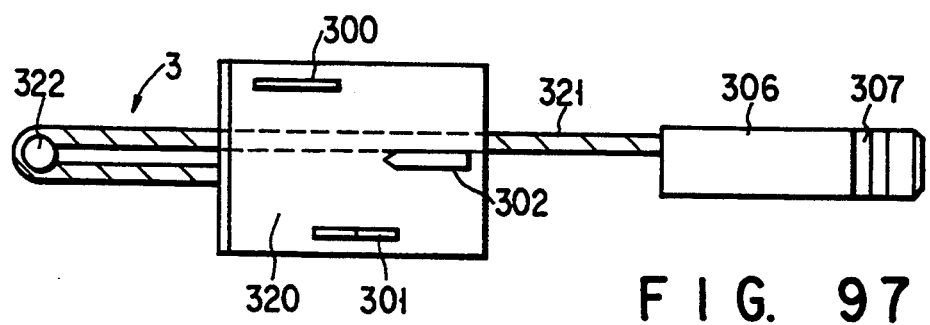

As is shown in FIGS. 96 and 97, the pushers 300 and 301 and the cutter 302 may be secured to a base 320 made of elastic material. The distal end of this base 320 is connected to the distal end of a wire 321. The proximal end of the wire 321 is connected to the connector 306. The middle portion of the wire 321 is wrapped around a pulley 322 which is rotatably supported. When the connector 306 is pulled backward, the pushers 300 and 301 and the cutter 302 are thrust forward, to ligate and cut body tissues.

A modification of the stapler of the seventh embodiment will be described with reference to FIGS. 98 and 99.

Figure 98:
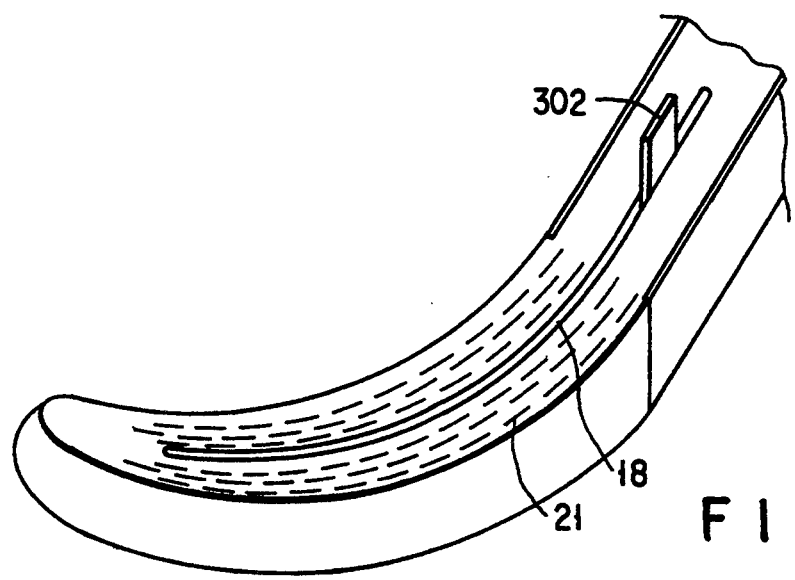
FIG. 98 is a perspective view of a modification of the cartridge used in the seventh embodiment.
Figure 99:
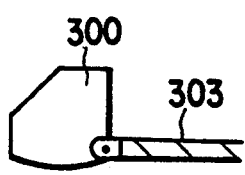
FIG. 99 is side view showing one of the pushers incorporated in the cartridge shown in FIG. 98 and a wire connected to the pusher.

FIGS. 98 and 99 show a modification of the cartridge 3. The modified cartridge also curves in a plane perpendicular to the direction of ejecting staples. As can be understood from FIG. 99, the pushers 300 and 301 and the cutter 302 have a lower side arcuated with same curvature as the cartridge 3. (In FIG. 99, only the pusher 300 is shown.) The wires 303, 304, and 305 are connected to the pusher 300, the pusher 301, and the cutter 302, respectively, by pins so that each of these components 300, 301 and 302 may rotate around the pin.

Having a curving stapling member 5, the stapler according to the seventh embodiment is advantageous in three respects. First, it can easily approach a position where the target tissues are located. Second, the member 5 can be easily moved to hold an organ existing on the bottom of the abdominal cavity or the chest cavity. Third, the distal end of the cartridge can be seen well through an endoscope, enabling a surgeon to see whether or not that portion of the organ to which he or she wants to apply staples is located inside the distal end portion of the cartridge. Therefore, the stapler can help the surgeon to achieve successful intra-cavity operations.

Generally, the insertion section of the stapler can be either rigid or flexible. If rigid, it can be straight or curving. If the insertions section is a curving or flexible one, the components (e.g., the wires 303) extending through it from the operation section, for operating the stapling member 5, may be made of flexible material so that they can bend, too. Also, the members guiding these components may be flexible ones such as tubes and coils.

Another stapler, which is an eighth embodiment of the invention, will be described with reference to FIG. 100, FIGS. 101A and 101B, and FIGS. 102 and 103.

Figure 100:
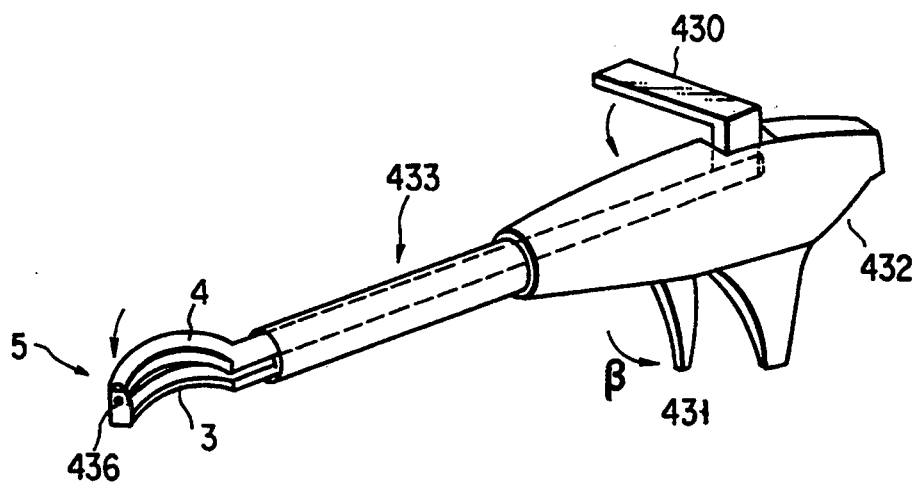
FIG. 100 is a perspective view of a stapler according to an eighth embodiment of the present invention.

As clearly shown in FIG. 100, a lever 430 and a handle 431 are rotatably attached to the frame 432 of the operation section. An insertion section 433 is connected at the proximal end to the frame 430. Coupled to the distal end of the insertion section 433 is a stapling member 5 which comprises a cartridge 3 and an anvil 4. The anvil 4 is connected to the cartridge 3 by a pin 436 and can rotate around this pint 436. The cartridge 3 and the anvil 4 curve in the same direction. The cartridge 3 has grooves for guiding pusher plates. These grooves curve along the length of the cartridge 3. Pusher plates 24 are placed in the grooves and made of flexible material so that they may move along the curving grooves.

Figure 103:
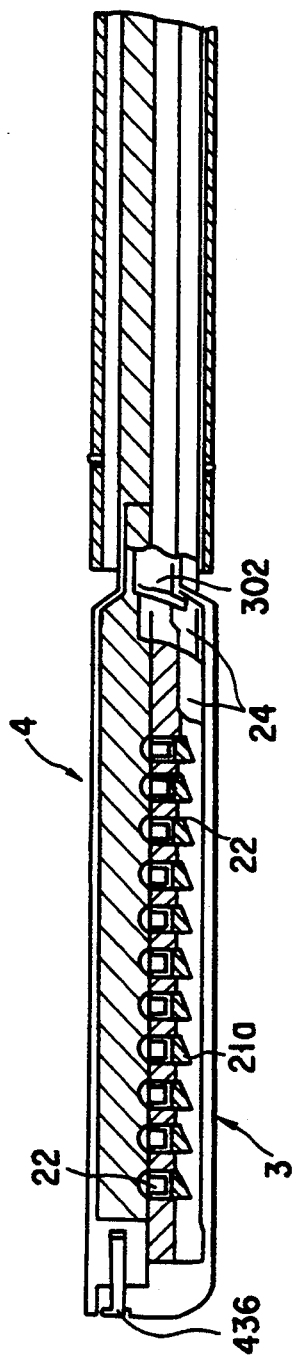
FIG. 103 is a sectional side view of the cartridge of the stapling member.

The anvil 4 is connected to the lever 430. When the lever 430 is rotated in the direction of the arrow shown in FIG. 100, the anvil 4 is rotated around the pin 436 in the direction of the arrow shown in FIG. 101A. The pusher plates 24 are connected to the handle 431. When the handle 431 is squeezed in the direction of arrow $\beta$ as shown in FIG. 100, the pusher plates 24 are thrust forward and push up pushers 21a which are shown in FIG. 103. Thus pushed, the pushers 21a drive staples 22.

Figure 101A:
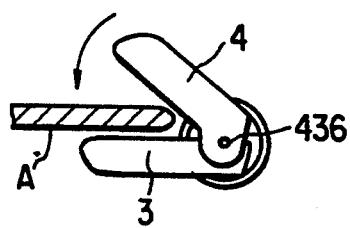
FIGS. 101A and 101B are side views showing the stapling member of the stapler in the open position and the closed position, respectively.
Figure 101B:
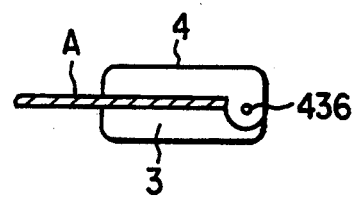

The stapler shown in FIG. 100 is operated in the following way to staple body tissues and cut unnecessary parts thereof. First, the lever 430 is rotated in the direction opposite to the arrow shown in FIG. 100, thereby opening the stapling member 5. The stapler is moved, placing tissues A (e.g., lung tissues) in the gap between the cartridge 3 and the anvil 4 as is illustrated in FIG. 101A. The lever 430 is rotated in the direction of the arrow (FIG. 100), rotating the anvil 4 in the direction of the arrow (FIG. 101A). The tissues A are thereby clamped between the cartridge 3 and the anvil 4. Next, the handle 431 is squeezed, moving the pusher plates 24 forward along the curving groove formed in the inner surface of the cartridge 3. Thus moved, the plates 24 push the pushers 21a upwards, whereby the pushers 21a drive the staples 22 into the tissues A clamped between the cartridge 3 and the anvil 4. As a result, the tissues are stitched together. In the meantime, the cutter (not shown) is moved forward through the cartridge 3 and the anvil 3, cutting off unnecessary parts of the tissues A.

Figure 102:
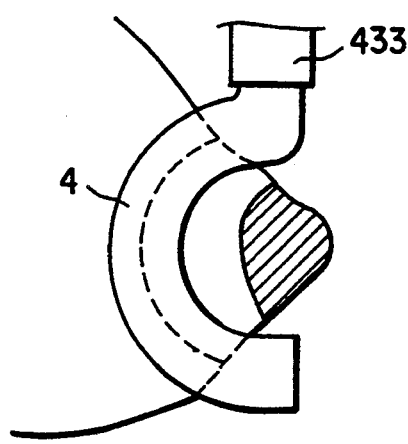
FIG. 102 is a diagram showing the positional relation between the stapling member and the tissues stapled by the member.

The resultant stitch line curves as indicated by the broken line in FIG. 102. This makes it possible to cut off the least parts necessary from the clamped tissues. Further, since the cartridge 3 and the anvil 4 are connected rotatably by the pin 436, they can clamp tissues more firmly than otherwise. In addition, when the stapling member 5 is closed, the anvil 4 exerts a clamping force uniformly all over the tissues, whereby the tissues can be stitched together neatly.

A stapler according to a ninth embodiment of the invention will be described with reference to FIGS. 104 to 109. This stapler is characterized in that the insertion section 2 has a distal end portion which can bend in two directions.

Figure 104:
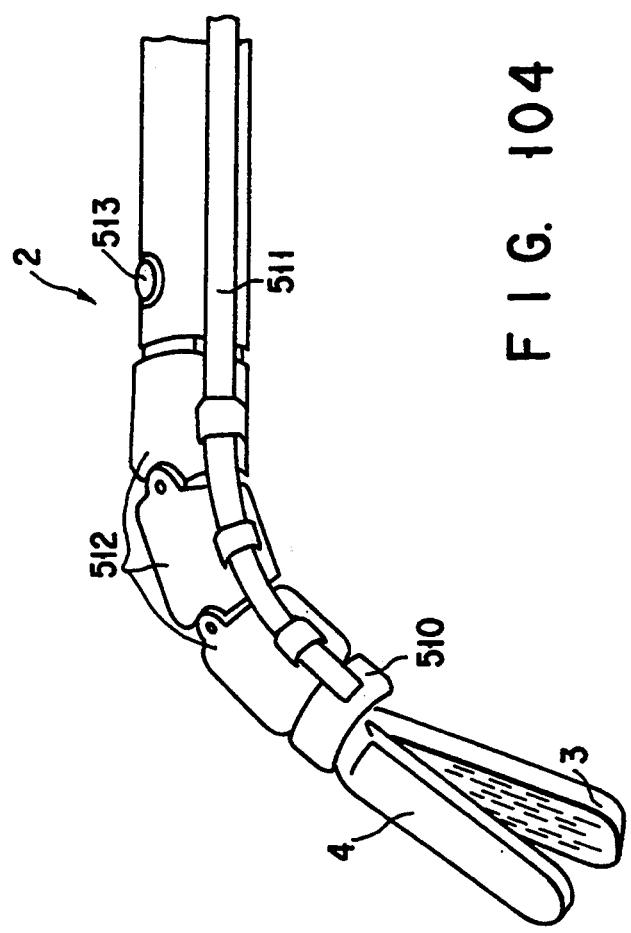
FIG. 104 is a perspective view showing a stapler according to a ninth embodiment of this invention.

As shown in FIG. 104, the distal end portion of the insertion section 2 comprises a plurality of segments 512 and a ring-shaped cam 510. The cam 510 is mounted on the foremost segment 512 and can slide back and forth. The segments 512 are hollow cylindrical members, each connected to the next one by a pair of coaxial pins and able to rotate with respect to the next one in the plane perpendicular to the direction of ejecting staples. A pair of elongated leaf springs 511 are slidably mounted on the sides of the insertion section 2. The leaf springs 511 are connected at the front end to the cam 510, and at the rear end to a lever rotatably connected to the frame of the operation section (not shown). Hence, when the lever is operated, the cam 510 is moved back and forth.

A cartridge 3 and an anvil 4, constituting a stapling member, are rotatably coupled to a connector inserted in the segments 512. They are biased by a spring means and to assume open positions. The cam 510 performs the same function as the outer tube 9 used in the first embodiment. That is, the cam 510 presses the cartridge 3 and the anvil 4 toward each other when it is pulled backward, and allows the cartridge 3 and the anvil 4 to rotate into their open positions when it is pushed forward.

When one of the leaf springs 511 is pulled backward for a predetermined distance, the distal end portion of the insertion section 2 is bent in one direction. If both leaf springs 511 are further pulled back for the same direction, the stapling member is opened while the distal end portion of the insertion section 2 remains bent in said one direction.

In the stapler shown in FIG. 104, the cartridge 3 can be removably attached to the connector inserted in the distal end portion of the insertion section 2 as is shown in FIGS. 105 to 109. More specifically, as shown in FIG. 105, a thin coiled wire 518 is fastened at the forward end to a pusher plate 24 inserted in the cartridge 3. The rear end of the coiled wire 518 is connected to a first coupling 514 which projects form the rear-end face of the connector. Also inserted in the cartridge 3 is a thick coiled wire 519, through which the thin coiled wire 518 extends and is guided. The thick coiled wire 519 constitutes the connector. As shown in FIG. 106, a second coupling 515 is connected to the rear end of the coiled wire 519. The second coupling 511 is a hollow cylinder having an annular groove formed in its circumference. The first coupling 518 extends through the second coupling 515 and is positioned coaxial therewith, with its rear end portion protruding from the rear end of the second coupling 515 as illustrated in FIG. 106.

An operating coil spring 590 extends from the frame of the operation section (not shown) through the insertion section 2, reaching the rearmost segment 512 (FIG. 104). As shown In FIG. 107, a first cylindrical split-spring 516 is fastened to the forward end of the operation coil spring 590. The first split-spring 516 has such a size that the first coupling 514 may fit into it elastically. As shown in FIG. 108, a second cylindrical split-spring 517 is mounted on the first split-spring 516 and positioned coaxial therewith. The second split-spring 517 has such a size that the second coupling 515 may fit into it elastically. A lever 591 is rotatably connected at one end to the second split-spring 517 as is shown in FIG. 109. The other end of the lever 591 is located below a push button 592 slidably set in a hole made in the wall of the insertion section 2. The push button 592 is biased upward by a coil spring 593. It is pushed down to release the cartridge 3.

The first coupling 514 and the second coupling 515 are pushed into the first split-spring 516 and the second split-spring 517, respectively, against the forces of these springs 516 and 517, whereby the cartridge 3 is attached to the distal end of the insertion section 2. To remove the cartridge 3 from the insertion section 2, the button 592 is pushed down against the bias of the spring 593, rotating the lever 591. Thus rotated, the lever 591 expands the second split-spring 517, which in turn expands the first split-spring 516. As a result, the cartridge 3 can be pulled out of the insertion section 3.

The above-described mechanism connecting the cartridge 3 to the insertion section 2 enables both coiled wires 518 and 519 can smoothly run through the insertion section 2 though the distal end portion thereof is bent. Driven forward by these coiled wires 158 and 519, the pusher plate 24 ejects staples.

A stapler according to a tenth embodiment of the present invention will be described with reference to FIGS. 110 and 111.

Figure 110:
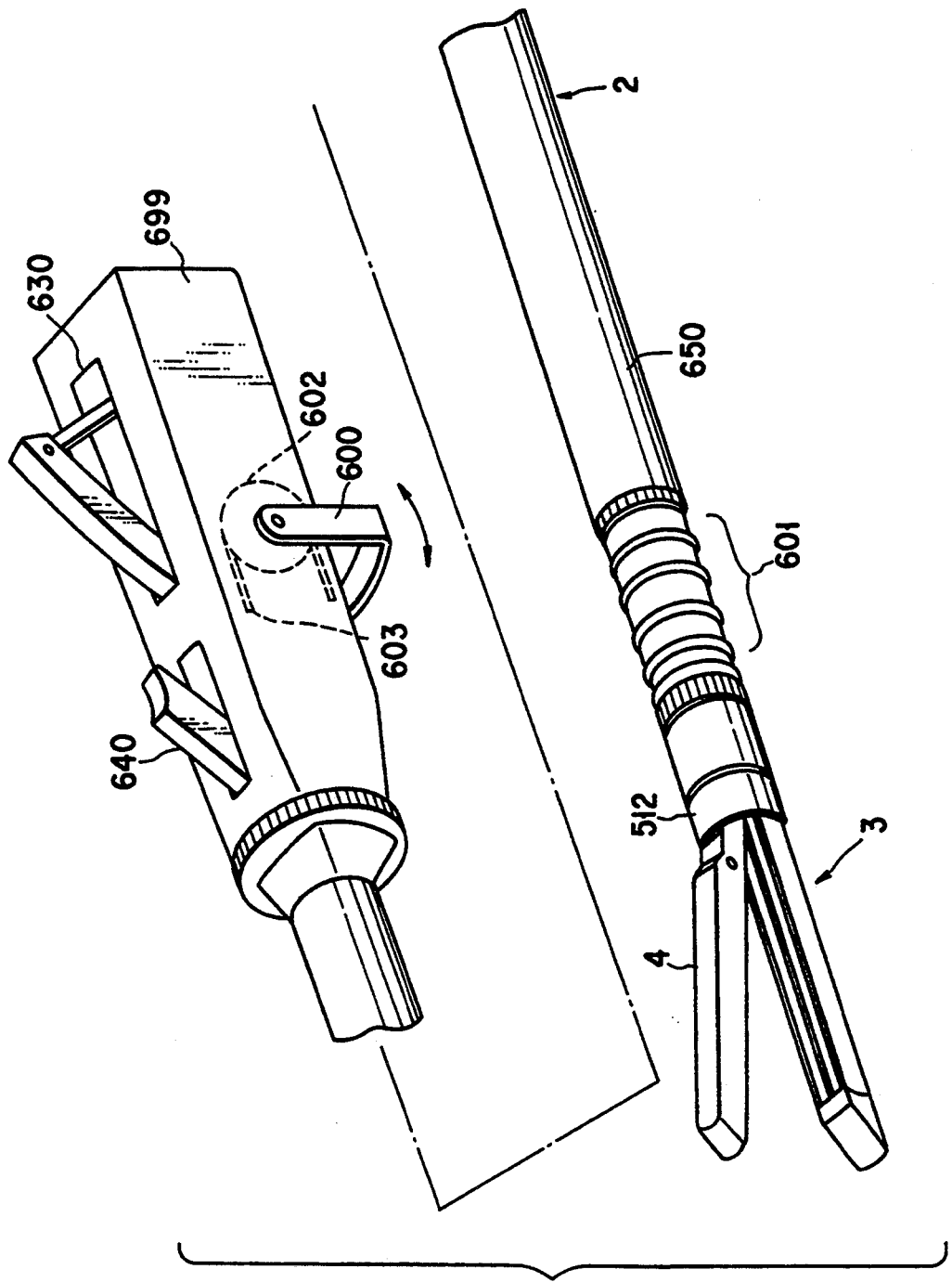
FIG. 110 is a perspective view showing a stapler according to a tenth embodiment of this invention, except the middle portion of the insertion section of the stapler.
Figure 111:
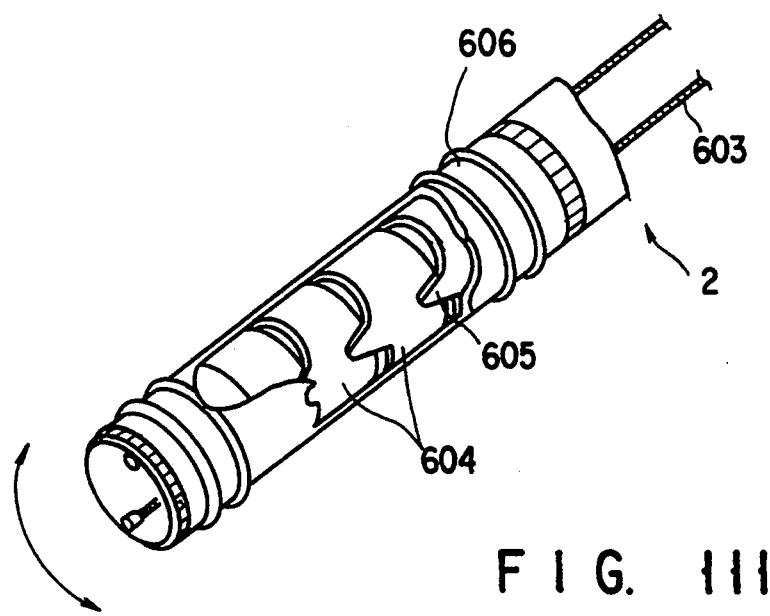
FIG. 111 is a cutaway perspective view of the flexible portion of the insertion section of the stapler shown in FIG. 110.

As shown in FIG. 110, the stapler comprises an operation section 699, an insertion section 2 connected to the distal end of the operation section 699, and a stapling member connected to the distal end of the insertion section 2 and comprising a cartridge 3 and an anvil 4. An anvil operating lever 630, a pusher-plate operating lever 640, and an angle knob 600 are rotatably connected to the operation section 699. The angle knob 600 is connected to the ends of a horizontal pin which extends through the section 699 at right angles to the axis thereof. A pulley 602 is fastened to the pin an located within the operation section 699. A wire 603 is wrapped around the pulley 602.

The distal end portion 601 of the insertion section 2 is made flexible. More specifically, as shown in FIG. 111, the portion 601 comprises a plurality of hollow cylindrical segments 604, each connected to the next one by a pair of coaxial pins and able to rotate with respect to the next one. The ends of the wire 603 are fastened to the foremost segment 604, spaced apart by 180° along the circumference of the segment 604. The distal end portion 601 is covered with a flexible resin sheath 606, whereas the other portion of the insertion section 2 is covered with a rigid resin sheath 650.

When the angle knob 600 is rotated back and forth, the pulley 602 is rotated, driving the wire 603 connected at both ends to the foremost segment 604. The foremost segment 604 is thereby driven forward at one side and backward at the other wide, whereby the flexible distal end portion 601 is bent by any desired angle in the plane perpendicular to the direction of ejecting staples.

A device for checking the conditions of the tissues fastened together with staples driven from the cartridge of a stapler, and a device for electrically operating the operation section of the stapler will now be described with reference to FIGS. 112, 113, and 114.

Figure 112:
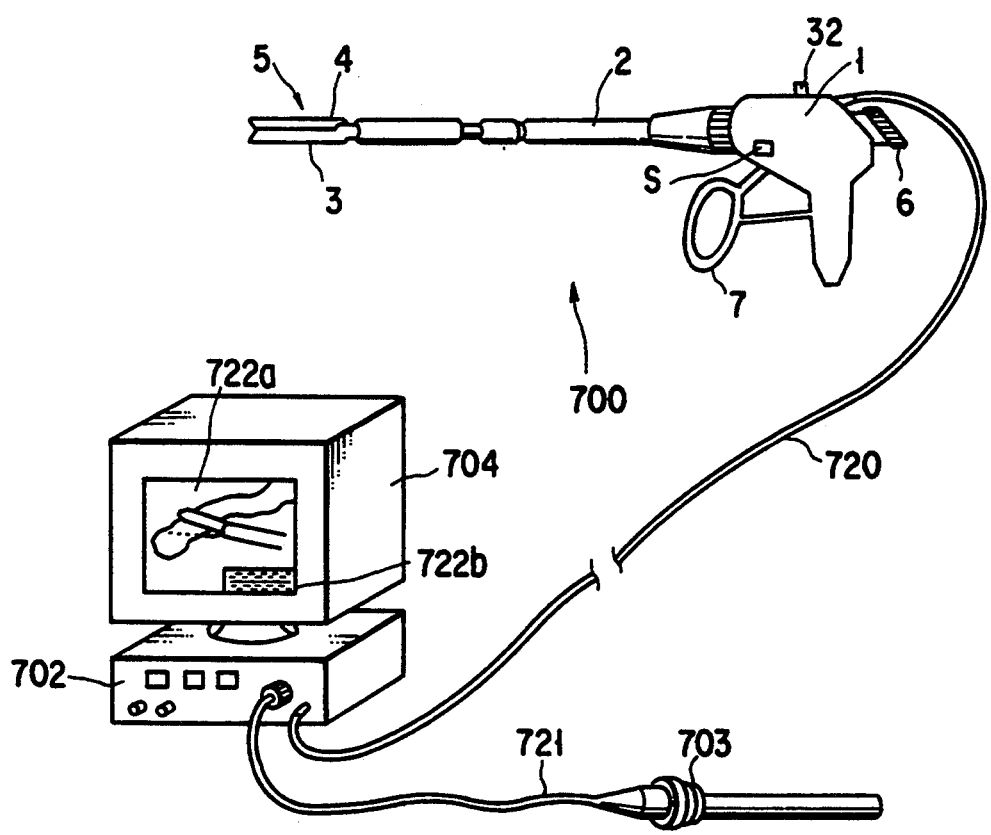
FIG. 112 is a perspective view illustrating a surgical operation system according to the present invention.

FIG. 112 is a diagram illustrating a surgical operation system, which comprises an automatic stapler 700, a camera unit 702, a scope such as a laparoscope, and a monitor display 704. The stapler 700 comprises an operation section 1, an insertion section 2, and a stapling member 5. The member 5 comprises a cartridge 3 and an anvil 4. The operation section 1 has an operating member 6, a staple-driving handle 7, and a connecting pin 32.

Pressure sensors 714 (FIG. 113) are arranged in the grooves formed in the inner surface of the anvil 4. Each sensor 714 detects the pressure with which the legs a of a staple are pushed onto the bottom of the groove. Pressure sensors (not shown) are also arranged in the cutter-guiding groove formed in the inner surface of the cartridge 3, for detecting the pressure with which a cutter (not shown) is pressed on the bottom of the cutter-guiding groove.

The operation section 1 of the automatic stapler 700 is connected by a cable 720 to the camera unit 702. The scope 703 is connected to the camera unit 702 by a cable 721. Further, the monitor display 704 is connected to the camera unit 702.

The monitor display 704 has a display screen which consists of a main screen and a sub-screen. The main screen is used to display the interior of the body cavity into which the scope 703 will be inserted. The sub-screen is smaller than the main screen and used to display images indicating the condition of the target tissues ligated with staples and the condition of the tissues severed by the cutter. The images have been formed by processing the pressures detected by the pressure sensors described above.

The sub-screen consists of two sections. The first section displays images of the staples which can represented in different colors, each color showing the stapled condition of the tissues together. The second section displays an image of the cutter-guiding groove which can be represented in different colors, each color indicating the severed condition of the stapled tissues.

As is shown in FIG. 114, the camera unit 702 contains an image-forming unit 725 and a superimposing circuit 726. The pressure sensors 714 incorporated in the stapler 700 and the pressure sensor located in the cutter-guiding groove are connected to the image-forming unit 725. The unit 725 processes the data showing the pressures detected by the sensors 714 and the pressure sensor arranged in the cutter-guiding groove, thereby forming images of the staples and an image of the cutter-guiding groove from. As mentioned above, the color which the image of each staple assumes indicates the stabled condition of the tissues, and the color which the image of the cutter-guiding groove assumes represents the severed condition of the tissues.

The image-forming unit 725, the CCD (Charge-Coupled Device) 724 incorporated in the scope 703, and the monitor display 704 are connected to the superimposing circuit 726. The CCD 724 generates data representing the image of the body-cavity interior which the scope 703 has scanned. This data is input to the superimposing circuit 726. The data which the image-forming unit 725 has generated and which represents the stapled condition and the tissues and the severed condition thereof is also input to the superimposing circuit 726. The circuit 726 processes the input data items, generating image signals. The image signals are supplied to the monitor display 704, which displays the image of the body cavity interior on the main screen, the images of the staples in the first section of the sub-screen, and the image of the cutter-guiding groove in the second section of the sub-screen.

In the surgical operation system, each pressure sensor 714 located in the groove formed the anvil 4 detects the pressure bending pushing the legs of the staple inwardly to each other to fasten the tissues together. The data representing the pressures measured by the sensors 714 is supplied to the image-forming unit 725. The image-forming unit 725 generates data showing the condition in which each staple fastens the tissues together, and this data is input to the superimposing circuit 726. The circuit 726 processes the data and the image data output by the scope 703, producing image signals. The image signals are input to the monitor display 704. The display 704 displays the image of the body cavity interior on the main screen, the images of the staples in the first section of the sub-screen, and the image of the cutter-guiding groove in the second section of the sub-screen.

If a staple is driven and pierces the tissues, with its legs bent appropriately, the sensor 714 detects the pressure the legs has Just exerted to it. This pressure is represented by the color of the image of the staple, which is displayed in the first section of the sub-screen of the monitor display 704. From the color of the staple image it is possible to determine the condition of those portions of the tissues which are ligated by that staple.

As the cutter is thrust forward along the cutter-guiding groove, cutting the stapled tissues, it pushes the pressure sensor located in the cutter-guiding groove. This sensor detects the pressure it receives and generates a signal presenting the pressure detected. The signal is input to the image-forming unit 725, which produces data representing an image of the cutter-guiding groove in the color corresponding to the pressure the cutter has exerted on the pressure sensor. The image of the groove is eventually displayed by the monitor display 704. The color of the image of the groove, thus displayed, indicates the severed condition of the tissues.

Just recognizing the colors in which the images of the staples and the cutter-guiding groove, all displayed on the sub-screen of the monitor display 704, a surgeon can determine whether or not the tissues have been stapled properly and severed appropriately. If the surgeon finds that any staple has failed to fasten the tissues in a desirable manner, he or she may operates the stapling member 5 again to make the staple ligate the tissues appropriately. Thus, no staples are left in undesirable state, which prevents the body fluid oozing from the ligated tissues.

The operating member 6 on the frame of the operation section 2 is manually operated to open and close the stapling member 5. Instead, the member 5 may be opened an closed by an electric drive unit. FIG. 113 shows such an electric drive unit 747 incorporated in the operation section 1.

As shown in FIG. 113, the electric drive unit 747 comprises a rod 741, a transmission 742, a drive motor 743, and an drive mechanism 727. The transmission 742 comprises a worm and a worm wheel. The rod 741 is connected at its rear end to the worm of the transmission and at its forward end to an outer tube 9 of the same type as shown in FIGS. 4 and 5. The worm wheel is mounted on the shaft of the motor 743. Hence, when the motor 743 is rotated, the rod 741 moves along its axis, thereby moving the outer tube 9 back and forth.

As is shown in FIG. 114, the signals output by the pressure sensors 714 and the signal output by the pressure sensor located in the cutter-guiding groove are input to a controller 744. From these signals the controller 744 generates a control signal, which is supplied to a servo amplifier 745. The amplifier 745 amplifies the control signal. The amplified signal is supplied to the drive motor 743, driving the motor 743. Thus, the motor 743 is controlled by the signals output by the pressure sensors 714 and the signal output by the pressure sensor located in the cutter-guiding groove.

Therefore, the body tissues clamped between the cartridge 3 and the anvil 4 can be automatically fastened together, uniformly at any part of them. If an excessively high pressure is found to be applied on certain parts of the tissues, for example, the stapling member 5 is opened until the pressure decreased to a desirable value, and then a staple is driven into those part of the tissues. The tissues would not be clamped too tightly at some parts and too loosely at the others, and can therefore be stapled uniformly.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A surgical device for stapling and fastening body tissues, comprising:
   an operation section operated outside a body cavity;
   an insertion section extending from said operation section for insertion into a body cavity;
   high-frequency applying means provided at a distal end portion of said insertion section, for applying a high-frequency wave to body tissues within a body cavity;
   a cartridge provided at the distal end portion of the insertion section, said cartridge containing a plurality of staples, the staples each having at least two legs which are to be inserted into the body tissues;
   staple-applying means provided at the distal end portion of the insertion section, and coupled to said cartridge for applying at least one staple from said cartridge to target tissues through said distal end portion of said insertion section;
   staple-deforming means provided at the distal end portion of the insertion section for deforming the at least one staple applied to the target tissues by said staple-applying means, thereby stapling the target tissues together; and
   current-supplying means, extending through said insertion section from said operation section to said high-frequency applying means, for supplying a high-frequency current to said high-frequency applying means to prevent bleeding of treated target tissues, said high-frequency applying means being electrically connected to the at least one staple applied to the target tissues and applying high-frequency waves to the at least one staple;
   said cartridge, said staple-applying means and said staple-deforming means all being operatable by operating said operation section.

2. The surgical device according to claim 1, further comprising:
   a cutter for cutting the target tissues, said cutter being provided at said distal end portion of said insertion section; and wherein:
   said staple-deforming means and said cartridge are located near said high-frequency applying means in order to staple the target tissues to be cut by said cutter.

3. The surgical device according to claim 2, wherein:
   said cutter comprises an electrically conductive cutter; and
   said high-frequency applying means includes means for applying a high-frequency wave to said cutter to prevent bleeding due to cutting of the target tissues.

4. The surgical device according to claim 1, wherein said staple-deforming means comprises:
   first deforming means for deforming a first leg of the at least one staple;
   second deforming means for deforming a second leg of the at least one staple; and
   drive means for selectively driving said first and second deforming means.

5. A surgical device for stapling and fastening body tissues, comprising:
   an operation section operated outside a body cavity;
   an insertion section extending from said operation section for insertion into a body cavity;
   high-frequency applying means provided at a distal end portion of said insertion section for applying a high-frequency wave to body tissues within a body cavity;
   a cartridge provided at the distal end portion of the insertion section, said cartridge containing a plurality of staples, the staples each having at least two legs which are to be inserted into the body tissues;
   staple-applying means provided at the distal end portion of the insertion section, and coupled to said cartridge for applying at least one staple from said cartridge to target tissues through said distal end portion of said insertion section;
   staple-deforming means, including an anvil, provided at the distal end portion of the insertion section for deforming the at least one staple applied to the target tissues by said staple-applying means, thereby stapling the target tissues together; and
   current-supplying mean, extending through said insertion section from said operation section to said high-frequency frequency applying means, for supplying a high-frequency current to said high-frequency applying means to prevent bleeding of treated target tissues, said high-frequency applying means being electrically connected to the at least one staple applied to the target tissues and applying high-frequency waves to the at least one staple;
   said cartridge, said staple-applying means and said staple-deforming all means being operatable by operating said operation section;
   said anvil and said cartridge being rotatably connected to said distal end portion of said insertion section and have opposing surfaces between which target tissues are held;
   said staple-applying means applying the staples from said cartridge toward said anvil such that the legs of a staple pierce the target tissues;
   said anvil and said cartridge each having a proximal portion extending in a same direction as said insertion section, and a distal portion curving in a plane perpendicular to a direction of applying the staple;
   an electrically conductive cutter for cutting the target tissues, said cutter being provided at said distal end portion of said insertion section;
   said staple-deforming means and said cartridge being located near said high-frequency applying means in order to staple the target tissues to be cut by said cutting; and said high-frequency applying means includes means for applying a high-frequency wave to said cutter to prevent bleeding due to cutting of the target tissues.

6. The surgical device according to claim 5, wherein said cutter comprises:
a cutter guide formed in the opposing surfaces of said anvil and cartridge and curving along the lengths of the distal portions of said anvil and cartridge; and
drive means for moving said cutter along said cutter guide.

7. The surgical device according to claim 6, wherein:
said staple-applying means comprises a plurality of holes formed in the opposing surface of said cartridge, through which to apply the staples, said holes being arranged on both sides of said cutter guide; and
said staple deforming means comprises a plurality of grooves formed in the opposing surface of said anvil, said grooves opposing said holes of said staple-applying means.

8. The surgical device according to claim 6, wherein said operation section comprises:
a connecting section for connecting said current-supplying means to a high frequency cautery device;
an operating section for opening and closing said anvil and said cartridge; and
a drive section for driving said cutter and said staple-applying means.

9. The surgical device according to claim 6, wherein said drive means and said staple-applying means each respectively include flexible portions which are bendable along the cutter guide.

10. A surgical device for stapling and fastening body tissues, comprising:
an operation section operated outside a body cavity;
an insertion section extending from said operation section for insertion into a body cavity;
high-frequency applying means provided at a distal end portion of said insertion section, for applying a high-frequency wave to body tissues within a body cavity;
a cartridge provided at the distal end portion of the insertion section, said cartridge containing a plurality of staples, the staples each having at least two legs which are to be inserted into the body tissues;
staple-applying means provided at the distal end portion of the insertion section, and coupled to said cartridge for applying at least one staple from said cartridge to target tissues through said distal end portion of said insertion section;
staple-deforming means provided at the distal end portion of the insertion section for deforming the at least one staple applied to the target tissues by said staple-applying means, thereby stapling the target tissues together; and
current-supplying means, extending through said insertion section from said operation section to said high-frequency applying means, for supplying a high-frequency current to said high-frequency, applying means to prevent bleeding of treated target tissues;
said cartridge, said staple-applying means and said staple-deforming all means being operatable by operating said operation section;
and wherein:
said distal end portion of said insertion section has an end face;
said staple-applying means is formed in said end face and has a staple-applying opening; and
said high-frequency applying means comprises a member projecting from said end face for supplying the high-frequency current to the target tissues when set in contact with the target tissues and for moving the target tissues in the direction of applying the staples.

11. The surgical device according to claim 10, wherein said insertion section comprises:
a rigid distal end portion;
a rigid proximal portion;
a coupling section connecting said rigid distal end portion rotatably to said rigid proximal portion; and
a drive section for rotating said rigid distal end portion.

12. The surgical device according to claim 10, wherein said high-frequency applying means is electrically connected to the at least one staple applied to the target tissues, and applies high-frequency waves to the at least one staple.

13. A surgical device for stapling and fastening body tissues, comprising:
an operation section operated outside a body cavity;
an insertion section extending from said operation section for insertion into a body cavity;
high-frequency applying means provided at a distal end portion of said insertion section for applying a high-frequency wave to body tissues within a body cavity;
a cartridge provided at the distal end portion of the insertion section, said cartridge containing a plurality of staples, the staples each having at least two legs which are to be inserted into the body tissues;
staple-applying means provided at the distal end portion of the insertion section, and coupled to said cartridge for applying at least one staple from said cartridge to target tissues through said distal end portion of said insertion section;
staple-deforming means provided at the distal end portion of the insertion section for deforming the at least one staple applied to the target tissues by said staple-applying means, thereby stapling the target tissues together; and
current-supplying means, extending through said insertion section from said operation section to said high-frequency applying means, for supplying a high-frequency current to said high-frequency applying means to prevent bleeding of treated target tissues;
said cartridge, said staple-applying means and said staple-deforming all means being operatable by operating said operation section;
and wherein:
the distal portion of said insertion section has an end face, a staple-applying opening formed in said end face, and a staple-applying section for applying a staple to the target tissues; and
the device further comprises a member projecting from said end face for moving the target tissues in the direction of applying the staples, when set in contact with the target tissues.

14. The surgical device according to claim 13, wherein said high-frequency applying means is electrically connected to the at least one staple applied to the target tissues, and applies high-frequency waves to the at least one staple.

15. The surgical device according to claim 13, wherein said high-frequency applying means is electrically connected to the at least one staple applied to the target tissues, and applies high-frequency waves to the at least one staple.

16. A surgical device for stapling and fastening body tissues, comprising:

an operation section operated outside a body cavity;

an insertion section extending from said operation section for insertion into a body cavity;

high-frequency applying means provided at a distal end portion of said insertion section, for applying a high-frequency wave to body tissues within a body cavity;

a cartridge provided at the distal end portion of the insertion section, said cartridge containing a plurality of staples, the staples each having at least two legs which are to be inserted into the body tissues;

staple-applying means provided at the distal end portion of the insertion section, and coupled to said cartridge for applying at least one staple from said cartridge to target tissues through said distal end portion of said insertion section;

staple-deforming means provided at the distal end portion of the insertion section for deforming the at least one staple applied to the target tissues by said staple-applying means, thereby stapling the target tissues together;

current-supplying means, extending through said insertion section from said operation section to said high-frequency applying means, for supplying a high-frequency current to said high-frequency applying means to prevent bleeding of treated target tissues;

said cartridge, said staple-applying means and said staple-deforming all means being operatable by operating said operation section;

a cutter for cutting the target tissues, said cutter being provided at said distal end portion of said insertion section;

said staple-deforming means and said cartridge being located near said high-frequency applying means in order to staple the target tissues to be cut by said cutter; and tying means, mounted at said distal end portion of said insertion section, for applying a tying thread to the target tissues cut by said cutter, along cut edges of the target tissues;

said tying means including means for passing a thread in a zigzag fashion into an edge of the target tissues, which are to be cut by the cutter, and for pulling the thread to contract the eden of the target tissues.

* * * * *

Adverse Decision In Interference

Patent No. 5,389,098, Minoru Tsuruta; Shiro Bito; Shuichi Kimura; Akito Mukaizawa; Seiji Kuramoto; Tsuyoshi Tsukagoshi; Akio Nakata; Akihiro Taguchi; Kazuhiko Oozeki, Hitoshi Mizno; Shuichi Takayama; Yoshinao Oaki; Keisuke Saito, Toshihiko Suzuta, SURGICAL DEVICE FOR STAPLING AND/OR FASTENING BODY TISSUES, Interference No. 103,950, final judgment adverse to the patentees rendered August 17, 2001, as to claims 1 and 3.

*(Official Gazette March 26, 2002)*